(12) United States Patent
Hynd et al.

(10) Patent No.: US 8,394,836 B2
(45) Date of Patent: Mar. 12, 2013

(54) INDOLES AND THEIR THERAPEUTIC USE

(75) Inventors: George Hynd, Essex (GB); John Gary Montana, Essex (GB); Harry Finch, Essex (GB); Rosa Arienzo, Essex (GB); Barbara Avitabile-Woo, Essex (GB); Mathias Domostoj, Essex (GB)

(73) Assignee: Pulmagen Therapeutics (Asthma) Limited, Berkshire (GB)

( * ) Notice: Subject to any disclaimer, the term of this patent is extended or adjusted under 35 U.S.C. 154(b) by 201 days.

(21) Appl. No.: 12/746,104

(22) PCT Filed: Dec. 12, 2008

(86) PCT No.: PCT/GB2008/004107
§ 371 (c)(1),
(2), (4) Date: Nov. 22, 2010

(87) PCT Pub. No.: WO2009/077728
PCT Pub. Date: Jun. 25, 2009

(65) Prior Publication Data
US 2011/0071175 A1  Mar. 24, 2011

(30) Foreign Application Priority Data

Dec. 14, 2007  (GB) .................................. 0724429.6
Apr. 3, 2008  (GB) .................................. 0806083.2
Aug. 14, 2008  (GB) .................................. 0814910.6

(51) Int. Cl.
*A61K 31/4439* (2006.01)
*C07D 409/12* (2006.01)
*C07D 401/12* (2006.01)

(52) U.S. Cl. ..................................... 514/339; 546/277.4
(58) Field of Classification Search ............... 546/277.4; 514/339
See application file for complete search history.

(56) References Cited

FOREIGN PATENT DOCUMENTS

| EP | 1505061 | 2/2005 |
|---|---|---|
| WO | WO 2005/044260 | 5/2005 |
| WO | WO 2005/054232 | 6/2005 |
| WO | WO 2006/095183 | 9/2006 |
| WO | WO 2007/138282 | 12/2007 |
| WO | WO 2008/012511 | 1/2008 |

*Primary Examiner* — Patricia L Morris
(74) *Attorney, Agent, or Firm* — Saliwanchik, Lloyd & Eisenschenk

(57) ABSTRACT

Compound of formula (I) are ligands of the CRTH2 receptor, useful inter alia for treatment of inflammatory conditions. Wherein X is —$SO_2$— or *—$SO_2NR^3$— wherein the bond marked with an asterisk is attached to $Ar^1$; $R^1$ is hydrogen, fluoro, chloro, CN or $CF_3$; $R^2$ is hydrogen, fluoro or chloro; $R^3$ is hydrogen, $C_1C_8$alkyl or $C_3$-$C_7$cycloalkyl; $Ar^1$ is phenyl or a 5- or 6-membered heteroaryl group selected from furanyl, thienyl, oxazolyl, thiazolyl, imidazolyl, pyrazolyl, isoxazolyl, isothiazolyl, pyridinyl, pyridazinyl, pyrimidinyl and pyrazinyl, wherein the phenyl or heteroaryl groups are optionally substituted by one or more substituents independently selected from fluoro, chloro, CN, $C_3$-$C_7$cycloalkyl, —$O(C_1$-$C_4$alkyl) or $C_1C_6$alkyl, the latter two groups being optionally substituted by one or more fluoro atoms; and $Ar^2$ is phenyl or 5- or 6-membered heteroaryl group selected from pyrrolyl, furanyl, thienyl, oxazolyl, thiazolyl, imidazolyl, pyrazolyl, isoxazolyl, isothiazolyl, pyridinyl, pyridazinyl, pyrimidinyl and pyrazinyl, wherein the phenyl or heteroaryl groups are optionally substituted by one or more substituents independently selected from fluoro, chloro, CN, $C_3$-$C_3$-$C_7$cycloalkyl, —$O(C_1$-$C_4$alkyl) or $C_1C_6$alkyl, the latter two groups being optionally substituted by one or more fluoro atoms.

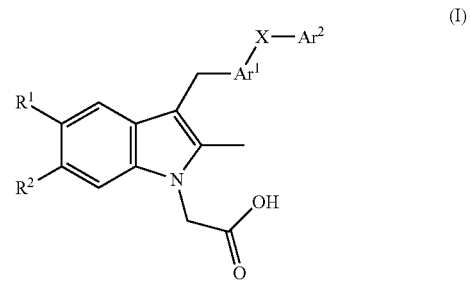

(I)

4 Claims, No Drawings

INDOLES AND THEIR THERAPEUTIC USE

CROSS-REFERENCE TO A RELATED APPLICATION

This application is a National Stage Application of International Application Number PCT/GB2008/004107, filed Dec. 12, 2008; which claims priority to Great Britain Application Nos. 0724429.6, filed Dec. 14, 2007; 0806083.2, filed Apr. 3, 2008; and 0814910.6, filed Aug. 14, 2008; all of which are incorporated herein by reference in their entirety.

This invention relates to a class of indole compounds, which are ligands of the CRTH2 receptor (Chemoattractant Receptor-homologous molecule expressed on T Helper cells type 2), and their use in the treatment of diseases responsive to modulation of CRTH2 receptor activity, principally diseases having a significant inflammatory component. The invention also relates to novel members of that class of ligands and pharmaceutical compositions containing them.

BACKGROUND TO THE INVENTION

Mast cells are known to play an important role in allergic and immune responses through the release of a number of mediators, such as histamine, leukotrienes, cytokines, prostaglandin $D_2$, etc (Boyce; Allergy Asthma Proc., 2004, 25, 27-30). Prostaglandin $D_2$ ($PGD_2$) is the major metabolite produced by the action of cyclooxygenase on arachadonic acid by mast cells in response to allergen challenge (Lewis et al; J. Immunol., 1982, 129, 1627-1631). It has been shown that $PGD_2$ production is increased in patients with systemic mastocytosis (Roberts; N. Engl. J. Med., 1980, 303, 1400-1404), allergic rhinitis (Naclerio et al; Am. Rev. Respir. Dis., 1983, 128, 597-602; Brown et al; Arch. Otolarynol. Head Neck Surg., 1987, 113, 179-183; Lebel et al, J. Allergy Clin. Immunol., 1988, 82, 869-877), bronchial asthma (Murray et al; N. Engl. J. Med., 1986, 315, 800-804; Liu et al; Am. Rev. Respir. Dis., 1990, 142, 126-132; Wenzel et al; J. Allergy Clin. Immunol., 1991, 87, 540-548), and urticaria (Heavey et al; J. Allergy Clin. Immunol., 1986, 78, 458-461). $PGD_2$ mediates it effects through two receptors, the $PGD_2$ (or DP) receptor (Boie et al; J. Biol. Chem., 1995, 270, 18910-18916) and the chemoattractant receptor-homologous molecule expressed on Th2 (or CRTH2) (Nagata et al; J. Immunol., 1999, 162, 1278-1289; Powell; Prostaglandins Luekot. Essent. Fatty Acids, 2003, 69, 179-185). Therefore, it has been postulated that agents that antagonise the effects of $PGD_2$ at its receptors may have beneficial effects in a number of disease states.

The CRTH2 receptor has been shown to be expressed on cell types associated with allergic inflammation, such as basophils, eosinophils, and Th2-type immune helper cells (Hirai et al; J. Exp. Med., 2001, 193, 255-261). The CRTH2 receptor has been shown to mediate $PGD_2$-mediated cell migration in these cell types (Hirai et al; J. Exp. Med., 2001, 193, 255-261), and also to play a major role in neutrophil and eosinophil cell recruitment in a model of contact dermatitis (Takeshita et al; Int. Immunol., 2004, 16, 947-959). Ramatroban {(3R)-3-[(4-fluorophenyl)sulphonylamino]-1,2,3,4-tetrahydro-9H-carbazole-9-propanoic acid}, a dual CRTH2 and thromboxane $A_2$ receptor antagonist, has been shown to attenuate these responses (Sugimoto et al; J. Pharmacol. Exp. Ther., 2003, 305, 347-352; Takeshita et al; op. cit.). The potential of $PGD_2$ both to enhance allergic inflammation and induce an inflammatory response has been demonstrated in mice and rats. Transgenic mice over expressing $PGD_2$ synthase exhibit an enhanced pulmonary eosinophilia and increased levels of Th2 cytokines in response to allergen challenge (Fujitani et al, J. Immunol., 2002, 168, 443-449). In addition, exogenously administered CRTH2 agonists enhance the allergic response in sensitised mice (Spik et al; J. Immunol., 2005, 174, 3703-3708). In rats exogenously applied CRTH2 agonists cause a pulmonary eosinophilia but a DP agonist (BW 245C) or a TP agonist (I-BOP) showed no effect (Shirashi et al; J. Pharmacol. Exp Ther., 2005, 312, 954-960). These observations suggest that CRTH2 antagonists may have valuable properties for the treatment of diseases mediated by $PGD_2$.

In addition to Ramatroban a number of other CRTH2 antagonists have been described. Examples include: indole acetic acids (WO2008/012511; WO2007/065684; WO2007/045867; WO2006/034419; WO2005/094816; WO2005/044260; WO2005/040114; WO2005/040112; GB2407318; WO2005/019171; WO2004/106302; WO2004/078719; WO2004/007451; WO2003/101981; WO2003/101961; WO2003/097598; WO2003/097042; WO2003/066047; WO2003/066046; WO2003/022813), indolizine acetic acids (WO2008/113965; WO2008/074966; WO2007/031747; WO2006/136859), pyrrole acetic acids (WO2007/144127; WO2006/063763), quinolines (WO2008/122784; WO2008/119917; WO2007/036743), tetrahydroquinolines (WO2006/091674; US2005/256158; WO2005/100321; WO2005/007094; WO2004/035543; WO2004/032848; EP1435356; EP1413306), phenoxyacetic acids (WO2007/062678; WO2007/062773; WO2006/125596; WO2006/125593; WO2006/056752; WO2005/115382; WO2005/105727; WO2005/018529; WO2004/089885; WO2004/089884) and phenylacetic acids (WO2004/058164).

DETAILED DESCRIPTION OF THE INVENTION

One aspect of the invention provides indole derivatives of formula (I):

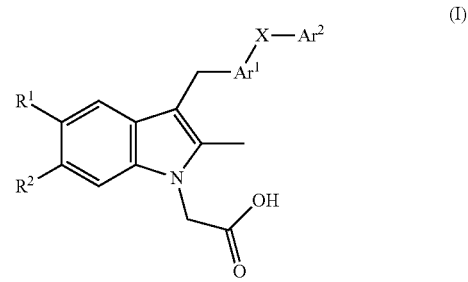

X is —$SO_2$— or *—$SO_2NR^3$— wherein the bond marked with an asterisk is attached to $Ar^1$;

$R^1$ is hydrogen, fluoro, chloro, CN or $CF_3$;

$R^2$ is hydrogen, fluoro or chloro;

$R^3$ is hydrogen, $C_1$-$C_8$alkyl or $C_3$-$C_7$cycloalkyl;

$Ar^1$ is phenyl or a 5- or 6-membered heteroaryl group selected from furanyl, thienyl, oxazolyl, thiazolyl, imidazolyl, pyrazolyl, isoxazolyl, isothiazolyl, pyridinyl, pyridazinyl, pyrimidinyl and pyrazinyl, wherein the phenyl or heteroaryl groups are optionally substituted by one or more substituents independently selected from fluoro, chloro, CN, $C_3$-$C_7$cycloalkyl, —O($C_1$-$C_4$alkyl) or $C_1$-$C_6$alkyl, the latter two groups being optionally substituted by one or more fluoro atoms;

$Ar^2$ is phenyl or 5- or 6-membered heteroaryl group selected from pyrrolyl, furanyl, thienyl, oxazolyl, thiazolyl, imidazolyl, pyrazolyl, isoxazolyl, isothiazolyl, pyridinyl, pyridazinyl, pyrimidinyl and pyrazinyl, wherein the phenyl or heteroaryl groups are optionally substituted by one or more substituents independently selected from fluoro, chloro, CN, $C_3$-$C_7$cycloalkyl, —O($C_1$-$C_4$alkyl) or $C_1$-$C_6$alkyl, the latter two groups being optionally substituted by one or more fluoro atoms.

Compounds (I) with which the invention is concerned are CRTH2 receptor antagonists, but they may also have beneficial effects at other prostanoid receptors, such as the $PGD_2$ receptor or the thromboxane $A_2$ receptor.

Compounds of formula (I) above may be prepared or recovered in the form of salts, and in some cases as N-oxides, hydrates, and solvates thereof. Any reference herein, including the claims herein, to "compounds of the invention", "compounds with which the invention is concerned" or "compounds of formula (I)" and the like, includes reference to salts, particularly pharmaceutically acceptable salts, N-oxides, hydrates, and solvates of such compounds.

The invention also includes (i) use of a compound with which the invention is concerned in the manufacture of a medicament for use in the treatment of conditions responsive to modulation of CRTH2 receptor activity, and (ii) a method of treatment of conditions responsive to modulation of CRTH2 receptor activity, comprising administering to a patient suffering such disease an effective amount of a compound with which the invention is concerned.

Examples of conditions responsive to modulation of CRTH2 receptor activity include asthma, rhinitis, allergic airway syndrome, allergic rhinobronchitis, bronchitis, chronic obstructive pulmonary disease (COPD), nasal polyposis, sarcoidosis, farmer's lung, fibroid lung, cystic fibrosis, chronic cough, conjunctivitis, atopic dermatitis, Alzheimer's disease, amyotrophic lateral sclerosis, AIDS dementia complex, Huntington's disease, frontotemporal dementia, Lewy body dementia, vascular dementia, Guillain-Barre syndrome, chronic demyelinating polyradiculoneurophathy, multifocal motor neuropathy, plexopathy, multiple sclerosis, encephalomyelitis, panencephalitis, cerebellar degeneration and encephalomyelitis, CNS trauma, migraine, stroke, rheumatoid arthritis, ankylosing spondylitis, Behçet's Disease, bursitis, carpal tunnel syndrome, inflammatory bowel disease, Crohn's disease, ulcerative colitis, dermatomyositis, Ehlers-Danlos Syndrome (EDS), fibromyalgia, myofascial pain, osteoarthritis (OA), osteonecrosis, psoriatic arthritis, Reiter's syndrome (reactive arthritis), sarcoidosis, scleroderma, Sjogren's Syndrome, soft tissue disease, Still's Disease, tendinitis, polyarteritis Nodossa, Wegener's Granulomatosis, myositis (polymyositis dermatomyositis), gout, atherosclerosis, lupus erythematosus, systemic lupus erythematosus (SLE), type I diabetes, nephritic syndrome, glomerulonephritis, acute and chronic renal failure, eosinophilia fascitis, hyper IgE syndrome, sepsis, septic shock, ischemic reperfusion injury in the heart, allograft rejection after transplantations, and graft versus host disease.

However, the compounds with which the invention is concerned are primarily of value for the treatment of asthma, chronic obstructive pulmonary disease, rhinitis, allergic airway syndrome, or allergic rhinobronchitis. Psoriasis, atopic and non-atopic dermatitis Crohn's disease, ulcerative colitis, and irritable bowel disease are other specific conditions where the present compounds may have particular utility.

Another aspect of the invention is a pharmaceutical composition comprising a compound with which the invention is concerned in admixture with a pharmaceutically acceptable carrier or excipient.

Terminology

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the term "salt" includes base addition, acid addition and quaternary salts. Compounds of the invention which are acidic can form salts, including pharmaceutically acceptable salts, with bases such as alkali metal hydroxides, for example sodium and potassium hydroxides; alkaline earth metal hydroxides, for example calcium, barium and magnesium hydroxides; with organic bases, for example N-methyl-D-glucamine, choline tris(hydroxymethyl)aminomethane, L-arginine, L-lysine, N-ethyl piperidine, dibenzylamine and the like. Specific salts with bases include the piperazine, ethanolamine, benzathine, calcium, diolamine, meglumine, olamine, potassium, procaine, sodium, tromethamine and zinc salts. Those compounds of the invention which are basic can form salts, including pharmaceutically acceptable salts with inorganic acids, for example with hydrohalic acids such as hydrochloric or hydrobromic acids, sulphuric acid, nitric acid or phosphoric acid and the like, and with organic acids, for example acetic, tartaric, succinic, fumaric, maleic, malic, salicylic, citric, methanesulphonic, p-toluenesulphonic, benzoic, benzenesulfonic, glutamic, lactic and mandelic acids and the like. Where a compound contains a quaternary ammonium group acceptable counter-ions may be, for example chlorides, bromides, sulfates, methanesulfonates, benzenesulfonates, toluenesulfonates (tosylates), napadisylates (naphthalene-1,5-disulfonates or naphthalene-1-(sulfonic acid)-5-sulfonates), edisylates (ethane-1,2-disulfonates or ethane-1-(sulfonic acid)-2-sulfonates), isethionates 2-hydroxyethylsulfonates), phosphates, acetates, citrates, lactates, tartrates, mesylates, maleates, malates, fumarates, succinates, xinafoates, p-acetamidobenzoates and the like; wherein the number of quaternary ammonium species balances the pharmaceutically acceptable salt such that the compound has no net charge.

Salts are discussed in the "Handbook of Pharmaceutical Salts. Properties, selection and use", P. Heinrich Stahl & Camille G. Wermuth, Wiley-VCH, 2002.

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned may exist in one or more stereoisomeric form, because of the presence of asymmetric atoms or rotational restrictions, and in such cases can exist as a number of stereoisomers with R or S stereochemistry at each chiral centre or as atropisomers with R or S stereochemistry at each chiral axis. The invention includes all such enantiomers and diastereoisomers and mixtures thereof.

Use of prodrugs, such as esters, of compounds with which the invention is concerned is also part of the invention. "Prodrug" means a compound that is convertible in vivo by metabolic means (for example, by hydrolysis, reduction or oxidation) to a compound of formula (I). For example an ester prodrug of a compound of formula (I) may be convertible by hydrolysis in vivo to the parent molecule. Suitable esters of compounds of formula (I) are for example acetates, citrates, lactates, tartrates, malonates, oxalates, salicylates, propionates, succinates, fumarates, maleates, methylene-bis-β-hydroxynaphthoates, gentisates, isethionates, di-p-toluoyl-tartrates, methanesulphonates, ethanesulphonates, benzenesulphonates, p-toluene-sulphonates, cyclohexylsulphamates and quinates. Examples of ester prodrugs are those described by F. J. Leinweber, Drug Metab. Res., 1987, 18, 379. As used in herein, references to the compounds of formula (I) are meant to also include the prodrug forms.

Structural Aspects of Compounds with which the Invention is Concerned

Subject to the proviso in the above definition of compounds with which the invention is concerned:

$R^1$ is hydrogen, fluoro, chloro, CN or $CF_3$ and $R^2$ is hydrogen, fluoro or chloro. In one particular subset of compounds of the invention $R^1$ is fluoro and $R^2$ is hydrogen. In another subset of compounds of the invention $R^1$ is chloro and $R^2$ is hydrogen. All combinations of the permitted substituents $R^1$ and $R^2$ are allowed.

$Ar^1$ is phenyl or 5- or 6-membered heteroaryl group selected from furanyl, thienyl, oxazolyl, thiazolyl, imidazolyl, pyrazolyl, isoxazolyl, isothiazolyl, pyridinyl, pyridazinyl, pyrimidinyl and pyrazinyl. In some cases, $Ar^1$ is phenyl, thienyl, pyridinyl, pyrimidinyl imidazolyl, isothiazolylor thiazolyl.

$Ar^2$ is phenyl or 5- or 6-membered heteroaryl. Examples of such rings include phenyl, pyrrolyl, imidazolyl, furanyl, thienyl, oxazolyl, thiazolyl, pyrazolyl, isoxazolyl, isothiazolyl, pyridinyl, pyrazinyl, pyrimidinyl and pyridazinyl. In some cases ring $Ar^2$ is phenyl or pyridinyl.

In one particular subclass of compounds of the invention, X is *—$SO_2NR^3$— wherein the bond marked with an asterisk is attached to $Ar^1$.

in some compounds of the invention, $Ar^1$ is phenyl and $Ar^2$ is selected from pyrrolyl, furanyl, thienyl, oxazolyl, thiazolyl, imidazolyl, pyrazolyl, isoxazolyl, isothiazolyl, pyridinyl, pyridazinyl, pyrimidinyl and pyrazinyl.

In some other compounds of the invention, $Ar^1$ selected from furanyl, thienyl, oxazolyl, thiazolyl, imidazolyl, pyrazolyl, isoxazolyl, isothiazolyl, pyridinyl, pyridazinyl, pyrimidinyl and pyrazinyl, phenyl and $Ar^2$ is phenyl.

When ring $Ar^1$ is heteroaryl it may be selected from, for example, thienyl, pyridinyl, pyrimidinyl, thiazolyl, isothiazolyl and imidazolyl.

When ring $Ar^2$ is heteroaryl it may be selected from, for example, thienyl, pyridinyl, and pyrimidinyl.

$Ar^1$ and $Ar^2$ may be optionally be substituted by one or more substituents independently selected from fluoro, chloro, CN, $C_3$-$C_7$cycloalkyl such as cyclopropyl, $O(C_1$-$C_4$alkyl) such as methoxy, $C_1$-$C_6$alkyl such as methyl or the latter two groups being optionally substituted by one or more fluoro atoms, as in the case of trifluormethoxy or trifluoromethyl. Currently preferred such substituents are chloro, fluoro, CN and methyl.

The radical $Ar^2SO_2$— or $Ar^2N(R^3)SO_2$— may be in the meta- or para-position of the ring $Ar^1$ relative to the point of attachment of $Ar^1$ to the rest of the molecule.

However, currently it is preferred that the radicals $Ar^2SO_2$— or $Ar^2SO_2NR^3$— are in the ortho-position of the ring $Ar^1$ relative to the point of attachment of $Ar^1$ to the rest of the molecule.

Specific compounds of the invention include those of the Examples herein.

Compositions

As mentioned above, the compounds with which the invention is concerned are CRTH2 receptor antagonists, and are useful in the treatment of diseases, which benefit from such modulation. Examples of such diseases are referred to above, and include asthma, rhinitis, allergic airway syndrome, bronchitis and chronic obstructive pulmonary disease.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range will lie within the range of from about 0.001 mg to about 100 mg per kg body weight of a mammal, often 0.01 mg to about 50 mg per kg, for example 0.1 to 10 mg per kg, in single or divided doses. On the other hand, it may be necessary to use dosages outside these limits in some cases.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations, which may be used for the drug, are conventional formulations well known in the art, for example as described in standard textbooks of pharmaceutics such as the British Pharmacopoeia.

The drug may also be formulated for inhalation, for example as a nasal spray, or dry powder or aerosol inhalers. For delivery by inhalation, the active compound is preferably in the form of microparticles. They may be prepared by a variety of techniques, including spray-drying, freeze-drying and micronisation. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active ingredient may also be administered parenterally in a sterile medium. Depending on the vehicle and concentration used, the drug can either be suspended or dissolved in the vehicle. Advantageously, adjuvants such as local anaesthetic, preservative and buffering agents can be dissolved in the vehicle.

Other compounds may be combined with compounds with which the invention is concerned for the prevention and treatment of prostaglandin-mediated diseases. Thus the present invention is also concerned with pharmaceutical compositions for preventing and treating $PGD_2$-mediated diseases comprising a therapeutically effective amount of a compound of the invention and one or more other therapeutic agents. Suitable therapeutic agents for a combination therapy with compounds of the invention include, but are not limited to: (1) corticosteroids, such as fluticasone, ciclesonide or budesonide; (2) β2-adrenoreceptor agonists, such as salmeterol, indacaterol or formoterol; (3) leukotriene modulators, for example leukotriene antagonists such as montelukast, zafirulast or pranlukast or leukotriene biosynthesis inhibitors such as Zileuton or BAY-1005; (4) anticholinergic agents, for example muscarinic-3 (M3) receptor antagonists such as tiotropium bromide; (5) phosphodiesterase-IV (PDE-IV) inhibitors, such as roflumilast or cilomilast; (6) antihistamines, for example selective histamine-1 (H1) receptor antagonists, such as fexofenadine, citirizine, loratidine or astemizole; (7) antitussive agents, such as codeine or dextramorphan; (8) non-selective COX-1/COX-2 inhibitors, such as ibuprofen or ketoprofen; (9) COX-2 inhibitors, such as celecoxib and rofecoxib; (10) VLA-4 antagonists, such as those described in WO97/03094 and WO97/02289; (11) TACE inhibitors and TNF-α inhibitors, for example anti-TNF monoclonal antibodies, such as Remicade and CDP-870 and TNF receptor immunoglobulin molecules, such as Enbrel; (12) inhibitors of matrix metalloprotease, for example MMP12; (13) human neutrophil elastase inhibitors, such as those described in WO2005/026124, WO2003/053930 and WO06/082412; (14) A2a agonists such as those described in EP1052264 and EP1241176 (15) A2b antagonists such as those described in WO2002/42298; (16) modulators of chemokine receptor function, for example antagonists of CCR3 and CCR8; (17) compounds which modulate the action of other prostanoid receptors, for example a thromboxane $A_2$ antagonist; and (18) agents that modulate Th2 function, such as PPAR agonists.

The weight ratio of the compound of the invention to the second active ingredient may be varied and will depend upon the effective dose of each ingredient. Generally, an effective dose of each will be used.

Synthesis

There are multiple synthetic strategies for the synthesis of the compounds with which the present invention is concerned, but all rely on chemistry known to the synthetic organic chemist. Thus, compounds of the invention can be synthesised according to procedures described in the standard literature and are well-known to the one skilled in the art. Typical literature sources are "*Advanced organic chemistry*", 4$^{th}$ Edition (Wiley), J. March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky, review articles such as found in "*Synthesis*", "*Acc. Chem. Res.*", "*Chem. Rev.*", or primary literature sources identified by standard literature searches online or from secondary sources such as "*Chemical Abstracts*" or "*Beilstein*". The extensive literature relating to the synthesis of indole compounds is especially relevant, of course.

It may be necessary to protect reactive functional groups (for example, hydroxy, amino, thio or carboxy) in intermediates used in the preparation of compounds of formula (I) to avoid their unwanted participation in a reaction leading to the formation of compounds of formula (I). Conventional protecting groups, for example those described by T. W. Greene and P. G. M. Wuts in "Protective groups in organic chemistry" John Wiley and Sons, 1999, may be used.

The compounds of the invention of formula (I) may be isolated in the form of their pharmaceutically acceptable salts, such as those described previously herein above. The free acid form corresponding to isolated salts can be generated by acidification with a suitable acid such as acetic acid and hydrochloric acid and extraction of the liberated free acid into an organic solvent followed by evaporation. The free acid form isolated in this manner can be further converted into another pharmaceutically acceptable salt by dissolution in an organic solvent followed by addition of the appropriate base and subsequent evaporation, precipitation, or crystallisation.

Compounds of formula (Ia), wherein X, $R^1$, $R^2$, $Ar^1$ and $Ar^2$ are as defined for formula (I) above, may conveniently be prepared by the reaction between an indole of formula (II), wherein E represents hydrogen or alkyl group, and an aldehyde of formula (III) (Scheme 1). The reaction is carried out under acidic reductive conditions, for example a mixture of trifluoroacetic acid and triethylsilane. It is to be understood that if the reaction is carried out on a protected form of (II) an appropriate deprotection step will be required to obtain the desired compound of the invention (Ia). Compounds of formula (II) are commercially available or can be prepared by known methods (Kim et al; J. Heterocycl. Chem., 1981, 18, 1365-71; Forbes et al; Syn. Commun., 1996, 26, 745-754).

Scheme 1

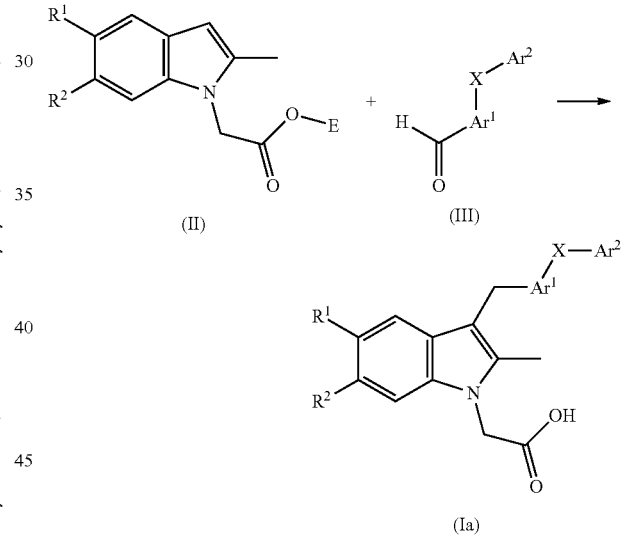

Intermediate compounds of formula (III), wherein X represents $SO_2$ group, may be prepared by the oxidation of compounds of formula (IV), with a suitable oxidising agent such as potassium peroxymonosulfate, meta-chloroperoxybenzoic acid or other well known oxidising agents (Scheme 2).

Scheme 2

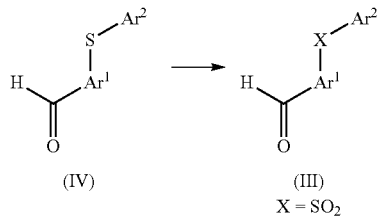

$X = SO_2$

Compounds of formula (IV) may be prepared from compounds of formula (V), wherein T represents a chloro, bromo, or iodo atom, or a trifluoromethanesulfonyloxy group, by reaction with a thiol of formula (VI) in the presence of a suitable base such as potassium carbonate (Scheme 3). Alternatively, the reaction may be carried out in the presence of a suitable catalyst, such as tetrakis(triphenylphosphine)palladium(0) in a protic solvent such as ethanol. Compounds of formula (V) and (VI) are commercially available or can be prepared by known methods.

Scheme 3

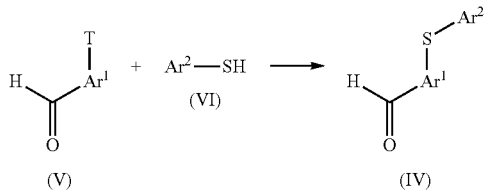

Alternatively, intermediate compounds of formula (III), wherein X represents $SO_2$ group, may be prepared by reaction of compounds of formula (V) and (VII) (Scheme 4). The reaction may be carried out in a suitable solvent such as dimethyl sulfoxide, at temperatures ranging from room temperature to 150° C. Compounds of formula (VII) are commercially available or can be prepared by known methods.

Scheme 4

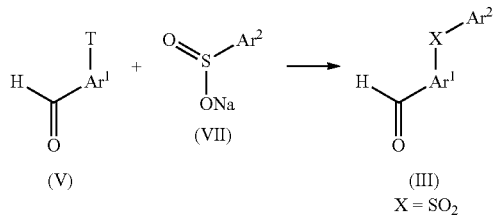

Intermediate compounds of formula (III), wherein X represents $SO_2NR^3$ group, may be prepared by the reaction between a compound of formula (VIII) and an amine of formula (IX) (Scheme 5). The reaction may be carried out in the presence of a suitable base (for example, triethylamine or diisopropylethylamine) and solvent (for example, dichloromethane or dichloroethane), at temperatures ranging from 0° C. to the reflux temperature of the solvent, preferably at about room temperature. Compounds of formula (VIII) and (IX) are commercially available or can be prepared by known methods.

Scheme 5

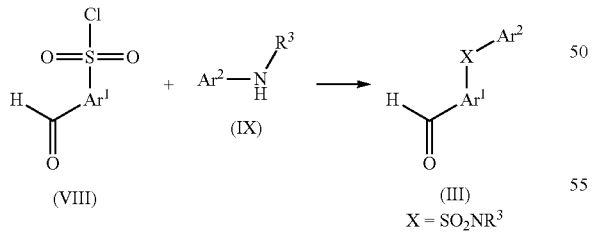

EXAMPLES $^1$H NMR spectra were recorded at ambient temperature using a Varian Unity Inova (400 MHz) spectrometer with a triple resonance 5 mm probe spectrometer. Chemical shifts are expressed in ppm relative to tetramethylsilane. The following abbreviations have been used: br s=broad singlet, s=singlet, d=doublet, dd=double doublet, t=triplet, q=quartet, m=multiplet.

Mass Spectrometry (LCMS) experiments to determine retention times and associated mass ions were performed using the following methods:

Method A: experiments were performed on a Micromass Platform LCT spectrometer with positive ion electrospray and single wavelength UV 254 nm detection using a Higgins Clipeus C18 5 μm 100×3.0 mm column and a 2 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 2 minutes.

Method B: experiments were performed on a Micromass Platform LC spectrometer with positive and negative ion electrospray and ELS/Diode array detection using a Phenomenex Luna C18(2) 30×4.6 mm column and a 2 mL/minute flow rate. The solvent system was 95% solvent A and 5% solvent B for the first 0.50 minutes followed by a gradient up to 5% solvent A and 95% solvent B over the next 4 minutes. The final solvent system was held constant for a further 0.50 minutes Microwave experiments were carried out using a Personal Chemistry Smith Synthesizer™, which uses a single-mode resonator and dynamic field tuning, both of which give reproducibility and control. Temperatures from 40-250° C. can be achieved, and pressures of up to 20 bars can be reached. Two types of vial are available for this processor, 0.5-2.0 mL and 2.0-5.0 mL.

Reverse-phase preparative HPLC purifications were carried out using Genesis 7 micron C-18 bonded silica stationary phase in columns 10 cm in length and 2 cm internal diameter. The mobile phase used was mixtures of acetonitrile and water (both buffered with 0.1% v/v trifluoroacetic acid or formic acid) with a flow rate of 10 mL per minute and typical gradients of 40 to 90% organic modifier ramped up over 30 to 40 minutes. Fractions containing the required product (identified by LCMS analysis) were pooled, the organic fraction removed by evaporation, and the remaining aqueous fraction lyophilised, to give the final product.

Example 1

{5-fluoro-3-[3-(4-fluorobenzenesulfonyl)thiophen-2-ylmethyl]-2-methylindol-1-yl}acetic acid

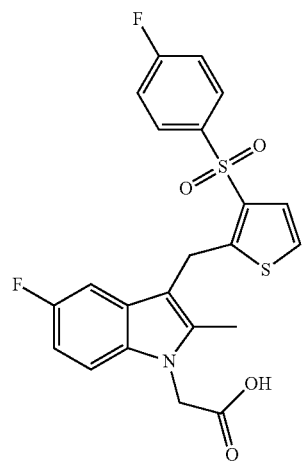 [SMILES: Cc1c(Cc2sccc2S(=O)(=O)c2ccc(F)cc2)c2cc(F)ccc2n1CC(=O)O]

Preparation 1a: 3-(4-fluorophenylsulfanyl)thiophene-2-carbaldehyde

A mixture of sodium hydride (0.20 g) and n-butanol (10 mL) was treated with 4-fluorothiophenol (0.64 g), and the resulting mixture was added to a mixture of 3-bromothiophene-2-carbaldehyde (0.96 g), tetrakis(triphenylphosphine)palladium (0) (0.12 g) and n-butanol (5.0 mL). The resulting mixture was stirred at 100° C. for 2 hours and then at 120° C. for 4 hours. The mixture was cooled to room temperature, concentrated under reduced pressure and the residue partitioned between water and ethyl acetate. The aqueous phase was extracted with ethyl acetate, and the combined organic solution was dried over sodium sulfate and concentrated under reduced pressure. The residue was purified by column chromatography on silica gel, eluting with a mixture of cyclohexane and dichloromethane (2:1 to 0:1 by volume) to afford the title compound as a yellow solid (0.78 g).

$^1$H NMR (CDCl$_3$): δ 6.72 (d, J=5.1 Hz, 1H), 7.08 (t, J=8.6 Hz, 2H), 7.42-7.48 (m, 2H), 7.62 (dd, J=1.0, 5.1 Hz, 1H), 10.11 (d, J=1.0 Hz, 1H).

Preparation 1b: 3-(4-fluorobenzenesulfonyl)thiophene-2-carbaldehyde

A solution of 3-(4-fluorophenylsulfanyl)thiophene-2-carbaldehyde (0.60 g) in dichloromethane (6.0 mL) at 0° C. was treated dropwise with a solution of 3-chloroperoxybenzoic acid (1.3 g) in dichloromethane (12 mL), and the resulting mixture was stirred at 0° C. for 15 minutes and then at room temperature for 3 hours. The mixture was partitioned between saturated aqueous sodium hydrogen carbonate solution and ethyl acetate. The aqueous phase was extracted with ethyl acetate, and the combined organic solution was dried over sodium sulfate and concentrated under reduced pressure. The residue was purified by column chromatography on silica gel, eluting with a mixture of cyclohexane and dichloromethane (1:3 to 0:1 by volume) to afford the title compound as a white solid (0.36 g).

$^1$H NMR (CDCl$_3$): δ 7.22-7.26 (m, 2H), 7.46 (d, J=5.2 Hz, 1H), 7.71 (dd, J=1.2, 5.2 Hz, 1H), 7.96-8.01 (m, 2H), 10.63 (d, J=1.2 Hz, 1H).

Preparation 1c: {5-fluoro-3-[3-(4-fluorobenzenesulfonyl)thiophen-2-ylmethyl]-2-methylindol-1-yl}acetic acid methyl ester A mixture of triethylsilane (0.79 g), trifluoroacetic acid (0.47 g) and 1,2-dichloroethane (2.0 mL) at −10° C. was treated dropwise with a mixture of (5-fluoro-2-methylindol-1-yl)acetic acid methyl ester (0.1 g), 3-(4-fluorobenzenesulfonyl)thiophene-2-carbaldehyde (0.15 g) and 1,2-dichloroethane (3.0 mL), and the resulting mixture was stirred at −10° C. for 15 minutes and then at room temperature overnight. The mixture was diluted with dichloromethane, washed with saturated aqueous sodium hydrogen carbonate solution and dried over magnesium sulfate. The solvent was removed under reduced pressure and the residue purified by column chromatography on silica gel, eluting with a mixture of cyclohexane and dichloromethane (1:1 to 0:1 by volume) to afford the title compound as a colourless gum (0.17 g).

$^1$H NMR (CDCl$_3$): δ 2.29 (s, 3H), 3.76 (s, 3H), 4.44 (s, 2H), 4.81 (s, 2H), 6.66 (dd, J=2.5, 9.4 Hz, 1H), 6.87-6.91 (m, 1H), 7.05-7.10 (m, 2H), 7.23 (t, J=8.6 Hz, 2H), 7.41 (d, J=5.4 Hz, 1H), 8.00 (dd, J=5.4, 8.9 Hz, 2H).

Preparation 1d: {5-fluoro-3-[3-(4-fluorobenzenesulfonyl)thiophen-2-ylmethyl]-2-methylindol-1-yl}acetic acid A mixture of {5-fluoro-3-[3-(4-fluorobenzenesulfonyl)thiophen-2-ylmethyl]-2-methylindol-1-yl}acetic acid methyl ester (0.17 g), tetrahydrofuran (2.0 mL) and methanol (1.0 mL) was treated with 5.0 M aqueous sodium hydroxide solution (1.5 mL), and the resulting mixture was stirred at 40° C. overnight. The mixture was acidified by the addition of 5.0 M aqueous hydrochloric acid solution and concentrated to low bulk under reduced pressure. The resulting precipitate was collected by filtration, washed with water and dried to afford the title compound as a cream solid (0.11 g).

$^1$H NMR (CDCl$_3$): δ 2.28 (s, 3H), 4.41 (s, 2H), 4.75 (s, 2H), 6.63 (dd, J=2.4, 9.5 Hz, 1H), 6.83 (td, J=2.5, 9.0 Hz, 1H), 7.05-7.12 (m, 2H), 7.22 (t, J=8.4 Hz, 2H), 7.38 (s, 1H), 7.97 (dd, J=5.0, 8.5 Hz, 2H).

MS: ESI (+ve) (Method A): 462 (M+H)$^+$, Retention time 11.0 min.

Example 2

{5-fluoro-3-[4-(4-fluorobenzenesulfonyl)benzyl]-2-methylindol-1-yl}acetic acid

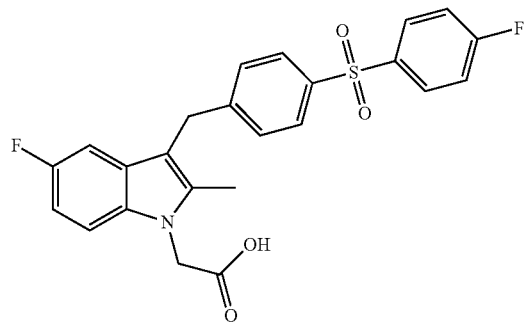 [SMILES: Cc1c(Cc2ccc(S(=O)(=O)c3ccc(F)cc3)cc2)c2cc(F)ccc2n1CC(=O)O]

Preparation 2a: 4-(4-fluorophenylsulfanyl)benzaldehyde

A mixture of 4-fluorobenzenethiol (1.0 g), potassium carbonate (2.4 g) and N,N-dimethylformamide (25 mL) was treated with 4-bromobenzaldehyde (0.73 g), and the resulting mixture was stirred at room temperature for 16 hours. The mixture was filtered and the filtrated concentrated under reduced pressure. The residue was purified by crystallisation from a mixture of diethyl ether and cyclohexane to afford the title compound as a white solid (0.89 g).

$^1$H NMR (CDCl$_3$): δ 7.10-7.21 (m, 4H), 7.51-7.56 (m, 2H), 7.70-7.74 (m, 2H), 9.92 (s, 1H).

Preparation 2b: 4-(4-fluorobenzenesulfonyl)benzaldehyde

The title compound was prepared by the method of Preparation 1b using 4-(4-fluorophenylsulfanyl)benzaldehyde.

$^1$H NMR (CDCl$_3$): δ 7.19 (t, J=8.5 Hz, 2H), 7.95-8.01 (m, 4H), 8.08 (d, J=8.2 Hz, 2H), 10.06 (s, 1H).

Preparation 2c: {5-fluoro-3-[4-(4-fluorobenzene-sulfonyl)benzyl]-2-methylindol-1-yl}acetic acid methyl ester The title compound was prepared by the method of Preparation 1c using (5-fluoro-2-methylindol-1-yl)acetic acid methyl ester and 4-(4-fluorobenzenesulfonyl)benzaldehyde.

$^1$H NMR (CDCl$_3$): δ 2.30 (s, 3H), 3.76 (s, 3H), 4.08 (s, 2H), 4.80 (s, 2H), 6.84-6.96 (m, 2H), 7.05-7.19 (m, 3H), 7.29 (d, J=8.1 Hz, 2H), 7.79 (d, J=8.2 Hz, 2H), 7.92 (dd, J=5.1, 8.9 Hz, 2H).

Preparation 2d: {5-fluoro-3-[4-(4-fluorobenzene-sulfonyl)benzyl]-2-methylindol-1-yl}acetic acid A mixture of {5-fluoro-3-[4-(4-fluorobenzenesulfonyl)benzyl]-2-methylindol-1-yl}acetic acid methyl ester (0.079 g) and tetrahydrofuran (1.0 mL) was treated with 5.0 M aqueous sodium hydroxide solution (1.5 mL), and the resulting mixture was stirred at 40° C. for 1 hour. The mixture was acidified by the addition of 5.0 M aqueous hydrochloric acid solution and concentrated under reduced pressure. The residue was purified by preparative reverse-phase HPLC, eluting with a mixture of acetonitrile and water (1:3 to 9:1 by volume) to afford the title compound as a white solid (0.056 g).

$^1$H NMR (DMSO-d$_6$): δ 2.28 (s, 3H), 4.07 (s, 2H), 4.89 (s, 2H), 6.84 (td, J=2.5, 9.2 Hz, 1H), 7.12 (dd, J=2.5, 9.9 Hz, 1H), 7.32 (dd, J=4.4, 8.9 Hz, 1H), 7.36-7.44 (m, 4H), 7.82 (d, J=8.4 Hz, 2H), 7.94-7.99 (m, 2H), 12.91 (br s, 1H).

MS: ESI (+ve) (Method A): 456 (M+H)$^+$, Retention time 11.2 min.

Example 3

{5-fluoro-3-[3-fluoro-4-(4-fluorobenzenesulfonyl)benzyl]-2-methylindol-1-yl}acetic acid

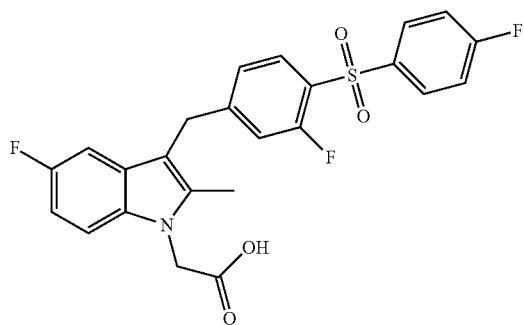 [SMILES: Cc1c(Cc2ccc(S(=O)(=O)c3ccc(F)cc3)c(F)c2)c2cc(F)ccc2n1CC(=O)O]

Preparation 3a: 3-fluoro-4-(4-fluorophenylsulfanyl)benzaldehyde

A mixture of 4-fluorobenzenethiol (0.93 g), potassium carbonate (3.1 g) and N,N-dimethylformamide (25 mL) was treated with 3,4-difluorobenzaldehyde (1.0 g), and the resulting mixture was stirred at room temperature for 16 hours. The mixture was partitioned between water and ethyl acetate, and the organic phase was dried over magnesium sulfate. The solvent was removed under reduced pressure to afford the title compound as a colourless gum (0.18 g).

$^1$H NMR (CDCl$_3$): δ 6.90 (t, J=7.6 Hz, 1H), 7.15 (t, J=8.6 Hz, 2H), 7.45-7.58 (m, 4H), 9.88 (d, J=1.9 Hz, 1H).

Preparation 3b: 3-fluoro-4-(4-fluorobenzenesulfonyl)benzaldehyde

The title compound was prepared by the method of Preparation 1b using 3-fluoro-4-(4-fluorophenylsulfanyl)benzaldehyde.

$^1$H NMR (CDCl$_3$): δ 7.23 (d, J=8.5 Hz, 2H), 7.62 (dd, J=1.4, 9.5 Hz, 1H), 7.84 (dd, J=1.4, 8.0 Hz, 1H), 8.03-8.09 (m, 2H), 8.30 (t, J=7.3 Hz, 1H), 10.04 (d, J=1.8 Hz, 1H).

Preparation 3c: {5-fluoro-3-[3-fluoro-4-(4-fluorobenzenesulfonyl)benzyl]-2-methylindol-1-yl}acetic acid methyl ester The title compound was prepared by the method of Preparation 1c using (5-fluoro-2-methylindol-1-yl)acetic acid methyl ester and 3-fluoro-4-(4-fluorobenzenesulfonyl)benzaldehyde.

$^1$H NMR (CDCl$_3$): δ 2.29 (s, 3H), 3.74 (s, 3H), 4.05 (s, 2H), 4.76-4.80 (m, 2H), 6.82-6.94 (m, 3H), 7.05-7.08 (m, 1H), 7.10-7.20 (m, 3H), 9.91-8.02 (m, 3H).

Preparation 3d: {5-fluoro-3-[3-fluoro-4-(4-fluorobenzenesulfonyl)benzyl]-2-methylindol-1-yl}acetic acid A mixture of {5-fluoro-3-[3-fluoro-4-(4-fluorobenzenesulfonyl)benzyl]-2-methylindol-1-yl}acetic acid methyl ester (0.14 g) and tetrahydrofuran (1.0 mL) was treated with 5.0 M aqueous sodium hydroxide solution (2.0 mL), and the resulting mixture was stirred at 40° C. for 1 hour. The mixture was acidified by the addition of 5.0 M aqueous hydrochloric acid solution and concentrated under reduced pressure. The residue was purified by preparative reverse-phase HPLC, eluting with a mixture of acetonitrile and water (3.5:6.5 to 9:1, by volume) to afford the title compound as a white solid (0.046 g).

$^1$H NMR (DMSO-d$_6$): δ 2.30 (s, 3H), 4.11 (s, 2H), 4.94 (s, 2H), 6.87 (td, J=2.5, 9.2 Hz, 1H), 7.16-7.23 (m, 2H), 7.30 (dd, J=1.5, 8.2 Hz, 1H), 7.36 (dd, J=4.4, 8.9 Hz, 1H), 7.42-7.49 (m, 2H), 7.90-8.02 (m, 3H), 13.10 (br s, 1H).

MS: ESI (+ve) (Method A): 473 (M+H)$^+$, Retention time 11.4 min.

Example 4

{3-[2-(4-chlorobenzenesulfonyl)pyridin-3-ylmethyl]-5-fluoro-2-methylindol-1-yl}acetic acid

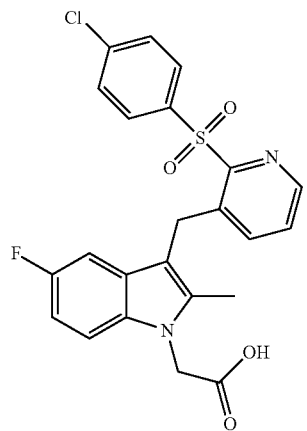 [SMILES: Cc1c(Cc2cccnc2S(=O)(=O)c2ccc(Cl)cc2)c2cc(F)ccc2n1CC(=O)O]

Preparation 4a:
2-(4-chlorobenzenesulfonyl)pyridine-3-carbaldehyde

The title compound was prepared by the method of Preparation 1b using 2-(4-chlorophenylsulfanyl)pyridine-3-carbaldehyde.

$^1$H NMR (CDCl$_3$): δ 7.55-7.64 (m, 3H), 7.98-8.03 (m, 2H), 8.40 (dd, J=1.8, 7.9 Hz, 1H), 8.69 (dd, J=1.7, 4.7 Hz, 1H), 11.13 (d, J=0.8 Hz, 1H).

Preparation 4b: {3-[2-(4-chlorobenzenesulfonyl)pyridin-3-ylmethyl]-5-fluoro-2-methylindol-1-yl}acetic acid methyl ester The title compound was prepared by the method of Preparation 1c using (5-fluoro-2-methylindol-1-yl)acetic acid methyl ester and 2-(4-chlorobenzenesulfonyl)pyridine-3-carbaldehyde.

$^1$H NMR (CDCl$_3$): δ 2.31 (s, 3H), 3.77 (s, 3H), 4.64 (s, 2H), 4.83 (s, 2H), 6.80-6.94 (m, 2H), 7.11 (dd, J=4.2, 8.8 Hz, 1H), 7.22 (dd, J=4.6, 7.9 Hz, 1H), 7.36-7.40 (m, 1H), 7.54-7.59 (m, 2H), 7.98-8.03 (m, 2H), 8.30 (dd, J=1.6, 4.6 Hz, 1H).

Preparation 4c: {3-[2-(4-chlorobenzenesulfonyl)pyridin-3-ylmethyl]-5-fluoro-2-methylindol-1-yl}acetic acid A mixture of {3-[2-(4-chlorobenzenesulfonyl)pyridin-3-ylmethyl]-5-fluoro-2-methylindol-1-yl}acetic acid methyl ester (0.19 g) and tetrahydrofuran (1.5 mL) was treated with 5.0 M aqueous sodium hydroxide solution (2.0 mL), and the resulting mixture was stirred at 40° C. for 3 hours. The mixture was acidified by the addition of 5.0 M aqueous hydrochloric acid solution and concentrated under reduced pressure. The residue was purified by preparative reverse-phase HPLC, eluting with a mixture of acetonitrile and water (3.5:6.5 to 9:1 by volume) to afford the title compound as a white solid (0.039 g).

$^1$H NMR (DMSO-d$_6$): δ 2.30 (s, 3H), 4.57 (s, 2H), 4.98 (s, 2H), 6.85-6.92 (m, 2H), 7.37-7.50 (m, 3H), 7.74-7.79 (m, 2H), 8.00-8.04 (m, 2H), 8.37 (dd, J=1.7, 4.4 Hz, 1H), 13.00 (br s, 1H).

MS: ESI (+ve) (Method A): 473 (M+H)$^+$, Retention time 11.1 min.

Example 5

{5-fluoro-3-[3-(4-fluorobenzenesulfonyl)pyridin-4-ylmethyl]-2-methylindol-1-yl}acetic acid

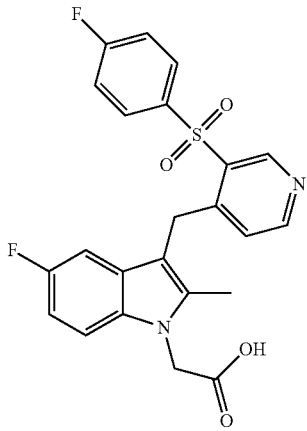 [SMILES: Cc1c(Cc2ccncc2S(=O)(=O)c2ccc(F)cc2)c2cc(F)ccc2n1CC(=O)O]

Preparation 5a:
3-(4-fluorobenzenesulfonyl)pyridine-4-carbaldehyde

A solution of 3-fluoroisonicotinaldehyde (0.25 mL) in dimethyl sulfoxide (2.0 mL) was treated with a solution of 4-fluorobenzene sulfinic acid sodium salt (0.5 g) in dimethyl sulfoxide (3.0 mL), and the resulting mixture was stirred at 100° C. for 3 days. The mixture was cooled to room temperature, partitioned between water and ethyl acetate (20 mL), and the aqueous phase extracted with ethyl acetate. The combined organic solution was dried over sodium sulfate and concentrated under reduced pressure. The residue was purified by column chromatography on silica gel, eluting with a mixture of dichloromethane and ethyl acetate (1:0 to 4:1 by volume) to afford the title compound as a white solid (0.38 g).

$^1$H NMR (CDCl$_3$): δ 7.24-7.29 (m, 2H), 7.76 (dd, J=0.7, 4.9 Hz, 1H), 7.95-8.01 (m, 2H), 9.02 (d, J=4.9 Hz, 1H), 9.30 (s, 1H), 10.88 (d, J=0.7 Hz, 1H).

Preparation 5b: {5-fluoro-3-[3-(4-fluorobenzenesulfonyl)pyridin-4-ylmethyl]-2-methylindol-1-yl}acetic acid methyl ester The title compound was prepared by the method of Preparation 1c using (5-fluoro-2-methylindol-1-yl)acetic acid methyl ester and 3-(4-fluorobenzenesulfonyl)pyridine-4-carbaldehyde.

$^1$H NMR (CDCl$_3$): δ 2.16 (s, 3H), 3.76 (s, 3H), 4.25 (s, 2H), 4.79 (s, 2H), 6.34 (dd, J=2.5, 9.3 Hz, 1H), 6.82-6.90 (m, 2H), 7.08 (dd, J=4.1, 8.9 Hz, 1H), 7.28 (dd, J=2.0, 8.3 Hz, 2H), 8.02 (dd, J=5.0, 8.9 Hz, 2H), 8.55 (d, J=5.1 Hz, 1H), 9.32 (s, 1H).

Preparation 5c: {5-fluoro-3-[3-(4-fluorobenzenesulfonyl)pyridin-4-ylmethyl]-2-methylindol-1-yl}acetic acid A mixture of {5-fluoro-3-[3-(4-fluorobenzenesulfonyl)pyridin-4-ylmethyl]-2-methylindol-1-yl}acetic acid methyl ester (0.21 g) and tetrahydrofuran (1.0 mL) was treated with 5.0 M aqueous sodium hydroxide solution (3.0 mL), and the resulting mixture was stirred at 40° C. for 3 hours. The mixture was acidified by the addition of 5.0 M aqueous hydrochloric acid solution and concentrated to low bulk under reduced pressure. The resulting precipitate was collected by filtration, washed with water and dried to afford the title compound as a white solid (0.094 g).

$^1$H NMR (DMSO-d$_6$): δ 2.11 (s, 3H), 4.21 (s, 2H), 4.97 (s, 2H), 6.25 (dd, J=2.5, 9.8 Hz, 1H), 6.84 (td, J=2.5, 9.2 Hz, 1H), 6.90 (d, J=5.2 Hz, 1H), 7.37 (dd, J=4.4, 8.9 Hz, 1H), 7.47-7.56 (m, 2H), 8.13-8.19 (m, 2H), 8.66 (d, J=5.1 Hz, 1H), 9.27 (s, 1H), 13.05 (br s, 1H).

MS: ESI (+ve) (Method A): 457 (M+H)$^+$, Retention time 10.1 min.

Example 6

(5-fluoro-3-{2-[(4-fluorophenyl)methylsulfamoyl]benzyl}-2-methylindol-1-yl)acetic acid

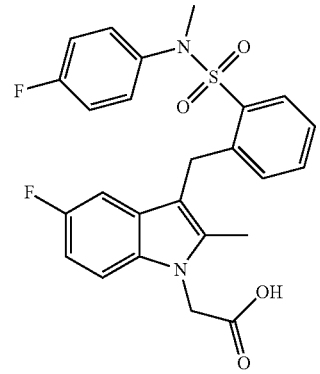 [SMILES: Cc1c(Cc2ccccc2S(=O)(=O)N(C)c2ccc(F)cc2)c2cc(F)ccc2n1CC(=O)O]

Preparation 6a: 2-[(4-fluorophenyl)methylsulfamoyl]benzoic acid methyl ester A solution of 4-fluoro-N-methylaniline (0.53 g), triethylamine (0.65 g) and dichloromethane (2.0 mL) was treated with 2-chlorosulfonylbenzoic acid methyl ester (1.0 g), and the resulting mixture was stirred at room temperature for 24 hours. The mixture was partitioned between water and dichloromethane, and the organic phase was washed with saturated aqueous sodium chloride solution and dried over sodium sulfate. The solvent was removed under reduced pressure and the residue was purified by column chromatography on SCX-2, eluting with methanol and then 2.0 M ammonia in methanol to afford the title compound as a pale yellow solid (1.2 g).

$^1$H NMR (CDCl$_3$): δ 3.26 (s, 3H), 3.86 (s, 3H), 6.96-7.04 (m, 2H), 7.11-7.18 (m, 2H), 7.36-7.49 (m, 3H), 7.58 (ddd, J=1.7, 6.8, 7.7 Hz, 1H).

Preparation 6b: N-(4-fluorophenyl)-2-hydroxymethyl-N-methylbenzenesulfonamide A solution of 2-[(4-fluorophenyl)methylsulfamoyl]benzoic acid methyl ester (0.80 g) in tetrahydrofuran at −20° C. was treated dropwise with 1.0 M lithium aluminium hydride solution in tetrahydrofuran (2.5 mL), and the resulting mixture was stirred at −20° C. for 3 hours. The mixture was treated with 1.0 M aqueous hydrochloric acid solution and Rochelle's salt, and the resulting mixture was stirred at room temperature for 1 hour. The mixture was extracted with ethyl acetate and the combined organic extract was dried over sodium sulfate and concentrated under reduced pressure. The residue was purified by column chromatography on silica gel, eluting with a mixture of cyclohexane and ethyl acetate (1:0 to 6:4 by volume) to afford the title compound as colourless oil (0.35 g).

$^1$H NMR (CDCl$_3$): δ 3.21 (s, 3H), 4.38 (d, J=6.6 Hz, 2H), 6.95-7.12 (m, 4H), 7.44 (ddd, J=1.9, 7.0, 7.9 Hz, 1H), 7.53-7.63 (m, 2H), 7.79 (dd, J=1.3, 7.9 Hz, 1H).

Preparation 6c: N-(4-fluorophenyl)-2-formyl-N-methylbenzenesulfonamide

A solution of N-(4-fluorophenyl)-2-hydroxymethyl-N-methylbenzenesulfonamide (0.35 g) in chloroform (20 mL) was treated with manganese dioxide (1.2 g), and the resulting mixture was stirred at 60° C. for 16 hours. The mixture was filtered through Celite and the filtrate concentrated under reduced pressure to afford the title compound as colourless oil (0.23 g).

$^1$H NMR (CDCl$_3$): δ 3.18 (s, 3H), 6.96-7.08 (m, 4H), 7.68-7.75 (m, 2H), 7.88-7.94 (m, 1H), 8.00-8.06 (m, 1H), 9.99 (s, 1H).

Preparation 6d: (5-fluoro-3-{2-[(4-fluorophenyl)methylsulfamoyl]benzyl}-2-methylindol-1-yl)acetic acid methyl ester The title compound was prepared by the method of Preparation 1c using (5-fluoro-2-methylindol-1-yl)acetic acid methyl ester and N-(4-fluorophenyl)-2-formyl-N-methylbenzenesulfonamide.

$^1$H NMR (CDCl$_3$): δ 2.20 (s, 3H), 3.29 (s, 3H), 3.75 (s, 3H), 4.17 (s, 2H), 4.80 (s, 2H), 6.78-6.92 (m, 2H), 6.93-7.11 (m, 4H), 7.21-7.25 (m, 1H), 7.25-7.35 (m, 3H), 7.89 (dd, J=1.8, 7.6 Hz, 1H).

Preparation 6e: (5-fluoro-3-{2-[(4-fluorophenyl)methylsulfamoyl]benzyl}-2-methylindol-1-yl)acetic acid A mixture of (5-fluoro-3-{2-[(4-fluorophenyl)methylsulfamoyl]benzyl}-2-methylindol-1-yl)acetic acid methyl ester (0.22 g) and tetrahydrofuran (1.0 mL) was treated with 5.0 M aqueous sodium hydroxide solution (3.0 mL), and the resulting mixture was stirred at 40° C. for 3 hours. The mixture was acidified by the addition of 5.0 M aqueous hydrochloric acid solution and concentrated under reduced pressure. The residue was purified by preparative reverse-phase HPLC, eluting with a mixture of acetonitrile and water (3.5:6.5 to 9:1 by volume) to afford the title compound as a white solid (0.10 g).

$^1$H NMR (DMSO-d$_6$): δ 2.17 (s, 3H), 3.25 (s, 3H), 4.03 (s, 2H), 4.97 (s, 2H), 6.76-6.93 (m, 3H), 7.20-7.28 (m, 2H), 7.31-7.40 (m, 4H), 7.45 (td, J=1.5, 7.5 Hz, 1H), 7.82 (dd, J=1.4, 7.9 Hz, 1H), 13.02 (br s, 1H).

MS: ESI (+ve) (Method A): 485 (M+H)$^+$, Retention time 11.7 min.

Example 7

{5-fluoro-3-[3-(4-fluorobenzenesulfonyl)pyridin-2-ylmethyl]-2-methylindol-1-yl}acetic acid

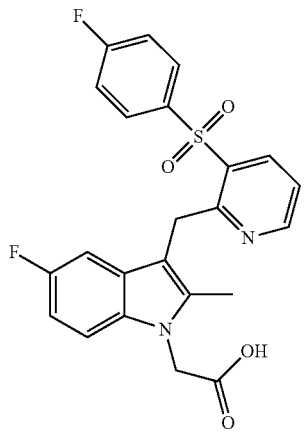 [SMILES: Cc1c(Cc2ncccc2S(=O)(=O)c2ccc(F)cc2)c2cc(F)ccc2n1CC(=O)O]

Preparation 7a: 3-(4-fluorobenzenesulfonyl)pyridine-2-carbaldehyde

A mixture of 3-fluoropyridine-2-carbaldehyde (0.70 g), 4-fluorobenzenesulfinic acid sodium salt (1.1 g) and dimethyl sulfoxide (7.0 mL) was stirred at 100° C. for 18 hours. The mixture was cooled to room temperature, diluted with water (20 mL), and the resulting precipitate was removed by filtration. The filtrate was extracted with ethyl acetate, and the combined organic extract was washed with saturated aqueous sodium chloride solution and dried over magnesium sulfate. The solvent was removed under reduced pressure to afford the title compound as a pale yellow oil (0.67 g).

$^1$H NMR (CDCl$_3$): δ 7.23 (m, 2H), 7.22 (dd, J=4.7, 8.0 Hz, 1H), 8.03 (m, 2H), 8.63 (ddd, J=0.3, 1.5, 8.0 Hz, 1H), 8.97 (dd, J=1.5, 4.7 Hz, 1H), 10.36 (s, 1H).

Preparation 7b: {5-fluoro-3-[3-(4-fluorobenzene-sulfonyl)pyridin-2-ylmethyl]-2-methylindol-1-yl}acetic acid methyl ester The title compound was prepared by the method of Preparation 1c using (5-fluoro-2-methylindol-1-yl)acetic acid methyl ester and 3-(4-fluorobenzenesulfonyl)pyridine-2-carbaldehyde.

$^1$H NMR (CDCl$_3$): δ 2.26 (s, 3H), 3.75 (s, 3H), 4.45 (s, 2H), 4.74 (s, 2H), 6.32 (dd, J=2.5, 9.8 Hz, 1H), 6.78 (dt, J=2.5, 9.0 Hz, 1H), 6.98 (m, 1H), 7.12 (m, 2H), 7.37 (m, 1H), 7.83 (m, 2H), 8.51 (dd, J=1.7, 8.0 Hz, 1H), 8.68 (dd, J=1.7, 4.8 Hz, 1H).

MS: ESI (+ve) (Method B): 471 (M+H)$^+$, Retention time 3.7 min.

Preparation 7c: {5-fluoro-3-[3-(4-fluorobenzene-sulfonyl)pyridin-2-ylmethyl]-2-methylindol-1-yl}acetic acid A solution of {5-fluoro-3-[3-(4-fluorobenzenesulfonyl)pyridin-2-ylmethyl]-2-methylindol-1-yl}acetic acid methyl ester (0.18 g) in tetrahydrofuran (5.0 mL) was treated with 1.0 M aqueous lithium hydroxide solution (0.45 mL), and the resulting mixture was stirred at room temperature for 1 hour. The mixture was concentrated under reduced pressure, pH adjusted to 4 by the addition of 0.1 M aqueous hydrochloric acid solution and extracted with ethyl acetate. The combined organic extract was washed with saturated aqueous sodium chloride solution, dried over magnesium sulfate and concentrated under reduced pressure. The residue was purified by preparative reverse-phase HPLC, eluting with a mixture of acetonitrile and water (1:19 to 49:1 by volume) to afford the title compound as a white solid (0.13 g).

$^1$H NMR (DMSO-d$_6$): δ 2.15 (s, 3H), 4.36 (s, 2H), 4.88 (s, 2H), 6.21 (dd, J=2.5, 10.1 Hz, 1H), 6.75 (dt, J=2.5, 9.1 Hz, 1H), 7.25 (m, 1H), 7.40 (t, J=8.8 Hz, 2H), 7.58 (m, 1H), 7.96 (m, 2H), 8.53 (dd, J=1.6, 8.1 Hz, 1H), 8.70 (dd, J=1.6, 4.7 Hz, 1H), 13.05 (br s, 1H).

MS: ESI (+ve) (Method A): 457 (M+H)$^+$, Retention time 10.1 min.

Example 8

{5-fluoro-3-[3-fluoro-2-(4-fluorobenzenesulfonyl)benzyl]-2-methylindol-1-yl}acetic acid

Preparation 8a: 3-fluoro-2-(4-fluorophenylsulfanyl)benzaldehyde

The title compound was prepared by the method of Preparation 3a using 2,3-difluorobenzaldehyde.

$^1$H NMR (CDCl$_3$): δ 6.92-7.01 (m, 2H), 7.20-7.27 (m, 2H), 7.38 (td, J=1, 5, 8.3 Hz, 1H), 7.48-7.56 (m, 1H), 7.81 (ddd, J=0.7, 1.5, 7.7 Hz, 1H), 10.70 (d, J=0.8 Hz, 1H).

Preparation 8b: 3-fluoro-2-(4-fluorobenzenesulfonyl)benzaldehyde

The title compound was prepared by the method of Preparation 1b using 3-fluoro-2-(4-fluorophenylsulfanyl)benzaldehyde.

$^1$H NMR (CDCl$_3$): δ 7.20-7.35 (m, 3H), 7.63-7.73 (m, 2H), 8.07 (ddd, J=1.6, 5.0, 8.9 Hz, 2H), 11.00 (d, J=0.7 Hz, 1H).

Preparation 8c: {5-fluoro-3-[3-fluoro-2-(4-fluorobenzenesulfonyl)benzyl]-2-methylindol-1-yl}acetic acid methyl ester The title compound was prepared by the method of Preparation 1c using (5-fluoro-2-methylindol-1-yl)acetic acid methyl ester and 2-benzenesulfonyl-3-fluorobenzaldehyde.

$^1$H NMR (CDCl$_3$): δ 2.30 (s, 3H), 3.77 (s, 3H), 4.68 (s, 2H), 4.84 (s, 2H), 6.66 (dd, J=2.5, 9.5 Hz, 1H), 6.82-6.98 (m, 3H), 7.10 (dd, J=4.2, 8.7 Hz, 1H), 7.18 (m, 2H), 7.31 (td, J=5.5, 7.9 Hz, 1H), 7.98 (ddd, J=1.4, 5.1, 8.8 Hz, 2H).

Preparation 8d: {5-fluoro-3-[3-fluoro-2-(4-fluorobenzenesulfonyl)benzyl]-2-methylindol-1-yl}acetic acid The title compound was prepared by the method of Preparation 2d using {5-fluoro-3-[3-fluoro-2-(4-fluorobenzenesulfonyl)benzyl]-2-methylindol-1-yl}acetic acid methyl ester.

$^1$H NMR (DMSO-d$_6$): δ 2.23 (s, 3H), 4.60 (s, 2H), 5.00 (s, 2H), 6.70 (dd, J=2.4, 9.6 Hz, 1H), 6.84-6.89 (m, 2H), 7.24 (dd, J=8.3, 10.9 Hz, 1H), 7.39 (dd, J=4.5, 8.9 Hz, 1H), 7.46 (m, 2H), 7.53 (ddd, J=1.4, 5.1, 8.8 Hz, 1H), 8.04 (dd, J=5.1, 8.3 Hz, 2H), 13.06 (br s, 1H).

MS: ESI (+ve) (Method A): 474 (M+H)$^+$, Retention time 11.4 min.

Example 9

[3-(3-benzenesulfonylthiophen-2-ylmethyl)-5-fluoro-2-methylindol-1-yl]acetic acid

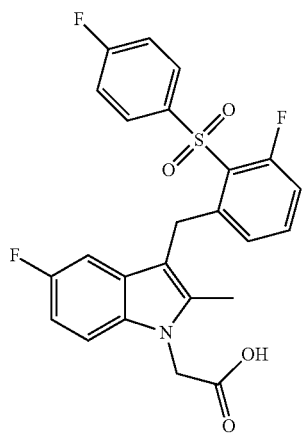 [SMILES: Cc1c(Cc2cccc(F)c2S(=O)(=O)c2ccc(F)cc2)c2cc(F)ccc2n1CC(=O)O]

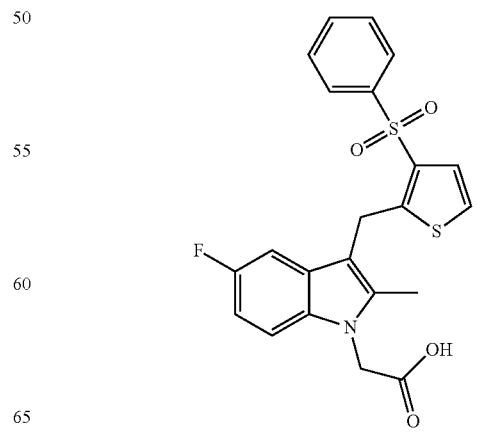

Preparation 9a: 3-phenylsulfanylthiophene-2-carbaldehyde

The title compound was prepared by the method of Preparation 1a using benzenethiol and 3-bromothiophene-2-carbaldehyde.

$^1$H NMR (CDCl$_3$): δ 6.81 (d, J=5.07 Hz, 1H), 7.32-7.38 (m, 3H), 7.40-7.44 (m, 2H), 7.63 (dt, J=1.0, 5.0 Hz, 1H), 10.13 (d, J=1.2 Hz, 1H).

Preparation 9b: 3-benzenesulfonylthiophene-2-carbaldehyde

The title compound was prepared by the method of Preparation 1b using 3-phenylsulfanylthiophene-2-carbaldehyde $^1$H NMR (CDCl$_3$): δ 7.49 (d, J=5.2 Hz, 1H), 7.54-7.61 (m, 2H), 7.62-7.68 (m, 1H), 7.70 (dd, J=1.2, 5.2 Hz, 1H), 7.95-8.00 (m, 2H), 10.64 (d, J=1.2 Hz, 1H).

MS: ESI (+ve) (Method B): 253 (M+H)$^+$, Retention time 3.2 min.

Preparation 9c: [3-(3-benzenesulfonylthiophen-2-ylmethyl)-5-fluoro-2-methylindol-1-yl]acetic acid methyl ester The title compound was prepared by the method of Preparation 1c using (5-fluoro-2-methylindol-1-yl)acetic acid methyl ester and 3-benzenesulfonylthiophene-2-carbaldehyde.

$^1$H NMR (DMSO-d$_6$): δ 2.20 (s, 3H), 3.67 (s, 3H), 4.45 (s, 2H), 5.12 (s, 2H), 6.69 (dd, J=2.5, 9.8 Hz, 1H), 6.87 (dt, J=2.5, 9.2 Hz, 1H), 7.35-7.41 (m, 2H), 7.44 (d, J=5.4 Hz, 1H), 7.65-7.79 (m, 3H), 8.03-8.07 (m, 2H).

MS: ESI (+ve) (Method B): 458 (M+H)$^+$, Retention time 3.9 min.

Preparation 9d: [3-(3-benzenesulfonylthiophen-2-ylmethyl)-5-fluoro-2-methylindol-1-yl]acetic acid A solution of [3-(3-benzenesulfonylthiophen-2-ylmethyl)-5-fluoro-2-methylindol-1-yl]acetic acid methyl ester (0.19 g) in tetrahydrofuran (10 mL) was treated with 1.0 M aqueous lithium hydroxide solution (0.8 mL), and the resulting mixture was stirred at room temperature for 1 hour. The mixture was concentrated under reduced pressure, pH adjusted to 4 by the addition of 0.1 M aqueous hydrochloric acid solution and extracted with ethyl acetate. The combined organic extract was washed with saturated aqueous sodium chloride solution, dried over magnesium sulfate and concentrated under reduced pressure. The residue was purified by preparative reverse-phase HPLC, eluting with a mixture of acetonitrile and water (1:19 to 49:1 by volume) to afford the title compound as a white solid (0.17 g).

$^1$H NMR (DMSO-d$_6$): δ 2.14 (s, 3H), 4.38 (s, 2H), 4.88 (s, 2H), 6.61 (dd, J=2.5, 9.8 Hz, 1H), 6.80 (dt, J=2.5, 9.2 Hz, 1H), 7.30 (dd, J=4.3, 8.8 Hz, 1H), 7.33 (d, J=5.5 Hz, 1H), 7.37 (d, J=5.5 Hz, 1H), 7.60-7.64 (m, 2H), 7.67-7.72 (m, 1H), 7.97-7.99 (m, 2H), 13.02 (br s, 1H).

MS: ESI (+ve) (Method A): 444 (M+H)$^+$, Retention time 10.7 min.

Example 10

[3-(2-benzenesulfonylpyridin-3-ylmethyl)-5-fluoro-2-methylindol-1-yl]acetic acid

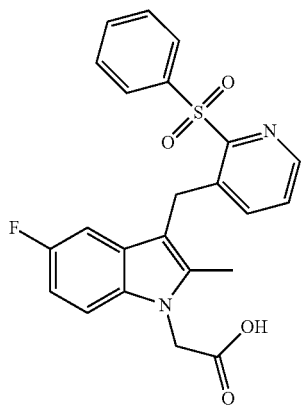 [SMILES: Cc1c(Cc2cccnc2S(=O)(=O)c2ccccc2)c2cc(F)ccc2n1CC(=O)O]

Preparation 10a: 2-benzenesulfonylpyridine-3-carbaldehyde

The title compound was prepared by the method of Preparation 1b using 2-phenylsulfanylpyridine-3-carbaldehyde $^1$H NMR (DMSO-d$_6$): δ 7.62-7.73 (m, 2H), 7.78-7.88 (m, 2H), 8.03-8.08 (m, 2H), 8.33 (dd, J=1.7, 7.7 Hz, 1H), 8.82 (dd, J=1.7, 4.7 Hz, 1H), 10.90 (d, J=0.7 Hz, 1H).

Preparation 10b: [3-(2-benzenesulfonylpyridin-3-ylmethyl)-5-fluoro-2-methylindol-1-yl]acetic acid methyl ester The title compound was prepared by the method of Preparation 1c using 2-benzenesulfonylpyridine-3-carbaldehyde and (5-fluoro-2-methylindol-1-yl)acetic acid methyl ester.

$^1$H NMR (CDCl$_3$): δ 2.28 (s, 3H), 3.77 (s, 3H), 4.60 (s, 2H), 4.82 (s, 2H), 6.71 (dd, J=2.4, 9.4 Hz, 1H), 6.88 (dt, J=2.4, 9.0 Hz, 1H), 7.10 (dd, J=4.1, 8.8 Hz, 1H), 7.21 (dd, J=4.5, 7.9 Hz, 1H), 7.33-7.37 (m, 1H), 7.56-7.63 (m, 2H), 7.66-7.72 (m, 1H), 8.07-8.11 (m, 2H), 8.36 (m 1H).

MS: ESI (+ve) (Method B): 453 (M+H)$^+$, Retention time 3.8 min.

Preparation 10c: [3-(2-benzenesulfonylpyridin-3-ylmethyl)-5-fluoro-2-methylindol-1-yl]acetic acid A mixture of [3-(2-benzenesulfonylpyridin-3-ylmethyl)-5-fluoro-2-methylindol-1-yl]acetic acid methyl ester (0.16 g) and tetrahydrofuran (5.0 mL) was treated with 1.0 M aqueous lithium hydroxide solution (0.5 mL), and the resulting mixture was stirred at room temperature for 30 minutes. The mixture was concentrated under reduced pressure, pH adjusted to 4 by the addition of 0.1 M aqueous hydrochloric acid solution and extracted with ethyl acetate. The combined organic extract was washed with saturated aqueous sodium chloride solution, dried over magnesium sulfate and concentrated under reduced pressure. The residue was purified by preparative reverse-phase HPLC, eluting with a mixture of acetonitrile and water (5:95 to 98:2 by volume) to afford the title compound as a white solid (0.11 g).

¹H NMR (DMSO-d₆): δ 2.26 (s, 3H), 4.55 (s, 2H), 4.94 (s, 2H), 6.86-6.89 (m, 2H), 7.35-7.42 (m, 2H), 7.45 (dd, J=4.4, 8.9 Hz, 1H), 7.68-7.72 (m, 2H), 7.79 (tt, J=1.2, 7.5 Hz, 1H), 8.00-8.02 (m, 2H), 8.36 (dd, J=1.5, 4.4 Hz, 1H), 13.2 (br s, 1H).

MS: ESI (+ve) (Method A): 439 (M+H)⁺, Retention time 10.1 min.

Example 11

[3-(3-benzenesulfonylpyridin-2-ylmethyl)-5-fluoro-2-methylindol-1-yl]acetic acid

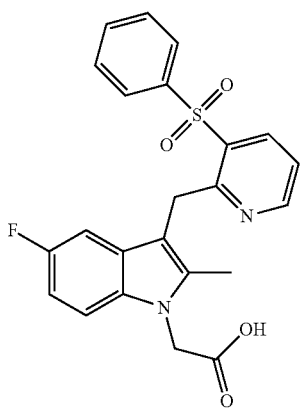 [SMILES: Cc1c(Cc2ncccc2S(=O)(=O)c2ccccc2)c2cc(F)ccc2n1CC(=O)O]

Preparation 11a:
3-benzenesulfonylpyridine-2-carbaldehyde

The title compound was prepared by the method of Preparation 5a using 3-fluoropyridine-2-carbaldehyde and benzene sulfinic acid sodium salt.

¹H NMR (DMSO-d₆): δ 7.62-7.73 (m, 2H), 7.72-7.79 (m, 1H), 7.95 (dd, J=4.7, 8.1 Hz, 1H), 8.01-8.06 (m, 2H), 8.67 (dd, J=1.4, 8.1 Hz, 1H), 9.05 (dd, J=1.4, 4.7 Hz, 1H), 10.36 (s, 1 H).

Preparation 11b: [3-(3-benzenesulfonylpyridin-2-ylmethyl)-5-fluoro-2-methylindol-1-yl]acetic acid methyl ester The title compound was prepared by the method of Preparation 1c using 3-benzenesulfonylpyridine-2-carbaldehyde and (5-fluoro-2-methylindol-1-yl)acetic acid methyl ester.

¹H NMR (CDCl₃): δ 2.22 (s, 3H), 3.73 (s, 3H), 4.41 (s, 2H), 4.71 (s, 2H), 6.31 (dd, J=2.5, 9.7 Hz, 1H), 6.76 (dt, J=2.5, 9.2 Hz, 1H), 6.97 (dd, J=4.2, 8.8 Hz, 1H), 7.31-7.38 (m, 1H), 7.46-7.53 (m, 2H), 7.56-7.63 (m, 1H), 7.84-7.89 (m, 2H), 8.52 (dd, J=1.7, 8.0 Hz, 1H), 8.63 (dd, J=1.7, 4.7 Hz, 1H).

MS: ESI (+ve) (Method B): 453 (M+H)⁺, Retention time 3.7 min.

Preparation 11c: [3-(3-benzenesulfonylpyridin-2-ylmethyl)-5-fluoro-2-methylindol-1-yl]acetic acid A mixture of [3-(3-benzenesulfonylpyridin-2-ylmethyl)-5-fluoro-2-methylindol-1-yl]acetic acid methyl ester (0.19 g) and tetrahydrofuran (5.0 mL) was treated with 1.0 M aqueous lithium hydroxide solution (0.62 mL), and the resulting mixture was stirred at room temperature for 30 minutes. The mixture was concentrated under reduced pressure, pH adjusted to 4 by the addition of 0.1 M aqueous hydrochloric acid solution and extracted with ethyl acetate. The combined organic extract was washed with saturated aqueous sodium chloride solution, dried over magnesium sulfate and concentrated under reduced pressure. The residue was purified by preparative reverse-phase HPLC, eluting with a mixture of acetonitrile and water (1:19 to 49:1 by volume) to afford the title compound as a white solid (0.15 g).

¹H NMR (DMSO-d₆): δ 2.10 (s, 3H), 4.33 (s, 2H), 4.88 (s, 2H), 6.33 (dd, J=2.5, 10.1 Hz, 1H), 6.75 (dt, J=2.5, 9.2 Hz, 1H), 7.24 (dd, J=4.4, 8.9 Hz, 1H), 7.56 (dd, J=4.7, 8.0 Hz, 1H), 7.60-7.64 (m, 2H), 7.71-7.73 (m, 1H), 7.91-7.94 (m, 2H), 8.53 (dd, J=1.7, 8.0 Hz, 1H), 8.67 (dd, J=1.7, 4.7 Hz, 1H) 13.01 (br s, 1H).

MS: ESI (+ve) (Method A): 439 (M+H)⁺, Retention time 9.9 min.

Example 12

{5-fluoro-2-methyl-3-[2-(thiophene-2-sulfonyl)benzyl]indol-1-yl}acetic acid

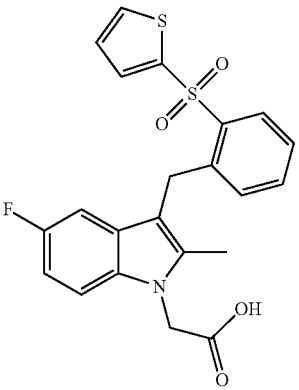 [SMILES: Cc1c(Cc2ccccc2S(=O)(=O)c2cccs2)c2cc(F)ccc2n1CC(=O)O]

Preparation 12a:
2-(thiophen-2-ylsulfanyl)benzaldehyde

A mixture of thiophene-2-thiol (1.5 mL), potassium carbonate (8.0 g) and N,N-dimethylformamide was treated dropwise with 2-fluorobenzaldehyde (1.7 mL), and the resulting mixture was stirred at room temperature for 42 hours. The mixture was treated with ice/water, extracted with ethyl acetate and the combined organic extract was dried over magnesium sulfate. The solvent was removed under reduced pressure and the residue purified by column chromatography on silica gel, eluting with a mixture of cyclohexane and ethyl acetate (1:0 to 9:1 by volume), followed by distillation at 50° C./11 mbar to afford the title compound as a red oil (1.9 g).

¹H NMR (CDCl₃): δ 6.97 (d, J=8.1 Hz, 1H), 7.16 (dd, J=3.6, 5.4 Hz, 1H), 7.29 (ddd, J=1.1, 7.5, 7.5 Hz, 1H), 7.34 (dd, J=1.3, 3.6 Hz, 1H), 7.40 (ddd, J=1.7, 7.3, 8.1 Hz, 1H), 7.59 (dd, J=1.2, 5.3 Hz, 1H), 7.82 (dd, J=1.6, 7.5 Hz, 1H), 10.27 (s, 1H).

MS: ESI (+ve) (Method B): Retention time 3.8 min.

Preparation 12b:
2-(thiophene-2-sulfonyl)benzaldehyde

A mixture of 2-(thiophen-2-ylsulfanyl)benzaldehyde (0.30 g) and dichloromethane (13 mL) was treated portion wise with 3-chloroperoxybenzoic acid (67% in water, 0.70 g), and the resulting mixture was stirred at room temperature for 1 hour. The mixture was diluted with dichloromethane (150 mL), washed with saturated aqueous sodium bicarbonate solution and dried over magnesium sulfate. The solvent was removed under reduced pressure to afford the title compound as a yellow solid (0.29 g).

$^1$H NMR (CDCl$_3$): δ 7.13 (dd, J=4.9, 3.9 Hz, 1H), 7.71-7.80 (m, 4H), 8.05 (m, 1H), 8.18 (m, 1H), 11.01 (d, J=0.6 Hz, 1H).

MS: ESI (+ve) (Method B): Retention time 3.3 min.

Preparation 12c: {5-fluoro-2-methyl-3-[2-(thiophene-2-sulfonyl)benzyl]indol-1-yl}acetic acid methyl ester The title compound was prepared by the method of Preparation 1c using 2-(thiophene-2-sulfonyl)benzaldehyde and (5-fluoro-2-methylindol-1-yl)acetic acid methyl ester.

$^1$H NMR (CDCl$_3$): δ 2.21 (s, 3H), 3.76 (s, 3H), 4.42 (s, 2H), 4.81 (s, 2H), 6.43 (dd, J=2.4, 9.5 Hz, 1H), 6.85 (dd, J=2.5, 9.0 Hz, 1H), 6.96 (m, 1H), 7.07 (dd, J=4.1, 8.9 Hz, 1H), 7.13 (dd, J=3.8, 5.0 Hz, 1H), 7.37 (m, 2H), 7.71 (dd, J=1.3, 5.1 Hz, 1H), 7.78 (dd, J=1.3, 3.8 Hz, 1H), 8.24 (m, 1H).

MS: ESI (+ve) (Method B): 458 (M+H)$^+$, Retention time 4.0 min.

Preparation 12d: {5-fluoro-2-methyl-3-[2-(thiophene-2-sulfonyl)benzyl]indol-1-yl}acetic acid A mixture of {5-fluoro-2-methyl-3-[2-(thiophene-2-sulfonyl)benzyl]indol-1-yl}acetic acid methyl ester (0.21 g) and tetrahydrofuran (5.0 mL) was treated with 1.0 M aqueous lithium hydroxide solution (1.2 mL), and the resulting mixture was stirred at room temperature for 2 hours. The mixture was diluted with water (25 mL), concentrated to low bulk under reduced pressure and the pH adjusted to 4 by the addition of 0.1 M aqueous hydrochloric acid solution. The mixture was extracted with ethyl acetate and the combined organic extract was washed with saturated aqueous sodium chloride solution and dried over magnesium sulfate. The solvent was removed under reduced pressure and the residue purified by column chromatography on silica gel, eluting with a mixture of dichloromethane and ethyl acetate containing 0.1% formic acid (1:0 to 0:1 by volume), followed by preparative reverse-phase HPLC, eluting with a mixture of acetonitrile and water (3:7 to 9:1 by volume) to afford the title compound as a white solid (0.14 g).

$^1$H NMR (DMSO-d$_6$): δ 2.10 (s, 3H), 4.30 (s, 2H), 4.92 (s, 2H), 6.39 (dd, J=2.6, 9.7 Hz, 1H), 6.79 (ddd, J=2.3, 9.3, 9.3 Hz, 1H), 6.88 (dd, J=2.4, 6.9 Hz, 1H), 7.23 (dd, J=3.7, 4.8 Hz, 1H), 7.32 (dd, J=4.4, 8.8 Hz, 1H), 7.41-7.49 (m, 2H), 7.89 (dd, J=1.3, 4.0 Hz, 1H), 8.08-8.12 (m, 2H), 13.00 (s, 1H).

MS: ESI (+ve) (Method A): 444 (M+H)$^+$, Retention time 10.9 min.

Example 13

{5-fluoro-2-methyl-3-[3-(thiophene-2-sulfonyl)thiophen-2-ylmethyl]indol-1-yl}acetic acid

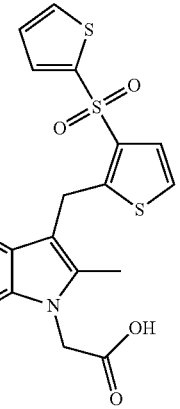

Preparation 13a:
3-(thiophen-2-ylsulfanyl)thiophene-2-carbaldehyde

A mixture of 3-chlorothiophene-2-carbaldehyde (1.0 g), potassium carbonate (2.8 g) and N,N-dimethylformamide (6.8 mL) was treated dropwise with thiophene-2-thiol (0.87 g), and the resulting mixture was stirred at room temperature for 3 hours. The mixture was poured onto water (150 mL) and extracted with diethyl ether. The combined organic extract was washed with saturated aqueous sodium hydrogen carbonate solution and saturated aqueous sodium chloride solution, and then dried over magnesium sulfate. The solvent was removed under reduced pressure to afford the title compound as a red oil (1.5 g).

$^1$H NMR (CDCl$_3$): δ 6.72 (d, J=5.3 Hz, 1H), 7.09 (dd, J=3.5, 5.6 Hz, 1H), 7.34 (dd, J=1.3, 3.5 Hz, 1H), 7.52 (dd, J=1.3, 5.3 Hz, 1H), 7.58 (dd, J=0.9, 5.2 Hz, 1H), 10.09 (d, J=1.0 Hz, 1H).

MS: ESI (+ve) (Method B): Retention time 3.6 min.

Preparation 13b:
3-(thiophene-2-sulfonyl)thiophene-2-carbaldehyde

A mixture of 3-(thiophen-2-ylsulfanyl)thiophene-2-carbaldehyde (1.5 g) and dichloromethane (68 mL) was treated with 3-chloroperoxybenzoic acid (70% in water, 4.6 g), and the resulting mixture was stirred at room temperature for 18 hours. The mixture was diluted with saturated aqueous sodium thiosulfate solution (50 mL), extracted with diethyl ether and the combined organic extract was washed with saturated aqueous sodium bicarbonate solution and saturated aqueous sodium chloride solution, and then dried over magnesium sulfate. The solvent was removed under reduced pressure to afford the title compound as a brown solid (1.2 g).

$^1$H NMR (CDCl$_3$): δ 7.15 (dd, J=3.8, 5.1 Hz, 1H), 7.53 (d, J=5.3 Hz, 1H), 7.70 (dd, J=1.3, 5.1 Hz, 1 H), 7.75 (dd, J=1.3, 4.8 Hz, 1H), 7.77 (dd, J=1.4, 3.8 Hz, 1H), 10.66 (d, J=1.3 Hz).

MS: ESI (+ve) (Method B): Retention time 3.3 min.

Preparation 13c: {5-fluoro-2-methyl-3-[3-(thiophene-2-sulfonyl)thiophen-2-ylmethyl]indol-1-yl}acetic acid methyl ester A mixture of (5-fluoro-2-methylindol-1-yl)acetic acid methyl ester (0.14 g), 3-(thiophene-2-sulfonyl)thiophene-2-carbaldehyde (0.12 g) and dichloroethane (5.0 mL) at 0° C. was treated dropwise with a mixture of triethylsilane (1.4 mL), trifluoroacetic acid (0.35 mL) and dichloroethane (2.0 mL), and the resulting mixture was stirred at room temperature for 1 hour. The mixture was cooled to 0° C., diluted with saturated aqueous sodium hydrogen carbonate solution and the phases separated. The aqueous phase was extracted with dichloromethane and the combined organic solution was dried over magnesium sulfate and concentrated under reduced pressure. The residue was purified by column chromatography on silica gel, eluting with a mixture of cyclohexane and ethyl acetate (1:0 to 1:1 by volume), to afford the title compound as a yellow solid (0.17 g).

$^1$H NMR (DMSO-$d_6$): δ 2.23 (s, 3H), 3.68 (s, 3H), 4.50 (s, 2H), 5.12 (s, 2H), 6.83 (dd, J=2.5, 9.7 Hz, 1H), 6.89 (ddd, J=2.5, 9.2, 9.2 Hz, 1H), 7.28 (dd, J=3.8, 4.9 Hz, 1H), 7.36 (d, J=5.6 Hz, 1H), 7.39 (dd, J=4.3, 9.0 Hz, 1H), 7.44 (d, J=5.6 Hz, 1H), 7.95 (dd, J=1.5, 3.8 Hz, 1H), 8.13 (dd, J=1.5, 4.8 Hz, 1H).

MS: ESI (+ve) (Method B): 464 (M+H)$^+$, Retention time 3.9 min.

Preparation 13d: {5-fluoro-2-methyl-3-[3-(thiophene-2-sulfonyl)thiophen-2-ylmethyl]indol-1-yl}acetic acid A mixture of {5-fluoro-2-methyl-3-[3-(thiophene-2-sulfonyl)thiophen-2-ylmethyl]indol-1-yl}acetic acid methyl ester (0.17 g), tetrahydrofuran (0.35 mL) and water (0.35 mL) was treated with lithium hydroxide (0.088 g), and the resulting mixture was stirred at room temperature for 1 hour. The mixture was cooled to 0° C., pH adjusted to 5 by the addition of 1.0 M aqueous hydrochloric acid solution and extracted with ethyl acetate. The combined organic extract was washed with saturated aqueous sodium chloride solution, dried over magnesium sulfate and concentrated under reduced pressure. The residue was purified by preparative reverse-phase HPLC, eluting with a mixture of acetonitrile and water (3:7 to 9:1 by volume) to afford the title compound as a white solid (0.089 g).

$^1$H NMR (DMSO-$d_6$): δ 2.19 (s, 3H), 4.46 (s, 2H), 4.93 (s, 2H), 6.77 (dd, J=2.6, 9.8 Hz, 1H), 6.83 (ddd, J=2.5, 9.2, 9.2 Hz, 1H), 7.24 (dd, J=4.0, 4.8 Hz), 7.31 (d, J=5.5 Hz), 7.34 (dd, J=4.4, 4.4 Hz), 7.39 (d, J=5.4 Hz, 1H), 7.91 (dd, J=1.3, 3.5 Hz, 1H), 8.09 (dd, J=1.3, 4.9 Hz, 1H), 12.96 (br s, 1H).

MS: ESI (+ve) (Method A): 450 (M+H)$^+$, Retention time 10.7 min.

Example 14

[3-(2-benzenesulfonyl-4-chlorobenzyl)-5-fluoro-2-methylindol-1-yl]acetic acid

Preparation 14a:
2-benzenesulfonyl-4-chlorobenzaldehyde

The title compound was prepared by the method of Preparation 5a using 4-chloro-2-fluorobenzaldehyde and benzene sulfinic acid sodium salt.

$^1$H NMR (CDCl$_3$): δ 7.54-7.61 (m, 2H), 7.62-7.71 (m, 2H), 7.89-7.93 (m, 2H), 7.98 (d, J=8.3 Hz, 1H), 8.18 (d, J=2.0 Hz, 1H), 10.79 (d, J=0.8 Hz, 1H).

Preparation 14b: [3-(2-benzenesulfonyl-4-chlorobenzyl)-5-fluoro-2-methylindol-1-yl]acetic acid methyl ester The title compound was prepared by the method of Preparation 1c using 2-benzenesulfonyl-4-chlorobenzaldehyde and (5-fluoro-2-methylindol-1-yl)acetic acid methyl ester.

$^1$H NMR (DMSO-$d_6$): δ 2.04 (s, 3H), 3.67 (s, 3H), 4.11 (s, 2H), 5.08 (s, 2H), 6.18 (dd, J=2.5, 9.8 Hz, 1H), 6.79-6.88 (m, 2H), 7.35 (dd, J=4.4, 8.9 Hz, 1H), 7.59-7.72 (m, 3H), 7.78 (d, J=7.3 Hz, 1H), 8.01-8.06 (m, 2H), 8.21 (d, J=2.3 Hz, 1H).

MS: ESI (+ve) (Method B): 486 (M+H)$^+$, Retention time 4.2 min.

Preparation 14c: [3-(2-benzenesulfonyl-4-chlorobenzyl)-5-fluoro-2-methylindol-1-yl]acetic acid A solution of [3-(2-benzenesulfonyl-4-chlorobenzyl)-5-fluoro-2-methylindol-1-yl]acetic acid methyl ester (0.16 g) in tetrahydrofuran (5.0 mL) was treated with 1.0 M aqueous lithium hydroxide solution (0.5 mL), and the resulting mixture was stirred at room temperature for 1 hour. The mixture was concentrated under reduced pressure, pH adjusted to 4 by the addition of 0.1 M aqueous hydrochloric acid solution and extracted with ethyl acetate. The combined organic extract was washed with saturated aqueous sodium chloride solution, dried over magnesium sulfate and concentrated under reduced pressure. The residue was purified by preparative reverse-phase HPLC, eluting with a mixture of acetonitrile and water (1:19 to 49:1 by volume) to afford the title compound as a white solid (0.15 g).

$^1$H NMR (DMSO-$d_6$): δ 2.04 (s, 3H), 4.10 (s, 2H), 4.92 (s, 2H), 6.18 (dd, J=2.5, 9.7 Hz, 1H), 6.81 (dt, J=2.5, 9.2 Hz, 1H), 6.87 (d, J=8.4 Hz, 1H), 7.34 (dd, J=4.4, 8.9 Hz, 1H), 7.61 (dd, J=2.4, 8.4 Hz, 1H), 7.67-7.71 (m, 2H), 7.77-7.80 (m, 1H), 8.02-8.05 (m, 2H), 8.20 (d, J=2.4 Hz, 1H) 13.04 (br s, 1H).

MS: ESI (+ve) (Method A): 472 (M+H)$^+$, Retention time 12.0 min.

Example 15

[3-(2-benzenesulfonyl-4-cyanobenzyl)-5-fluoro-2-methylindol-1-yl]acetic acid

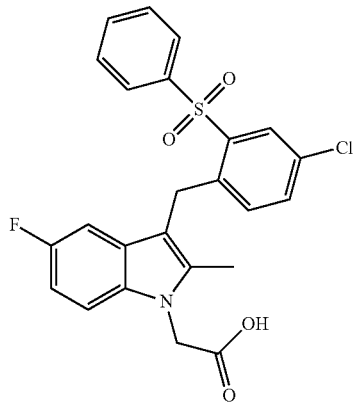 [SMILES: Cc1c(Cc2ccc(Cl)cc2S(=O)(=O)c2ccccc2)c2cc(F)ccc2n1CC(=O)O]

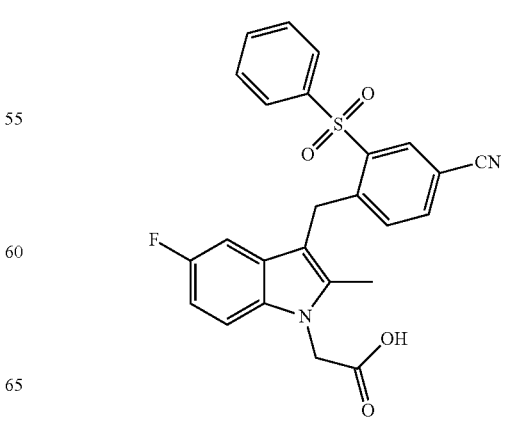

Preparation 15a: 3-benzenesulfonyl-4-formylbenzonitrile

The title compound was prepared by the method of Preparation 5a using 3-fluoro-2-phenylsulfanylbenzaldehyde.
$^1$H NMR (CDCl$_3$): δ 7.74-7.58 (m, 3H), 7.91-8.01 (m, 3H), 8.11 (d, J=8.0 Hz, 1H), 8.42 (d, J=1.6 Hz, 1H), 10.89 (d, J=0.8 Hz, 1H).

Preparation 15b: [3-(2-benzenesulfonyl-4-cyanobenzyl)-5-fluoro-2-methylindol-1-yl]acetic acid methyl ester The title compound was prepared by the method of Preparation 1c using 3-benzenesulfonyl-4-formylbenzonitrile and (5-fluoro-2-methylindol-1-yl)acetic acid methyl ester.
$^1$H NMR (DMSO-d$_6$): δ 2.02 (s, 3H), 3.65 (s, 3H), 4.19 (s, 2H), 5.07 (s, 2H), 6.17 (dd, J=2.6, 9.7 Hz, 1H), 6.83 (dt, J=2.4, 9.0 Hz, 1H), 7.01 (d, J=8.1 Hz, 1H), 7.36 (dd, J=4.4, 9.0 Hz, 1H), 7.70 (t, J=7.8 Hz, 2H), 7.79 (t, J=7.8 Hz, 1H), 8.00 (dd, J=1.9, 8.1 Hz, 1H), 8.07 (d, J=7.1 Hz, 2H), 8.61 (d, J=1.8 Hz, 1H).

Preparation 15c: [3-(2-benzenesulfonyl-4-cyanobenzyl)-5-fluoro-2-methylindol-1-yl]acetic acid A solution of [3-(2-benzenesulfonyl-4-cyanobenzyl)-5-fluoro-2-methylindol-1-yl]acetic acid methyl ester (0.11 g) in tetrahydrofuran (0.30 mL) was treated with 1.0 M aqueous lithium hydroxide solution (2.0 mL), and the resulting mixture was stirred at room temperature for 2 hours. The mixture was acidified by the addition of 1.0 M aqueous hydrochloric acid solution and concentrated under reduced pressure. The residue was purified by preparative reverse-phase HPLC, eluting with a mixture of acetonitrile and water (2:3 to 19:1 by volume) to afford the title compound as a white solid (0.058 g).
$^1$H NMR (DMSO-d$_6$): δ 2.04 (s, 3H), 4.21 (s, 2H), 4.93 (s, 2H), 6.16 (dd, J=2.5, 9.7 Hz, 1H), 6.82 (dt, J=2.5, 9.1 Hz, 1H), 7.03 (d, J=8.2 Hz, 1H), 7.35 (dd, J=4.4, 8.7 Hz, 1H), 7.69 (t, J=7.4 Hz, 2H), 7.80 (m, 1H), 7.98 (dd, J=1.8, 8.2 Hz, 1H), 8.08 (dd, J=1.5, 7.9 Hz, 2H), 8.62 (d, J=1.8 Hz, 1H), 13.03 (br s, 1H).
MS: ESI (+ve) (Method A): 463 (M+H)$^+$, Retention time 11.0 min.

Example 16

{5-fluoro-2-methyl-3-[3-(pyridine-2-sulfonyl)thiophen-2-ylmethyl]indol-1-yl}acetic acid

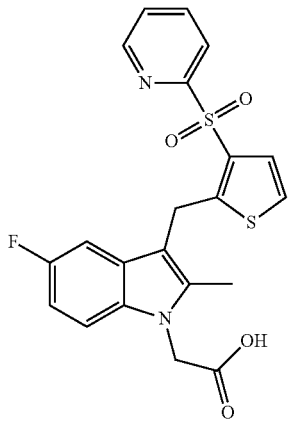 [SMILES: Cc1c(Cc2sccc2S(=O)(=O)c2ccccn2)c2cc(F)ccc2n1CC(=O)O]

Preparation 16a: 3-(pyridine-2-sulfonyl)thiophene-2-carbaldehyde

The title compound was prepared by the method of Preparation 5a using 2-formyl-3-chlorothiophene and pyridine-2-sulfinic acid sodium salt.
$^1$H NMR (CDCl$_3$): δ 7.52 (ddd, J=1.2, 4.6, 7.5 Hz, 1H), 7.58 (d, J=5.2 Hz, 1H), 7.69 (dd, J=1.2, 5.2 Hz, 1H), 7.98 (td, J=1.7, 7.8 Hz, 1H), 8.24 (dt, J=1.0, 7.9 Hz, 1H), 8.70 (ddd, J=0.9, 1.7, 4.7 Hz, 1H), 10.70 (d, J=1.2 Hz, 1H).

Preparation 16b: {5-fluoro-2-methyl-3-[3-(pyridine-2-sulfonyl)thiophen-2-ylmethyl]indol-1-yl}acetic acid methyl ester The title compound was prepared by the method of Preparation 1c using 3-(pyridine-2-sulfonyl)thiophene-2-carbaldehyde and (5-fluoro-2-methylindol-1-yl)acetic acid methyl ester.
$^1$H NMR (CDCl$_3$): δ 2.34 (s, 3H), 3.76 (s, 3H), 4.71 (s, 2H), 4.81 (s, 2H), 6.82-6.95 (m, 2H), 7.01-7.10 (m, 2H), 7.41 (d, J=5.4 Hz, 1H), 7.53 (ddd, J=1.2, 4.7, 7.7 Hz, 1H), 7.96 (td, J=1.8, 7.8 Hz, 1H), 8.21 (dt, J=1.0, 7.9 Hz, 1H), 8.79 (ddd, J=0.9, 1.7, 4.7 Hz, 1H).

Preparation 16c: {5-fluoro-2-methyl-3-[3-(pyridine-2-sulfonyl)thiophen-2-ylmethyl]indol-1-yl}acetic acid A solution of {5-fluoro-2-methyl-3-[3-(pyridine-2-sulfonyl)thiophen-2-ylmethyl]indol-1-yl}acetic acid methyl ester (0.050 g) in tetrahydrofuran (0.30 mL) was treated with 1.0 M aqueous lithium hydroxide solution (1.0 mL), and the resulting mixture was stirred at room temperature overnight. The mixture was treated with 5.0 M aqueous sodium hydroxide solution (1.0 mL) and stirred at room temperature for 3 hours and then at 40° C. overnight. The mixture was acidified by the addition of aqueous hydrochloric acid solution and concentrated under reduced pressure. The residue was purified by preparative reverse-phase HPLC, eluting with a mixture of acetonitrile and water (2:3 to 19:1 by volume) to afford the title compound as a yellow solid (0.020 g).
$^1$H NMR (DMSO-d$_6$): δ 2.20 (s, 3H), 4.50 (s, 2H), 4.89 (s, 2H), 6.82 (m, 2H), 7.27-7.33 (m, 2H), 7.37 (d, J=5.4 Hz, 1H), 7.71 (ddd, J=1.2, 4.7, 7.6 Hz, 1H), 8.13 (td, J=1.8, 7.8 Hz, 1H), 8.19 (dt, J=1.1, 7.7 Hz, 1H), 8.73 (ddd, J=0.9, 1.7, 4.7 Hz, 1H), 12.96 (br s, 1H).
MS: ESI (+ve) (Method A): 445 (M+H)$^+$, Retention time 9.9 min.

Example 17

{3-[4-(4-chlorobenzenesulfonyl)thiophen-3-ylmethyl]-5-fluoro-2-methylindol-1-yl}acetic acid

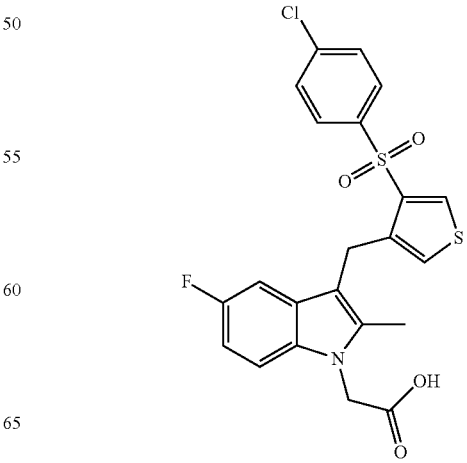

Preparation 17a: 4-(4-chlorophenylsulfanyl)thiophene-3-carboxylic acid methyl ester A mixture of 4-(4-chlorophenylsulfanyl)thiophene-3-carboxylic acid (1.0 g), sodium hydrogen carbonate (1.6 g), iodomethane (2.3 mL) and N,N-dimethylformamide (10 mL) was stirred was stirred at 40° C. for 5 hours. The mixture was cooled to room temperature, diluted with water (100 mL) and the aqueous phase extracted with ethyl acetate. The combined organic extract was dried over magnesium sulfate and concentrated under reduced pressure to afford the title compound as a yellow oil (1.0 g).
$^1$H NMR (DMSO-$d_6$): δ 3.77 (d, J=0.6 Hz, 3H), 6.96 (dd, J=0.6, 3.4 Hz, 1H), 7.41-7.52 (m, 4H), 8.49 (dd, J=0.6, 3.4 Hz, 1H).

Preparation 17b: 4-(4-chlorobenzenesulfonyl)thiophene-3-carboxylic acid methyl ester The title compound was prepared by the method of Preparation 1b using 4-(4-chlorophenylsulfanyl)thiophene-3-carboxylic acid methyl ester.
$^1$H NMR (DMSO-$d_6$): δ 3.7 (d, J=0.5 Hz, 3H), 7.67-7.73 (m, 2H), 7.88-7.93 (m, 2H), 8.45 (dd, J=0.5, 3.4 Hz, 1H), 8.74 (dd, J=0.5, 3.4 Hz, 1H).

Preparation 17c: [4-(4-chlorobenzenesulfonyl)thiophen-3-yl]methanol

The title compound was prepared by the method of Preparation 6b using 4-(4-chlorobenzenesulfonyl)thiophene-3-carboxylic acid methyl ester.
$^1$H NMR (CDCl$_3$): δ 4.62 (d, J=6.3 Hz, 2H), 4.69 (s, 1H), 7.37 (d, J=3.5 Hz, 1H), 7.48-7.54 (m, 2H), 7.85-7.91 (m, 2H), 8.19 (d, J=3.4 Hz, 1H).

Preparation 17d: 4-(4-chlorobenzenesulfonyl)thiophene-3-carbaldehyde

The title compound was prepared by the method of Preparation 6c using [4-(4-chlorobenzenesulfonyl)thiophen-3-yl]methanol.
$^1$H NMR (DMSO-$d_6$): δ 7.67-7.73 (m, 2H), 7.97-8.02 (m, 2H), 8.69-8.72 (m, 2H), 9.96 (s, 1H).

Preparation 17e: {3-[4-(4-chlorobenzenesulfonyl)thiophen-3-ylmethyl]-5-fluoro-2-methylindol-1-yl}acetic acid methyl ester The title compound was prepared by the method of Preparation 1c using 4-(4-chloro-benzenesulfonyl)thiophene-3-carbaldehyde and (5-fluoro-2-methylindol-1-yl)acetic acid methyl ester.
MS: ESI (+ve) (Method B): 492 (M+H)$^+$, Retention time 4.1 min.

Preparation 17f: {3-[4-(4-chlorobenzenesulfonyl)thiophen-3-ylmethyl]-5-fluoro-2-methylindol-1-yl}acetic acid A mixture of {3-[4-(4-chlorobenzenesulfonyl)thiophen-3-ylmethyl]-5-fluoro-2-methylindol-1-yl}acetic acid methyl ester (0.35 g) and tetrahydrofuran (5.0 mL) was treated with 1.0 M aqueous lithium hydroxide solution (1.0 mL), and the resulting mixture was stirred at room temperature for 1 hour. The mixture was concentrated under reduced pressure, pH adjusted to 4 by the addition of 0.1 M aqueous hydrochloric acid solution and extracted with ethyl acetate. The combined organic extract was washed with saturated aqueous sodium chloride solution, dried over magnesium sulfate and concentrated under reduced pressure. The residue was purified by preparative reverse-phase HPLC, eluting with a mixture of acetonitrile and water (1:19 to 49:1 by volume) to afford the title compound as a white solid (0.30 g).
$^1$H NMR (DMSO-$d_6$): δ 2.13 (s, 3H), 3.94 (s, 2H), 4.89 (s, 2H), 6.35 (dd, J=2.5, 9.8 Hz, 1H), 6.80 (dt, J=2.5, 9.2 Hz, 1H), 6.96 (d, J=3.3 Hz, 1H), 7.28 (dd, J=4.4, 8.9 Hz, 1H), 7.57-7.60 (m, 2H), 7.77-7.80 (m, 2H), 8.60 (d, J=3.3 Hz, 1H), 13.0 (br s, 1H).
MS: ESI (+ve) (Method A): 478 (M+H)$^+$, Retention time 11.4 min.

Example 18

[3-(4-benzenesulfonylthiophen-3-ylmethyl)-5-fluoro-2-methylindol-1-yl]acetic acid

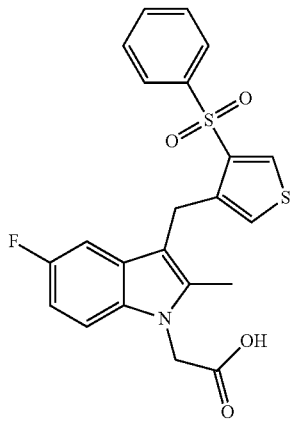 [SMILES: Cc1c(Cc2cscc2S(=O)(=O)c2ccccc2)c2cc(F)ccc2n1CC(=O)O]

Preparation 18a: [3-(4-benzenesulfonylthiophen-3-ylmethyl)-5-fluoro-2-methylindol-1-yl]acetic acid A mixture of {3-[4-(4-chlorobenzenesulfonyl)thiophen-3-ylmethyl]-5-fluoro-2-methylindol-1-yl}acetic acid (0.031 g), triethylamine (0.300 mL), palladium on charcoal (0.012 g) and ethanol (5.0 mL) was stirred under an atmosphere of hydrogen at 40° C. for 15 hours. The mixture was filtered through Celite and the filtrate concentrated under reduced pressure. The residue was purified by preparative reverse-phase HPLC, eluting with a mixture of acetonitrile and water (1:19 to 49:1 by volume) to afford the title compound as a pale yellow solid (0.024 g).
$^1$H NMR (DMSO-$d_6$): δ 2.07 (s, 3H), 3.89 (s, 2H), 4.80 (s, 2H), 6.39 (dd, J=2.5, 9.8 Hz, 1H), 6.77-6.82 (m, 2H), 7.28 (dd, J=4.4, 8.8 Hz, 1H), 7.61-7.65 (m, 2H), 7.70-7.74 (m, 1H), 7.89-7.92 (m, 2H), 8.56 (d, J=3.4 Hz, 1H), 13.0 (br s, 1H).

MS: ESI (+ve) (Method A): 444 (M+H)+, Retention time 10.8 min.

Example 19

[5-fluoro-3-(2-benzenesulfonylthiophen-3-ylmethyl)-2-methylindol-1-yl]acetic acid

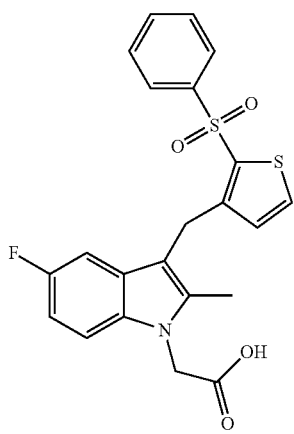 [SMILES: Cc1c(Cc2ccsc2S(=O)(=O)c2ccccc2)c2cc(F)ccc2n1CC(=O)O]

Preparation 19a: [5-fluoro-3-(2-benzenesulfonylthiophen-3-ylmethyl)-2-methylindol-1-yl]acetic acid methyl ester The title compound was prepared by the method of Preparation 1c using 2-phenylsulfonylthiophene-3-carbaldehyde and (5-fluoro-2-methylindol-1-yl)acetic acid methyl ester.

$^1$H NMR (CDCl$_3$): δ 2.20 (s, 3H), 3.74 (s, 3H), 4.16 (s, 2H), 4.75 (s, 2H), 6.49 (dd, J=2.5, 9.5 Hz, 1H), 6.57 (d, J=5.3 Hz, 1H), 6.82 (td, J=2.5, 9.9 Hz, 1H), 7.03 (dd, J=4.2, 9.0 Hz, 1H), 7.39 (d, J=5.0 Hz, 1H), 7.52-7.57 (m, 2H), 7.59-7.64 (m, 1H), 8.01-8.05 (m, 2H).

MS: ESI (+ve) (Method B): 458 (M+H)+, Retention time 3.9 min.

Preparation 19b: [5-fluoro-3-(2-benzenesulfonylthiophen-3-ylmethyl)-2-methylindol-1-yl]acetic acid A mixture of [5-fluoro-3-(2-benzenesulfonylthiophen-3-ylmethyl)-2-methylindol-1-yl]acetic acid methyl ester (0.18 g), tetrahydrofuran (4.0 mL) and methanol (2.0 mL) was treated with 1.0 M aqueous sodium hydroxide solution (2.0 mL), and the resulting mixture was stirred at room temperature for 1 hour. The mixture was acidified by the addition of 1.0 M aqueous hydrochloric acid solution and concentrated to low bulk under reduced pressure. The resulting precipitate was collected by filtration, washed with water and dried to afford the title compound as a white solid (0.16 g).

$^1$H NMR (DMSO-d$_6$): δ 2.11 (s, 3H), 4.09 (s, 2H), 4.88 (s, 2H), 6.51-6.56 (m, 2H), 6.78 (td, J=2.6, 9.2 Hz, 1H), 7.28 (dd, J=4.4, 8.9 Hz, 1H), 7.59-7.65 (m, 2H), 7.67-7.73 (m, 1H), 7.82 (d, J=5.2 Hz, 1H), 7.94-7.98 (m, 2H), 12.95 (br s, 1H).

MS: ESI (+ve) (Method A): 444 (M+H)+, Retention time 10.9 min.

Example 20

[5-fluoro-2-methyl-3-(2-phenylsulfamoylbenzyl)indol-1-yl]acetic acid

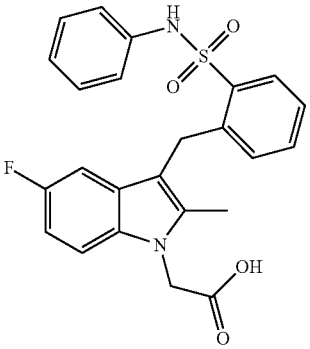 [SMILES: Cc1c(Cc2ccccc2S(=O)(=O)Nc2ccccc2)c2cc(F)ccc2n1CC(=O)O]

Preparation 20a: [5-fluoro-2-methyl-3-(2-sulfobenzyl)indol-1-yl]acetic acid methyl ester A mixture of (5-fluoro-2-methylindol-1-yl)acetic acid methyl ester (1.0 g), 2-formylbenzensulfonic acid sodium salt (0.94 g) and 1,2-dichloroethane (15 mL) at 0° C. was treated dropwise with a mixture of triethylsilane (4.3 mL), trifluoroacetic acid (1.0 mL) and 1,2-dichloroethane (10 mL), and the resulting mixture was stirred at room temperature for 6 hours. The mixture was extracted with ethyl acetate and the combined organic extract was dried over sodium sulfate. The solvent was removed under reduced pressure and the residue purified by column chromatography on silica gel, eluting with a mixture of methanol and dichloromethane (0:1 to 1:9 by volume) to afford the title compound as a purple gum (1.3 g).

Preparation 20b: [3-(2-chlorosulfonylbenzyl)-5-fluoro-2-methylindol-1-yl]acetic acid methyl ester A mixture of [5-fluoro-2-methyl-3-(2-sulfobenzyl)indol-1-yl]acetic acid methyl ester (0.30 g) and dichloromethane (1.5 mL) was treated portion wise with phosphorus pentachloride (0.15 g), followed by N,N-dimethylformamide (0.070 mL), and the resulting mixture was heated at reflux overnight. The mixture was cooled to room temperature, concentrated under reduced pressure and diluted with dichloromethane. The mixture was washed with water, dried over magnesium sulfate and concentrated under reduced pressure. The residue was purified by column chromatography on silica gel, eluting with dichloromethane to afford the title compound as a yellow solid (1.3 g).

MS: ESI (+ve) (Method B): 410 (M+H)+, Retention time 4.2 min.

Preparation 20c: [5-fluoro-2-methyl-3-(2-phenylsulfamoylbenzyl)indol-1-yl]acetic acid methyl ester A mixture of aniline (0.022 mL), triethylamine (0.051 mL) and dichloromethane (0.5 mL) was treated with [3-(2-chlorosulfonylbenzyl)-5-fluoro-2-methylindol-1-yl]acetic acid methyl ester (0.10 g), and resulting mixture was stirred at room temperature for 4 days. The mixture was diluted with dichloromethane, washed with water and concentrated under reduced pressure to afford the title compound as a colourless gum (0.078 g).

MS: ESI (+ve) (Method B): 467 (M+H)⁺, Retention time 4.1 min.

Preparation 20d: [5-fluoro-2-methyl-3-(2-phenylsulfamoylbenzyl)indol-1-yl]acetic acid A mixture of [3-(2-chlorosulfonylbenzyl)-5-fluoro-2-methylindol-1-yl]acetic acid methyl ester (0.078 g) and tetrahydrofuran (0.5 mL) was treated with 2.0 M aqueous sodium hydroxide solution (1.0 mL), and the resulting mixture was stirred at room temperature for 20 hours. The mixture was acidified by the addition of 2.0 M aqueous hydrochloric acid solution and concentrated under reduced pressure. The residue was purified by preparative reverse-phase HPLC, eluting with a mixture of acetonitrile and water (2:3 to 19:1 by volume) to afford the title compound as a white solid (0.055 g).
$^1$H NMR (DMSO-d$_6$): δ 2.21 (s, 3H), 4.41 (s, 2H), 4.97 (s, 2H), 6.75 (dd, J=2.5, 9.8 Hz, 1H), 6.82-6.89 (m, 2H), 7.02 (t, J=7.3 Hz, 1H), 7.16 (d, J=7.8 Hz, 2H), 7.25 (t, J=7.3 Hz, 2H), 7.29-7.40 (m, 3H), 7.97 (dd, J=1.8, 7.5 Hz, 1H), 10.60 (br s, 1H), 12.95 (br s, 1H).
MS: ESI (+ve) (Method A): 453 (M+H)⁺, Retention time 11.1 min.

Example 21

{5-fluoro-2-methyl-3-[2-(methylphenylsulfamoyl)benzyl]indol-1-yl}acetic acid

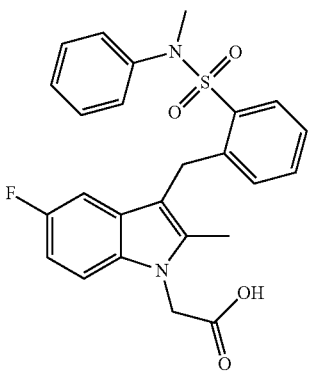 [SMILES: Cc1c(Cc2ccccc2S(=O)(=O)N(C)c2ccccc2)c2cc(F)ccc2n1CC(=O)O]

Preparation 21a: {5-fluoro-2-methyl-3-[2-(methylphenylsulfamoyl)benzyl]indol-1-yl}acetic acid methyl ester The title compound was prepared by the method of Preparation 20c using [3-(2-chlorosulfonylbenzyl)-5-fluoro-2-methylindol-1-yl]acetic acid methyl ester and N-methylaniline.
MS: ESI (+ve) (Method B): 481 (M+H)⁺, Retention time 4.2 min.

Preparation 21b: {5-fluoro-2-methyl-3-[2-(methylphenylsulfamoyl)benzyl]indol-1-yl}acetic acid A mixture of {5-fluoro-2-methyl-3-[2-(methylphenylsulfamoyl)benzyl]indol-1-yl}acetic acid methyl ester (0.10 g) and tetrahydrofuran (0.5 mL) was treated with 2.0 M aqueous sodium hydroxide solution (2.0 mL), and the resulting mixture was stirred at room temperature for 15 hours. The mixture was acidified by the addition of 2.0 M aqueous hydrochloric acid solution and concentrated under reduced pressure. The residue was purified by preparative reverse-phase HPLC, eluting with a mixture of acetonitrile and water (2:3 to 1:9 by volume) to afford the title compound as pale yellow solid (0.083 g).
$^1$HNMR (DMSO-d$_6$): δ 2.10 (s, 3H), 3.23 (s, 3H), 3.95 (s, 2H), 4.88 (s, 2H), 6.73 (dd, J=2.5, 9.9 Hz, 1H), 6.82 (td, J=2.2, 9.1 Hz, 1H), 6.85 (d, J=7.4 Hz, 1H), 7.32 (m, 8H), 7.79 (dd, J=2.0, 7.9 Hz, 1H).
MS: ESI (+ve) (Method A): 467 (M+H)⁺, Retention time 11.6 min.

Example 22

[5-fluoro-3-(4-phenylsulfonylpyridin-3-ylmethyl)-2-methylindol-1-yl]acetic acid

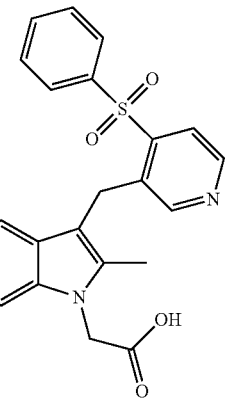

Preparation 22a: 4-phenylsulfonylpyridine-3-carbaldehyde

A mixture of 4-bromopyridine-3-carbaldehyde (0.90 g), benzenesulfinic acid sodium salt (4.0 g), copper (I) iodide (4.6 g) and 1-methyl-2-pyrrolidinone (50 mL) was heated at 60° C. for 2 hours. The mixture was cooled to room temperature, diluted with ethyl acetate and filtered through Celite. The filtrate was washed with water, dried over magnesium sulfate and concentrated under reduced pressure. The residue was purified by column chromatography on silica gel, eluting with a mixture of cyclohexane and ethyl acetate (1:0 to 0:1 by volume) to afford the title compound as a yellow oil (1.9 g).
$^1$H NMR (CDCl$_3$): δ 7.56-7.74 (m, 3H), 7.88-7.98 (m, 3H), 9.05 (s, 1H), 9.21 (s, 1H), 10.92 (s, 1H).

Preparation 22b: [5-fluoro-3-(4-phenylsulfonylpyridin-3-ylmethyl)-2-methylindol-1-yl]acetic acid methyl ester A mixture of triethylsilane (5.1 g), trifluoroacetic acid (3.1 g) and 1,2-dichloroethane (20 mL) at −10° C. was treated dropwise with a mixture of 4-phenylsulfonylpyridine-3-carbaldehyde (1.9 g), (5-fluoro-2-methylindol-1-yl)acetic acid methyl ester (0.66 g) and 1,2-dichloroethane (20 mL), and the resulting mixture was stirred at room temperature for 20 hours. The mixture was treated with additional triethylsilane (5.1 g) and trifluoroacetic acid (3.1 g), and stirred at room temperature for 3 hours and then at 50° C. for 20 hours. The mixture was diluted with dichloromethane, washed with saturated aqueous sodium hydrogen carbonate solution and dried over magnesium sulfate. The solvent was removed under reduced pressure and the residue was purified by column chromatography on silica gel, eluting with a mixture of cyclohexane and ethyl acetate (1:0 to 0:1 by volume), followed by trituration with diethyl ether to afford the title compound as a yellow powder (0.19 g).

$^1$H NMR (CDCl$_3$): δ 2.16 (s, 3H), 3.72 (s, 3H), 4.23 (s, 2H), 4.75 (s, 2H), 6.25 (dd, J=2.6, 9.3 Hz, 1H), 6.81 (dt, J=2.6, 8.9 Hz, 1H), 7.03 (dd, J=4.1, 8.9 Hz, 1H), 7.57 (t, J=7.8 Hz, 2H), 7.67 (t, J=7.5 Hz, 1H), 7.95 (d, J=7.6 Hz, 2H), 8.00 (d, J=5.0 Hz, 1H), 8.19 (s, 1H), 8.67 (d, J=5.0 Hz, 1H).

Preparation 22c: [5-fluoro-3-(4-phenylsulfonylpyridin-3-ylmethyl)-2-methylindol-1-yl]acetic acid A mixture of [5-fluoro-3-(4-phenylsulfonylpyridin-3-ylmethyl)-2-methylindol-1-yl]acetic acid methyl ester (0.19 g) and tetrahydrofuran (1.0 mL) was treated with 2.0 M aqueous sodium hydroxide solution (3.0 mL), and the resulting mixture was stirred at room temperature for 3 hours. The mixture was acidified by the addition of 1.0 M aqueous hydrochloric acid solution, and the resulting precipitate was collected by filtration to afford the title compound as a pale yellow powder (0.15 g).

$^1$H NMR (DMSO-d$_6$): δ 2.08 (s, 3H), 4.17 (s, 2H), 4.90 (s, 2H), 6.23 (dd, J=2.7, 9.8 Hz, 1H), 6.78 (td, J=2.6, 9.3 Hz, 1H), 7.31 (dd, J=4.5, 8.9 Hz, 1H), 7.65 (t, J=7.6 Hz, 2H), 7.76 (t, J=7.5 Hz, 1H), 7.96-8.01 (m, 3H), 8.08 (s, 1H), 8.71 (d, J=5.1 Hz, 1H), 12.91 (br s, 1H).

MS: ESI (+ve) (Method A): 439 (M+H)$^+$, Retention time 10.0 min.

Example 23

{5-fluoro-3-[3-(pyridine-3-sulfonyl)thiophen-2-ylmethyl]-2-methylindol-1-yl}acetic acid

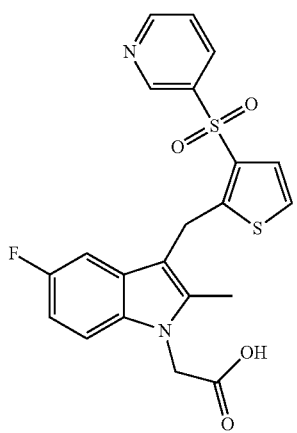 [SMILES: Cc1c(Cc2sccc2S(=O)(=O)c2cccnc2)c2cc(F)ccc2n1CC(=O)O]

Preparation 23a:
3-(pyridine-3-sulfonyl)thiophene-2-carbaldehyde

A mixture of 3-chlorothiophene-2-carbaldehyde (0.16 g), pyridine-3-sulfinic acid sodium salt (0.30 g) and dimethyl sulfoxide (2.0 mL) was heated at 80° C. for 3 hours and then at 90° C. for 3 hours. The mixture was diluted with water, extracted with ethyl acetate and the combined organic extract was dried over magnesium sulfate. The solvent was removed under reduced pressure to afford the title compound as a grey solid (0.079 g).

$^1$H NMR (CDCl$_3$): δ 7.50-7.57 (m, 2H), 7.75 (dd, J=1.2, 5.2 Hz, 1H), 8.23-8.28 (m, 1H), 8.88 (s, 1H), 9.20 (s, 1H), 10.64 (d, J=1.2 Hz, 1H).

Preparation 23b: {5-fluoro-3-[3-(pyridine-3-sulfonyl)thiophen-2-ylmethyl]-2-methylindol-1-yl}acetic acid methyl ester A mixture of triethylsilane (0.42 g), trifluoroacetic acid (0.25 g) and 1,2-dichloroethane (2.0 mL) at −10° C. was treated dropwise with a mixture of (5-fluoro-2-methylindol-1-yl)acetic acid methyl ester (0.055 g), 3-(pyridine-3-sulfonyl)thiophene-2-carbaldehyde (0.075 g) and 1,2-dichloroethane (2.0 mL), and the resulting mixture was stirred at room temperature for 20 hours. The mixture was treated with additional triethylsilane (0.42 g) and trifluoroacetic acid (0.25 g), and stirred at room temperature for 3 hours and then at 50° C. for 20 hours. The mixture was diluted with dichloromethane, washed with saturated aqueous sodium hydrogen carbonate solution and dried over magnesium sulfate. The solvent was removed under reduced pressure and the residue purified by column chromatography on silica gel, eluting with a mixture of diethyl ether and ethyl acetate (1:0 to 0:1 by volume), followed by trituration with diethyl ether to afford the title compound as a white solid (0.027 g).

$^1$H NMR (CDCl$_3$): δ 2.26 (s, 3H), 3.72 (s, 3H), 4.43 (s, 2H), 4.77 (s, 2H), 6.67 (dd, J=2.4, 6.9 Hz, 1H), 6.83 (dt, J=2.5, 9.0 Hz, 1H), 7.03 (dd, J=4.2, 8.8 Hz, 1H), 7.07 (d, J=5.7 Hz, 1H), 7.39-7.45 (m, 2H), 8.14-8.18 (m, 1H), 8.79 (d, J=4.5 Hz, 1H), 9.13 (s, 1H).

Preparation 23c: {5-fluoro-3-[3-(pyridine-3-sulfonyl)thiophen-2-ylmethyl]-2-methylindol-1-yl}acetic acid A mixture of {5-fluoro-3-[3-(pyridine-3-sulfonyl)thiophen-2-ylmethyl]-2-methylindol-1-yl}acetic acid methyl ester (0.025 g) and tetrahydrofuran (0.8 mL) was treated with 2.0 M aqueous sodium hydroxide solution (0.5 mL), and the resulting mixture was stirred at room temperature for 1 hour. The mixture was acidified by the addition of 1.0 M aqueous hydrochloric acid solution, extracted with ethyl acetate and the combined organic extract was dried over magnesium sulfate. The solvent was removed under reduced pressure and the residue triturated with diethyl ether to afford the title compound as a white solid (0.020 g).

$^1$H NMR (DMSO-d$_5$): δ 2.17 (s, 3H), 4.45 (s, 2H), 4.92 (s, 2H), 6.72 (dd, J=2.5, 9.8 Hz, 1H), 6.82 (td, J=2.6, 9.1 Hz, 1H), 7.32 (dd, J=4.4, 8.8 Hz, 1H), 7.40-7.44 (m, 2H), 7.63 (dd, J=4.8, 8.1 Hz, 1H), 8.35-8.39 (m, 1H), 8.85 (dd, J=1.8, 4.9 Hz, 1H), 9.13-9.16 (m, 1H), 12.98 (br s, 1H).

MS: ESI (+ve) (Method A): 445 (M+H)$^+$, Retention time 9.5 min.

Example 24

{5-fluoro-2-methyl-3-[3-(Pyridine-4-sulfonyl)thiophen-2-ylmethyl]indol-1-yl}acetic acid

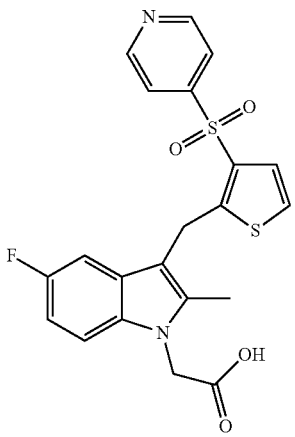 [SMILES: Cc1c(Cc2sccc2S(=O)(=O)c2ccncc2)c2cc(F)ccc2n1CC(=O)O]

Preparation of 24a: 3-(pyridin-4-ylsulfanyl)thiophene-2-carbaldehyde

A mixture of 4-mercaptopyridine (1.0 g), potassium carbonate (3.7 g) and dimethyl sulfoxide (10 mL) at 0° C. was treated with 3-chlorothiophene-2-carbaldehyde (1.3 g), and the resulting mixture was stirred at room temperature for 20 hours. The mixture was partitioned between ethyl acetate and water, and the organic phase was washed with water and dried over magnesium sulfate. The solvent was removed under reduced pressure and the residue purified by column chromatography on silica gel, eluting with a mixture of ethyl acetate and petroleum ether (1:9 to 3:2 by volume) to afford the title compound as yellow oil (1.3 g).
$^1$HNMR (CDCl$_3$) δ 7.01 (m, 2H), 7.16 (d, J=5.0 Hz, 1H), 7.85 (dd, J=1.3, 5.0 Hz, 1H), 8.44 (d, J=5.0 Hz, 2H), 10.12 (s, 1H).

Preparation of 24b: {5-fluoro-2-methyl-3-[3-(pyridin-4-ylsulfanyl)thiophen-2-ylmethyl]indol-1-yl}acetic acid methyl ester A mixture of 3-(pyridin-4-ylsulfanyl)thiophene-2-carbaldehyde (1.3 g), (5-fluoro-2-methylindol-1-yl)acetic acid methyl ester (1.3 g) and 1,2-dichloroethane (30 mL) at −10° C. was treated with a mixture of triethylsilane (5.8 mL), trifluoroacetic acid (2.4 mL) and 1,2-dichloroethane (20 mL), and the resulting mixture was stirred at room temperature for 48 hours. The mixture was diluted with dichloromethane, washed with aqueous sodium bicarbonate solution and concentrated under reduced pressure. The residue was purified by column chromatography on silica gel, eluting with ethyl acetate to afford the title compound as yellow foam (2.4 g).
$^1$HNMR (CDCl$_3$) δ 2.28 (s, 3H), 3.73 (s, 3H), 4.21 (s, 2H), 4.69 (s, 2H), 6.81 (dd, J=1.6, 4.5 Hz, 2H), 6.87 (m, 1H), 7.02 (m, 2H), 7.08 (dd, J=2.4, 9.5 Hz, 1H), 7.20 (d, J=5.3 Hz, 1H), 8.28 (dd, J=1.6, 4.6 Hz, 2H).

Preparation of 24c: {5-fluoro-2-methyl-3-[3-(pyridine-4-sulfonyl)thiophen-2-ylmethyl]indol-1-yl}acetic acid methyl ester A mixture of 5-fluoro-2-methyl-3-[3-(pyridin-4-ylsulfanyl)thiophen-2-ylmethyl]indol-1-yl}acetic acid methyl ester (0.20 g) and dichloromethane (2 mL) at 0° C. was treated dropwise with a solution of 3-chloroperoxybenzoic acid (0.16 g) in dichloromethane (0.5 mL), and the resulting mixture was stirred at room temperature for 18 hours. The mixture was cooled to 0° C., treated with additional 3-chloroperoxybenzoic acid (0.16 g) and stirred at 0° C. temperature for 1 hour. The mixture was partitioned between ethyl acetate and saturated aqueous sodium bicarbonate solution, and the aqueous phase was extracted with ethyl acetate. The combined organic phase was dried over sodium sulfate and concentrated under reduced pressure to afford a brown oil. The residue was purified by column chromatography on a silica gel, eluting with a mixture of dichloromethane and ethyl acetate (9:1 to 0:10 by volume). Further purification by preparative reverse-phase HPLC, eluting with a mixture acetonitrile and water (1:9 to 9:1 by volume) gave the title compound as a yellow solid (0.026 g).
MS: ESI (+ve) (Method B): 459 (M+H)$^+$, Retention time 2.4 min.

Preparation 24d: {5-fluoro-2-methyl-3-[3-(pyridine-4-sulfonyl)thiophen-2-ylmethyl]indol-1-yl}acetic acid A mixture of {5-fluoro-2-methyl-3-[3-(pyridine-4-sulfonyl)thiophen-2-ylmethyl]indol-1-yl}acetic acid methyl ester (0.026 g) and tetrahydrofuran (0.5 mL) was treated with 2.0 M aqueous sodium hydroxide solution (2.0 mL), and the resulting mixture was stirred at room temperature for 3 hours. The mixture was acidified by the addition of 2.0 M aqueous hydrochloric acid solution and concentrated under reduced pressure. The residue was purified by preparative HPLC, eluting with a mixture of acetonitrile and water (1:19 to 1:1 by volume) to afford the title compound as yellow solid (0.015 g).
$^1$HNMR (CDCl$_3$) δ 1.76 (s, 3H), 3.39 (d, J=17.0 Hz, 1H), 4.39 (d, J=17.7 Hz, 1H), 4.52 (d, J=17.7 Hz, 1H), 4.56 (d, J=17.0 Hz, 1H), 6.90 (m, 2H), 7.11 (d, J=5.3 Hz, 1H), 7.22 (m, 1H), 7.42 (dd, J=8.3, 2.9 Hz, 1H), 7.49 (d, J=5.3 Hz, 1H), 7.63 (dd, J=8.7, 5.0 Hz, 1H), 8.30 (m, 2H).
MS: ESI (+ve) (Method A): 445 (M+H)$^+$, Retention time 6.1 min.

Example 25

{3-[2-(3-chlorobenzenesulfonyl)pyridin-3-ylmethyl]-5-fluoro-2-methylindol-1-yl}acetic acid

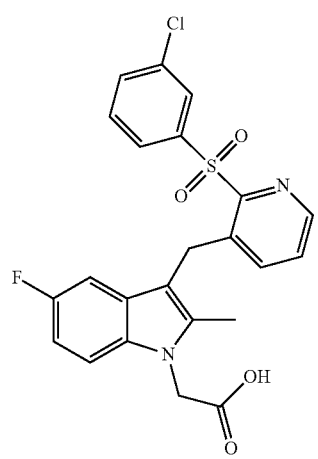 [SMILES: Cc1c(Cc2cccnc2S(=O)(=O)c2cccc(Cl)c2)c2cc(F)ccc2n1CC(=O)O]

Preparation 25a: 3-chlorobenzenesulfinic acid sodium salt

A solution of 3-chlorobenzenesulfonyl chloride (3.0 g) in dioxane (40 mL) was treated with a mixture of sodium hydrogen carbonate (2.7 g), sodium sulfite (3.6 g) and water (20 mL), and the resulting mixture was stirred at 75° C. for 30 minutes. The mixture was cooled to room temperature and concentrated under reduced pressure. The residue was triturated with ethanol to afford the title compound as a white solid (0.20 g).

Preparation 25b: 2-(3-chlorobenzenesulfonyl)pyridine-3-carbaldehyde

The title compound was prepared by the method of Preparation 5a using 2-chloropyridine-3-carbaldehyde and 3-chlorobenzenesulfinic acid sodium salt.

$^1$H NMR (CDCl$_3$): δ 7.40-7.56 (m, 1H), 7.60-7.67 (m, 2H), 7.92-7.96 (m, 1H), 8.02-8.04 (m, 1H), 8.40 (dd, J=1.7, 7.9 Hz, 1H), 8.71 (dd, J=1.7, 4.6 Hz, 1H), 11.12 (d, J=0.8 Hz, 1H).

Preparation 25c: {3-[2-(3-chlorobenzenesulfonyl)pyridin-3-ylmethyl]-5-fluoro-2-methylindol-1-yl}acetic acid methyl ester The title compound was prepared by the method of Preparation 1c using 2-(3-chlorobenzenesulfonyl)pyridine-3-carbaldehyde and (5-fluoro-2-methylindol-1-yl)acetic acid methyl ester.

$^1$H NMR (CDCl$_3$): δ 2.30 (s, 3H), 3.77 (s, 3H), 4.63 (s, 2H), 4.83 (s, 2H), 6.84 (dd, J=2.3, 9.5 Hz, 1H), 6.91 (dt, J=2.5, 9.1 Hz, 1H), 7.11 (dd, J=4.1, 8.8 Hz, 1H), 7.22 (dd, J=4.6, 7.9 Hz, 1H), 7.37-7.41 (m, 1H), 7.50-7.56 (m, 1H), 7.64 (ddd, J=1.1, 2.0, 8.0 Hz, 1H), 7.94-7.98 (m, 1H), 8.05-8.06 (m, 1H), 8.31-8.33 (m, 1H).

MS: ESI (+ve) (Method B): 487 (M+H)$^+$, Retention time 4.0 min.

Preparation 25d: {3-[2-(3-chlorobenzenesulfonyl)pyridin-3-ylmethyl]-5-fluoro-2-methylindol-1-yl}acetic acid A mixture of {3-[2-(3-chlorobenzenesulfonyl)pyridin-3-ylmethyl]-5-fluoro-2-methylindol-1-yl}acetic acid methyl ester (0.10 g) and tetrahydrofuran (5.0 mL) was treated with 1.0 M aqueous lithium hydroxide solution (0.31 mL), and the resulting mixture was stirred at room temperature for 1 hour. The mixture was concentrated under reduced pressure and the pH adjusted to 4 by the addition of 0.1 M aqueous hydrochloric acid solution. The mixture was extracted with ethyl acetate and the combined extract was washed with saturated aqueous sodium chloride solution and dried over magnesium sulfate. The solvent was removed under reduced pressure and the residue purified by preparative reverse-phase HPLC, eluting with a mixture of acetonitrile and water (1:19 to 49:1 by volume) to afford the title compound as a white solid (0.085 g).

$^1$H NMR (DMSO-d$_6$): δ 2.24 (s, 3H), 4.53 (s, 2H), 4.93 (s, 2H), 6.84 (dt, J=2.5, 9.2 Hz, 1H), 6.88 (dd, J=2.5, 9.8 Hz, 1H), 7.34-7.37 (m, 1H), 7.40 (dd, J=1.6, 8.0 Hz, 1H), 7.43-7.46 (m, 1H), 7.67-7.71 (m, 1H), 7.82-7.86 (m, 1H), 7.93-7.95 (m, 2H), 8.33 (dd, J=1.6, 4.4 Hz, 1H), 13.1 (br s, 1H).

MS: ESI (+ve) (Method A): 473 (M+H)$^+$, Retention time 11.1 min.

Example 26

{5-chloro-3-[2-(benzenesulfonyl)pyridine-3-ylmethyl]-2-methyl indol-1-yl}acetic acid

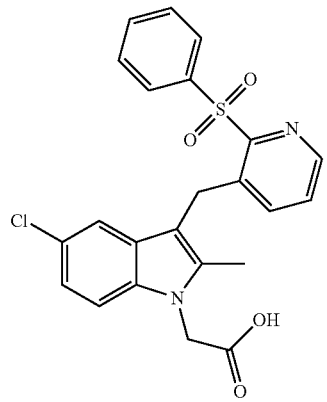 [SMILES: Cc1c(Cc2cccnc2S(=O)(=O)c2ccccc2)c2cc(Cl)ccc2n1CC(=O)O]

Preparation 26a: (5-chloro-2-methylindol-1-yl)acetic acid methyl ester

A mixture of (5-chloro-2-methylindol-1-yl)acetic acid (25 g), potassium carbonate (100 g) and N,N-dimethylformamide (220 mL) was treated dropwise with methyl bromoacetate (37 g), and the resulting mixture was stirred at 60° C. for 2 days. The mixture was cooled to room temperature and partitioned between water and ethyl acetate. The aqueous layer was extracted with ethyl acetate and the combined organic solution was washed with saturated aqueous sodium chloride solution, dried over sodium sulfate and concentrated under reduced pressure. The residue was purified by column chromatography on silica gel, eluting with a mixture of dichloromethane and pentane (1:10 to 1:0 by volume) to afford the title compound as a white solid (27 g).

$^1$H NMR (CDCl$_3$): δ 2.36 (s, 3H), 3.72 (s, 3H), 4.74 (s, 2H), 6.23 (s, 1H), 7.03-7.09 (m, 2H), 7.47 (d, J=1.5 Hz, 1H).

Preparation 26b: {5-chloro-3-[2-(benzenesulfonyl)pyridine-2-ylmethyl]-3-methylindol-1-yl}acetic acid methyl ester The title compound was prepared by the method of Preparation 1c using 2-(benzenesulfonyl)pyridine-3-carbaldehyde and (5-chloro-2-methylindol-1-yl)acetic acid methyl ester.

$^1$H NMR (CDCl$_3$): δ 2.25 (s, 3H), 3.72 (s, 3H), 4.52 (s, 2H), 4.88 (s, 2H), 7.01-7.08 (m, 2H), 7.36-7.40 (m, 3H), 7.65-7.70 (m, 3H), 7.95 (dt, J=1.5, 8.4 Hz, 2H), 8.30 (dd, J=1.6, 4.6 Hz, 1H).

Preparation 26c: {5-chloro-3-[2-(benzenesulfonyl)pyridine-2-ylmethyl]-3-methylindol-1-yl}acetic acid A mixture of {5-chloro-3-[2-(benzenesulfonyl)pyridin-2-ylmethyl]-3-methylindol-1-yl}acetic acid methyl ester (0.15 g) and tetrahydrofuran (1.3 mL) was treated with 5.0 M aqueous sodium hydroxide solution (1.7 mL), and the resulting mixture was stirred at 40° C. for 2 hours. The mixture was acidified by the addition of 5.0 M aqueous hydrochloric acid solution and extracted with ethyl acetate. The combined organic extract was dried over sodium sulfate and concentrated under reduced pressure. The residue was purified by preparative reverse-phase HPLC, eluting with a mixture of acetonitrile and water (2:3 to 9:1 by volume) to afford the title compound as a white solid (0.23 g).

$^1$H NMR (DMSO-$d_6$): δ 2.23 (s, 3H), 4.51 (s, 2H), 4.95 (s, 2H), 7.00 (dd, J=2.2, 8.7 Hz, 1H), 7.08 (d, J=1.9 Hz, 1H), 7.32-7.44 (m, 3H), 7.66 (m, 2H), 7.76 (tt, J=1.3, 7.5 Hz, 1H), 7.97 (dt, J=1.6, 8.3 Hz, 2H), 8.33 (dd, J=1.6, 4.5 Hz, 1H) 13.00 (br s, 1H).

MS: ESI (+ve) (Method A): 455 (M+H)$^+$, Retention time 10.6 min.

Example 27

{5-fluoro-3-[2-(2-chlorobenzenesulfonyl)pyridine-3-ylmethyl]-2-methylindol-1-yl}acetic acid

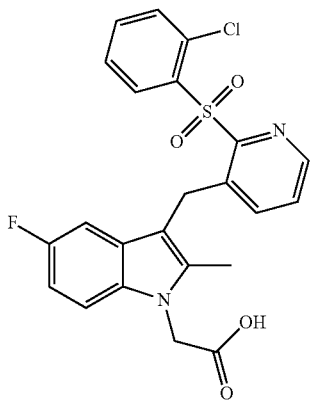 [SMILES: Cc1c(Cc2cccnc2S(=O)(=O)c2ccccc2Cl)c2cc(F)ccc2n1CC(=O)O]

Preparation 27a: 2-chlorobenzenesulfinic acid sodium salt

A mixture of 2-chlorobenzenesulfonyl chloride (2.5 g) and dioxane (35 mL) was treated with a mixture of sodium bicarbonate (2.0 g), sodium sulfite (3.0 g) and water (17 mL), and the resulting mixture was heated at 75° C. for 30 minutes. The mixture was cooled to room temperature and concentrated under reduced pressure. The residue was triturated with ethanol, filtered and the filtrate concentrated under reduced pressure. The residue was triturated with acetonitrile to afford the title compound as a white solid (2.3 g).

$^1$H NMR (CD$_3$OD): δ 7.31 (dd, J=1.2, 4.8 Hz, 2H), 7.34-7.40 (m, 1H), 7.86 (ddd, J=0.8, 1.2, 7.5 Hz, 1H).

Preparation 27b: 2-(2-chlorobenzenesulfonyl)pyridine-3-carbaldehyde

A mixture of 2-chlorobenzenesulfinic acid sodium salt (0.55 g), 2-chloropyridine-carbaldehyde (0.35 g) and dimethyl sulfoxide (10 mL) was heated at 100° C. for 2 days. The mixture was cooled to room temperature and partitioned between water and dichloromethane. The aqueous layer was extracted with dichloromethane and the combined organic solution was washed with saturated aqueous sodium chloride solution, dried over sodium sulfate and concentrated under reduced pressure. The residue was purified by column chromatography on silica gel, eluting with a mixture of ethyl acetate and pentane (0:1 to 3:2 by volume) to afford the title compound as a white solid (0.089 g).

$^1$H NMR (CDCl$_3$): δ 7.49 (dd, J=1.6, 7.6 Hz, 1H) 7.55-7.67 (m, 3H), 8.39 (dd, J=1.7, 7.9 Hz, 1H), 8.45 (dd, J=1.9, 7.6 Hz, 1H), 8.67 (dd, J=1.7, 4.6 Hz, 1H), 11.20 (d, J=0.8 Hz, 1H).

Preparation 27c: {5-fluoro-3-[2-(2-chlorobenzenesulfonyl)pyridine-3-ylmethyl]-2-methylindol-1-yl}acetic acid methyl ester A mixture of triethylsilane (0.76 mL), trifluoroacetic acid (0.61 mL) and 1,2-dichloroethane (3.0 mL) at −10° C. was treated dropwise with a mixture of (5-fluoro-2-methylindol-1-yl)acetic acid methyl ester (0.070 g), 2-(2-chlorobenzenesulfonyl)-pyridine-3-carbaldehyde (0.089 g) and 1,2-dichloroethane (6.0 mL), and the resulting mixture was stirred at −10° C. for 15 minutes and then at room temperature for 4 hours. The mixture was diluted with dichloromethane, washed with saturated aqueous sodium hydrogen carbonate solution and dried over sodium sulfate. The solvent was removed under reduced pressure and the residue purified by column chromatography on silica gel, eluting with a mixture of ethyl acetate and pentane (1:4 to 4:1 by volume). Further purification by crystallisation from ethyl acetate and pentane gave the title compound as a white solid (0.11 g).

$^1$H NMR (CDCl$_3$): δ 2.31 (s, 3H), 3.77 (s, 3H), 4.66 (s, 2H), 4.84 (s, 2H), 6.91 (dddd, J=2.4, 2.5, 6.8, 8.9 Hz, 2H), 7.12 (dd, J=4.1, 8.7 Hz, 1H), 7.23 (dd, J=4.5, 7.9 Hz, 1H), 7.40 (dd, J=1.0, 7.9 Hz, 1H), 7.51-7.64 (m, 3H), 8.29 (dd, J=1.3, 4.5 Hz, 1H), 8.40 (dd, J=1.8, 7.5 Hz, 1H).

Preparation 27d: {5-fluoro-3-[2-(2-chlorobenzenesulfonyl)pyridine-3-ylmethyl]-2-methylindol-1-yl}acetic acid A mixture of {5-fluoro-3-[2-(2-chlorobenzenesulfonyl)pyridin-3-ylmethyl]-2-methylindol-1-yl}acetic acid methyl ester and tetrahydrofuran (1.0 mL) was treated with 5.0 M aqueous sodium hydroxide solution (1.2 mL), and the resulting mixture was stirred at 45° C. for 4 hours. The mixture was acidified by the addition of 5.0 M aqueous hydrochloric acid solution and extracted with dichloromethane. The combined organic extract was dried over sodium sulfate and concentrated under reduced pressure. The residue was purified by preparative reverse-phase HPLC, eluting with a mixture of acetonitrile and water (2:3 to 9:1 by volume) to afford the title compound as a white solid (0.10 g).

$^1$H NMR (DMSO-$d_6$): δ 2.28 (s, 3H), 4.54 (s, 2H), 4.96 (s, 2H), 6.85 (dt, J=2.7, 9.3 Hz, 1H), 7.05 (dd, J=2.7, 9.7 Hz, 1H), 7.35-7.47 (m, 3H), 7.68 (dt, J=1.4, 8.0 Hz, 2H), 7.76 (dt, J=1.6, 6.7 Hz, 1H), 8.25 (dd. J=1.8, 7.9 Hz, 1H), 8.29 (dd, J=1.7, 4.3 Hz, 1H), 12.95 (br s, 1H).

MS: ESI (+ve) (Method A): 473 (M+H)$^+$, Retention time 10.7 min.

Example 28

[3-(5-benzenesulfonylpyrimidin-4-ylmethyl)-5-fluoro-2-methylindol-1-yl]acetic acid

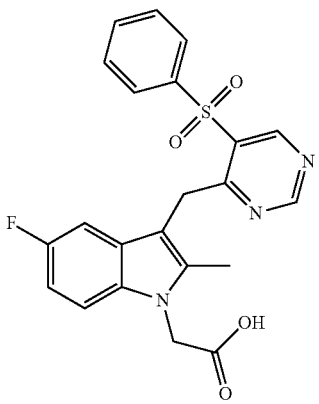 [SMILES: Cc1c(Cc2ncncc2S(=O)(=O)c2ccccc2)c2cc(F)ccc2n1CC(=O)O]

Preparation 28a: 5-benzenesulfonyl-2-methylsulfanylpyrimidine-4-carboxylic acid methyl ester A mixture of 5-bromo-2-methylsulfanylpyrimidine-4-carboxylic acid methyl ester (2.3 g), benzenesulfinic acid sodium salt (1.9 g) and dimethyl sulfoxide (35 mL) was treated with bis[copper(I)triflate]benzene complex (3.3 g), and the resulting mixture was stirred at 65° C. for 1.5 hours. The mixture was cooled to 40° C. and filtered through Celite. The filtrate was diluted with ethyl acetate, washed with saturated aqueous sodium hydrogen carbonate solution and dried over magnesium sulfate. The solvent was removed under reduced pressure and the residue purified by column chromatography on silica gel, eluting with a mixture of dichloromethane and ethyl acetate (1:0 to 4:1 by volume) to afford the title compound as a pale yellow solid (1.8 g).

MS: ESI (+ve) (Method B): 325 (M+H)$^+$, Retention time 3.5 min.

Preparation 28b: 5-benzenesulfonyl-2-methylsulfanylpyrimidine-4-carboxylic acid A mixture of 5-benzenesulfonyl-2-methylsulfanylpyrimidine-4-carboxylic acid methyl ester (1.4 g) and tetrahydrofuran (20 mL) was treated with 1.0 M aqueous lithium hydroxide solution (2.2 mL), and the resulting mixture was stirred at room temperature for 1 hour. The mixture was concentrated under reduced pressure, pH adjusted to 4 by the addition of 0.1 M aqueous hydrochloric acid solution and extracted with ethyl acetate. The combined extract was washed with saturated aqueous sodium chloride solution, dried over magnesium sulfate and concentrated under reduced pressure to afford the title compound as a pale yellow solid (1.3 g).

$^1$H NMR (CDCl$_3$): δ 2.62 (s, 3H), 7.52-7.66 (m, 3H), 8.02-8.05 (m, 2H), 9.21 (s, 1H).

MS: ESI (+ve) (Method B): 311 (M+H)$^+$, Retention time 2.4 min.

Preparation 28c: 5-(5-benzenesulfonyl-2-methylsulfanylpyrimidin-4-yl)methanol A mixture of 5-benzenesulfonyl-2-methylsulfanylpyrimidine-4-carboxylic acid (0.99 g), dichloromethane (50 mL) and N,N-dimethylformamide (0.2 mL) was treated with oxalyl chloride (0.83 mL), and the resulting reaction mixture was stirred at room temperature for two hours. The mixture was concentrated under reduced pressure and the residue was dissolved in a mixture of acetonitrile (20 mL) and tetrahydrofuran (30 mL). The mixture was cooled to −78° C. and treated with a 2.0 M solution of sodium borohydride in N,N-dimethylformamide (1.6 mL). The mixture was warmed to −50° C. over 2 hours, diluted with 1.0 M aqueous hydrochloric acid solution and concentrated under reduced pressure. The residue was diluted with ethyl acetate, washed with water and dried over magnesium sulfate. The solvent was removed under reduced pressure to afford the title compound as a yellow oil (0.59 g).

$^1$H NMR (DMSO-d$_6$): δ 2.61 (s, 3H), 4.66 (d, J=6.1 Hz, 2H), 5.36 (t, J=6.1 Hz, 1H), 7.62-7.68 (m, 3H), 8.00-8.03 (m, 2H), 9.12 (s, 1H).

MS: ESI (+ve) (Method B): 297 (M+H)$^+$, Retention time 3.0 min.

Preparation 28d: 5-benzenesulfonyl-2-methylsulfanylpyrimidine-4-carbaldehyde A mixture of 5-(5-benzenesulfonyl-2-methylsulfanylpyrimidin-4-yl)methanol (0.42 g) and dichloromethane (100 mL) was treated with Dess-Martin periodinane (0.72 g), and the resulting mixture was stirred at 0° C. for 30 min. The mixture was filtered through Celite and the filtrate concentrated under reduced pressure. The residue was purified by column chromatography on silica gel, eluting with a mixture of cyclohexane and ethyl acetate (1:0 to 0.1 by volume) to afford the title compound as a pale yellow oil (0.30 g).

$^1$H NMR (CDCl$_3$): δ 2.64 (s, 3H), 7.54-7.60 (m, 3H), 7.98-8.01 (m, 2H), 9.25 (s, 1H), 10.21 (s, 1H).

MS: ESI (+ve) (Method B): 295 (M+H)$^+$, Retention time 2.8 min.

Preparation 28e: [3-(5-benzenesulfonyl-2-methylsulfanylpyrimidin-4-ylmethyl)-5-fluoro-2-methyl-indol-1-yl]acetic acid methyl ester The title compound was prepared by the method of Preparation 1c using 5-benzenesulfonyl-2-methylsulfanylpyrimidine-4-carbaldehyde and (5-fluoro-2-methylindol-1-yl)acetic acid methyl ester.

$^1$H NMR (CDCl$_3$): δ 2.20 (s, 3H), 2.23 (s, 3H), 3.73 (s, 3H), 4.32 (s, 2H), 4.74 (s, 2H), 6.55 (dd, J=2.5, 9.6 Hz, 1H), 6.81 (dd, J=2.5, 9.1 Hz, 1H), 7.00 (dd, J=4.2, 8.9 Hz, 1H), 7.53-7.59 (m, 2H), 7.64-7.69 (m, 1H), 7.90-7.93 (m, 2H), 9.08 (s, 1H).

MS: ESI (+ve) (Method B): 500 (M+H)$^+$, Retention time 4.1 min.

Preparation 28f: [3-(5-benzenesulfonyl-2-methylsulfanylpyrimidin-4-ylmethyl)-5-fluoro-2-methyl-indol-1-yl]acetic acid A mixture of [3-(5-benzenesulfonyl-2-methylsulfanylpyrimidin-4-ylmethyl)-5-fluoro-2-methylindol-1-yl]acetic acid methyl ester (0.23 g) and tetrahydrofuran (30 mL) was treated with 1.0 M aqueous lithium hydroxide solution (0.93 mL), and the resulting mixture was stirred at room temperature for 1 hour. The mixture was concentrated under reduced pressure, the pH adjusted to 4 by the addition of 0.1 M aqueous hydrochloric acid solution and extracted with ethyl acetate. The combined extract was washed with saturated aqueous sodium chloride solution, dried over magnesium sulfate and concentrated under reduced pressure. The residue was purified by preparative reverse-phase HPLC, eluting with a mixture of acetonitrile and water (1:19 to 49:1 by volume) to afford the title compound as a yellow solid (0.20 g).

MS: ESI (+ve) (Method B): 486 (M+H)$^+$, Retention time 3.8 min.

Preparation 28q: [3-(5-benzenesulfonylpyrimidin-4-ylmethyl)-5-fluoro-2-methylindol-1-yl]acetic acid A mixture of [3-(5-benzenesulfonyl-2-methylsulfanylpyrimidin-4-ylmethyl)-5-fluoro-2-methylindol-1-yl]acetic acid (0.20 g), ethanol (12 mL) and water (12 mL) was treated with Raney Nickel 2800 (0.050 g), and the resulting reaction mixture was stirred at 60° C. for 45 minutes. The mixture was filtered through Celite and the filtrate was concentrated under reduced pressure. The residue was purified by preparative reverse-phase HPLC, eluting with a mixture of acetonitrile and water (1:19 to 49:1 by volume) to afford the title compound as an off-white solid (0.058 g).

$^1$H NMR (DMSO-d$_6$): δ 2.09 (s, 3H), 4.35 (s, 2H), 4.87 (s, 2H), 6.40 (dd, J=2.5, 9.9 Hz, 1H), 6.78 (dd, J=2.5, 9.2 Hz, 1H), 7.27 (dd, J=4.3, 8.8 Hz, 1H), 7.68 (m, 2H), 7.79 (tt, J=1.1, 7.6 Hz, 1H), 8.07 (m, 2H), 9.24 (s, 1H), 9.40 (s, 1H).

MS: ESI (+ve) (Method A): 440 (M+H)$^+$, Retention time 9.7 min.

Example 29

[3-(3-benzenesulfonylthiophen-2-ylmethyl)-5-chloro-2-methylindol-1-yl]acetic acid

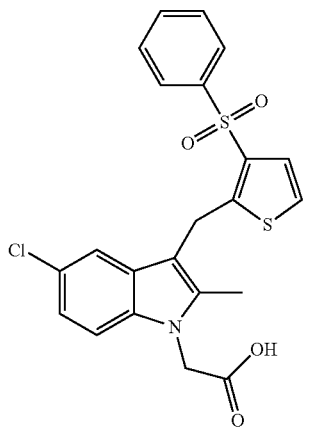 [SMILES: Cc1c(Cc2sccc2S(=O)(=O)c2ccccc2)c2cc(Cl)ccc2n1CC(=O)O]

Preparation 29a: [3-(3-benzenesulfonylthiophen-2-ylmethyl)-5-chloro-2-methylindol-1-yl]acetic acid methyl ester A mixture of triethylsilane (2.7 g), trifluoroacetic acid (1.6 g) and dichloroethane (8.0 mL) at −20° C. was treated dropwise with a mixture of (5-chloro-2-methylindol-1-yl)acetic acid methyl ester (0.36 g), 3-phenylsulphony-2-thiophenealdehyde (0.39 g) and dichloroethane (8.0 mL), and the resulting mixture was warmed to room temperature over a period of 1.5 hours. The mixture was treated with additional triethylsilane (2.7 g) and trifluoroacetic acid (1.6 g) and then stirred at room temperature for 1 hour. The mixture was diluted with saturated aqueous sodium hydrogen carbonate solution and extracted with dichloromethane. The combined organic extract was washed with saturated aqueous sodium chloride solution, dried over sodium sulfate and concentrated under reduced pressure. The residue was purified by column chromatography on silica gel, eluting with a mixture of dichloromethane and ethyl acetate (1:0 to 0:1 by volume) to afford the title compound (0.55 g).

MS: ESI (+ve) (Method B): 474 (M+H)$^+$, Retention time 4.1 min.

Preparation 29b: [3-(3-benzenesulfonylthiophen-2-ylmethyl)-5-chloro-2-methylindol-1-yl]acetic acid A mixture of [3-(3-benzenesulfonylthiophen-2-ylmethyl)-5-chloro-2-methylindol-1-yl]acetic acid methyl ester (0.47 g), 1.0 M aqueous lithium hydroxide solution (2.0 mL) and tetrahydrofuran (2.0 mL) was stirred at room temperature for 1 hour. The mixture was acidified with 1.0 M aqueous hydrochloric acid solution and extracted with ethyl acetate. The combined organic extract was dried using a phase separation cartridge and concentrated under reduced pressure. The residue was purified by crystallisation from a mixture of pentane and ethyl acetate to afford the title compound as a white powder (0.39 g).

$^1$H NMR (DMSO-d$_6$): δ 2.17 (s, 3H), 4.41 (s, 2H), 4.93 (s, 2H), 6.88 (d, J=2.0 Hz, 1H), 6.98 (dd, J=2.0, 8.7 Hz, 1H), 7.33 (s, 1H), 7.35 (d, J=5.5 Hz, 1H), 7.39 (d, J=5.5 Hz, 1H), 7.61-7.67 (m, 2H), 7.69-7.74 (m, 1H), 7.98-8.02 (m, 2H).

MS: ESI (+ve) (Method A): 459 (M+H)$^+$, Retention time 11.2 min.

Example 30

{5-fluoro-2-methyl-3-[2-(methyl-phenylsulfamoyl)pyridin-3-ylmethyl]indol-1-yl}acetic acid

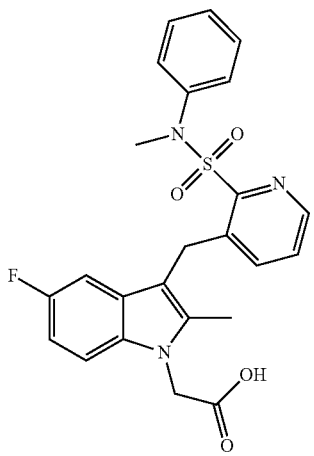 [SMILES: Cc1c(Cc2cccnc2S(=O)(=O)N(C)c2ccccc2)c2cc(F)ccc2n1CC(=O)O]

Preparation 30a: 2-phenylsulfamoylnicotinic acid methyl ester

A mixture of 2-mercaptonicotinic acid methyl ester (1.4 g), dichloromethane (50 mL) and 1.0 M aqueous hydrochloric acid solution (50 mL) at −10° C. was treated with sodium hypochlorite (8% in water, 50 mL) over a period of 5 minutes, and the resulting mixture was warmed to 0° C. over a period 15 minutes. The phases were separated and the organic phase was treated with 4A molecular sieves and aniline (1.5 g), and the resulting mixture was stirred at room temperature for 1.5 hours. The mixture was filtered and the filtrate was washed with saturated aqueous sodium hydrogen carbonate solution and dried over magnesium sulfate. The solvent was removed under reduced pressure and the residue purified by crystallisation from a mixture of cyclohexane and dichloromethane to afford the title compound (1.8 g).

MS: ESI (+ve) (Method B): 293 (M+H)⁺, Retention time 3.0 min.

Preparation 30b: 2-(methylphenylsulfamoyl)nicotinic acid methyl ester

A mixture of 2-phenylsulfamoylnicotinic acid methyl ester (1.8 g), acetonitrile (100 mL) and potassium carbonate (1.9 g) was treated with a mixture of methyl bromide (1.5 mL) and acetonitrile (6.0 mL), and the resulting mixture was stirred at room temperature for 24 hours. The mixture was concentrated under reduced pressure, triturated with dichloromethane and filtered. The filtrate was concentrated under reduced pressure to afford the title compound as a tan oil (1.5 g).

MS: ESI (+ve) (Method B): 307 (M+H)⁺, Retention time 3.4 min.

Preparation 30c: 3-hydroxymethylpyridine-2-sulfonic acid methylphenylamide

A mixture of 2-(methylphenylsulfamoyl)nicotinic acid methyl ester (1.5 g) and tetrahydrofuran (50 mL) at −78° C. was treated with a 1.0 M solution of lithium aluminium hydride in tetrahydrofuran (10 mL), and the resulting mixture was stirred at −78° C. for 1 hour and then at room temperature for 2 hours. The mixture was diluted with water, extracted with ethyl acetate and the combined organic extract was dried over magnesium sulfate. The solvent was removed under reduced pressure and the residue was purified by column chromatography on silica gel, eluting with a mixture of dichloromethane and methanol (1:0 to 19:1 by volume) to afford the title compound (0.25 g).

MS: ESI (+ve) (Method B): 279 (M+H)⁺, Retention time 3.0 min.

Preparation 30d: 3-formylpyridine-2-sulfonic acid methylphenylamide

A mixture of 3-hydroxymethylpyridine-2-sulfonic acid methylphenylamide (0.25 g), chloroform (20 mL) and manganese (IV) oxide (3.9 g) was stirred at room temperature for 2 hours. The mixture was treated with additional manganese (IV) oxide (1.6 g) and stirred at room temperature for a further 2 hours. The mixture was filtered through hyflo and the filtrate was concentrated under reduced pressure to afford the title compound (0.10 g).

MS: ESI (+ve) (Method B): 277 (M+H)⁺, Retention time 3.4 min.

Preparation 30e: {5-fluoro-2-methyl-3-[2-(methylphenylsulfamoyl)-pyridin-3-ylmethyl]indol-1-yl}acetic acid methyl ester The title compound was prepared by the method of Preparation 29a using (5-fluoro-2-methylindol-1-yl)acetic acid methyl ester and 3-formylpyridine-2-sulfonic acid methylphenylamide.

MS: ESI (+ve) (Method B): 482 (M+H)⁺, Retention time 4.2 min.

Preparation 30f: {5-fluoro-2-methyl-3-[2-(methylphenyl-sulfamoyl)pyridin-3-ylmethyl]indol-1-yl}acetic acid A mixture of {5-fluoro-2-methyl-3-[2-(methylphenylsulfamoyl)pyridin-3-ylmethyl]indol-1-yl}acetic acid methyl ester (0.14 g), 1.0 M aqueous sodium hydroxide solution (1.0 mL) and methanol (10 mL) was stirred at room temperature for 1.5 hours. The mixture was diluted with 1.0 M aqueous hydrochloric acid solution and concentrated under reduced pressure. The residue was diluted with 1.0 M aqueous hydrochloric acid solution and the resulting precipitate was collected by filtration and dried to give the title compound as a white solid (0.10 g).

¹H NMR (DMSO-d₆): δ 2.17 (s, 3H), 3.53 (s, 3H), 4.23 (s, 2H), 4.93 (s, 2H), 6.78-6.89 (m, 2H), 7.21-7.39 (m, 5H), 7.41-7.50 (m, 3H), 8.50 (dd, J=1.4, 4.5 Hz, 1H).

MS: ESI (+ve) (Method A): 468 (M+H)⁺, Retention time 11.3 min.

Example 31

{5-chloro-3-[3-(4-fluorobenzenesulfonyl)thiophen-2-ylmethyl]-2-methylindol-1-yl}acetic acid

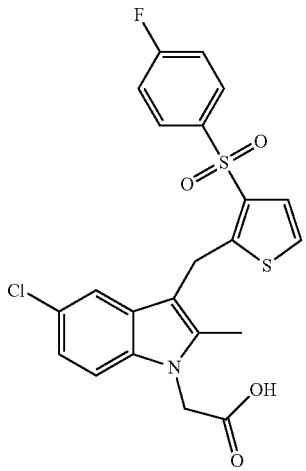 [SMILES: Cc1c(Cc2sccc2S(=O)(=O)c2ccc(F)cc2)c2cc(Cl)ccc2n1CC(=O)O]

Preparation 31a: 3-(4-fluorobenzenesulfonyl)thiophene-2-carbaldehyde

A mixture of 3-bromothiophenecarbaldehyde (5.0 g), dimethyl sulfoxide (50 mL) and 4-fluorophenyl sodium sulfinate (5.2 g) was stirred at 100° C. for 3 hours. Additional 4-fluorophenyl sodium sulfinate (1.9 g) was added and the mixture was stirred at 100° C. for 18 hours. The mixture was cooled to room temperature, diluted with water and extracted with ethyl acetate. The combined organic extract was washed with water and saturated aqueous sodium hydrogen carbonate solution and dried over magnesium sulfate. The solvent was removed under reduced pressure and the residue was purified by column chromatography on silica gel, eluting with a mixture of cyclohexane and ethyl acetate (1:0 to 7:3 by volume) to afford the title compound (4.4 g).

¹H NMR (DMSO-d₆): δ 7.48-7.55 (m, 2H), 7.66 (d, J=5.2 Hz, 1H), 8.18-8.25 (m, 3H), 10.51 (d, J=1.2 Hz, 1H)

Preparation 31b: {5-chloro-3-[3-(4-fluorobenzene-sulfonyl)thiophen-2-ylmethyl]-2-methyl-indol-1-yl}acetic acid methyl ester The title compound was prepared by the method of Preparation 29a using 3-(4-fluorobenzenesulfonyl)thiophene-2-carbaldehyde and (5-chloro-2-methylindol-1-yl)acetic acid methyl ester.
MS: ESI (+ve) (Method B): 492 (M+H)⁺, Retention time 4.3 min.

Preparation 31c: {5-chloro-3-[3-(4-fluorobenzene-sulfonyl)thiophen-2-ylmethyl]-2-methylindol-1-yl}acetic acid The title compound was prepared by the method of Preparation 30f using {5-chloro-3-[3-(4-fluorobenzenesulfonyl)thiophen-2-ylmethyl]-2-methylindol-1-yl}acetic acid methyl ester.
¹H NMR (DMSO-d₆): δ 2.28 (s, 3H), 4.49 (s, 2H), 5.00 (s, 2H), 6.86 (d, J=2.0 Hz, 1H), 7.05 (dd, J=2.0, 8.7 Hz, 1H), 7.43 (d, J=8.8 Hz, 1H), 7.45 (d, J=5.4 Hz, 1H), 7.49 (d, J=5.4 Hz, 1H), 7.53 (t, J=8.8 Hz, 2H), 8.15 (m, 2H).
MS: ESI (+ve) (Method A): 478 (M+H)⁺, Retention time 11.4 min.

Example 32

{5-chloro-2-methyl-3-[3-(Pyridine-2-sulfonyl)thiophen-2-ylmethyl]indol-1-yl}acetic acid

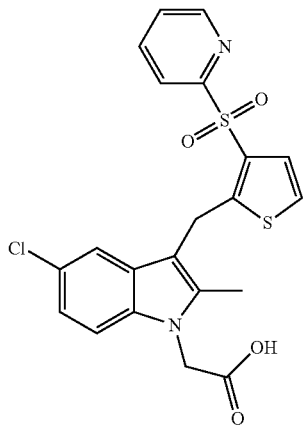 [SMILES: Cc1c(Cc2sccc2S(=O)(=O)c2ccccn2)c2cc(Cl)ccc2n1CC(=O)O]

Preparation 32a: 3-(pyridine-2-sulfonyl)thiophene-2-carbaldehyde

A mixture of pyridine-2-sulfinate sodium salt (8.5 g), 3-bromothiophene-2-carbaldehyde (6.5 g) and dimethyl sulfoxide (50 mL) (split equally into four microwave vials) was heated by microwave irradiation at 125° C. for 45 minutes. The combined mixtures were diluted with ethyl acetate, washed with saturated aqueous sodium hydrogen carbonate solution and saturated aqueous sodium chloride solution and dried over magnesium sulfate. The solvent was removed under reduced pressure and the residue was purified by column chromatography on silica gel, eluting with a mixture of dichloromethane and ethyl acetate (1:0 to 0:1 by volume) to afford the title compound as a yellow solid (0.55 g).
¹H NMR (CDCl₃): δ 7.52 (ddd, J=0.8, 4.7, 7.7 Hz, 1H), 7.58 (d, J=5.2 Hz, 1H), 7.69 (dd, J=1.0, 4.2 Hz, 1H), 7.98 (dt, J=1.7, 7.8 Hz, 1H), 8.23 (d, J=7.9 Hz, 1H), 8.70 (d, J=4.7 Hz, 1H), 10.7 (d, J=1.0 Hz 1H).

Preparation 32b: {5-chloro-2-methyl-3-[3-(pyridine-2-sulfonyl)thiophen-2-ylmethyl]indol-1-yl}acetic acid methyl ester The title compound was prepared by the method of Preparation 29a using 3-(pyridine-2-sulfonyl)thiophene-2-carbaldehyde and (5-chloro-2-methylindol-1-yl)acetic acid methyl ester.
MS: ESI (+ve) (Method B): 475 (M+H)⁺, Retention time 3.9 min.

Preparation 32c: {5-chloro-2-methyl-3-[3-(pyridine-2-sulfonyl)thiophen-2-ylmethyl]indol-1-yl}acetic acid The title compound was prepared by the method of Preparation 29b using {5-chloro-2-methyl-3-[3-(pyridine-2-sulfonyl)thiophen-2-ylmethyl]indol-1-yl}acetic acid methyl ester.
¹H NMR (DMSO-d₆): δ 2.22 (s, 3H), 4.52 (s, 2H), 4.93 (s, 2H), 6.99 (dd, J=2.1, 8.7 Hz, 1H), 7.06 (dd, J=2.0 Hz, 1H), 7.29 (d, J=5.3 Hz, 1H), 7.35 (d, J=8.7 Hz, 1H), 7.38 (d, J=5.3 Hz, 1H), 7.72 (ddd, J=1.2, 4.6, 7.6 Hz, 1H), 8.13 (dt, J=1.7, 7.8 Hz, 1H), 8.20 (d, J=7.8 Hz, 1H), 8.76 (m, 1H).
MS: ESI (+ve) (Method A): 461 (M+H)⁺, Retention time 10.4 min.

Example 33

{5-fluoro-2-methyl-3-[2-(pyrimidine-5-sulfonyl)benzyl]indol-1-yl}acetic acid

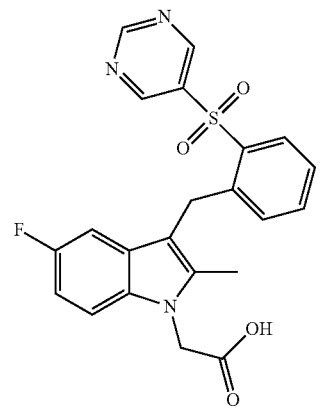 [SMILES: Cc1c(Cc2ccccc2S(=O)(=O)c2cncnc2)c2cc(F)ccc2n1CC(=O)O]

Preparation 33a: 5-[2-(tert-butyl-dimethylsilanyloxymethyl)phenylsulfanyl]pyrimidine A mixture of 2-(tert-butyl-dimethylsilanyloxymethyl)benzenethiol (5.6 g), 5-bromopyridine (4.6 g), cesium carbonate (11 g) and N-methylpyrrolidone (25 mL) was heated at 100° C. for 2 hours. The mixture was diluted with water and extracted with diethyl ether. The combined organic extract was washed with water and saturated aqueous sodium chloride solution and dried over magnesium sulfate. The solvent was removed under reduced pressure and the residue was purified by column chromatography on silica gel, eluting with a mixture of cyclohexane and ethyl acetate (1:0 to 0:1 by volume) to afford the title compound as a light brown oil (7.0 g).

MS: ESI (+ve) (Method B): 333 (M+H)$^+$, Retention time 4.7 min.

Preparation 33b: 5-[2-(tert-butyl-dimethylsilany-loxymethyl)benzenesulfonyl]pyrimidine A mixture of 5-[2-(tert-butyl-dimethylsilanyloxymethyl) phenylsulfanyl]pyrimidine (8.1 g) and dichloromethane (200 mL) at 0° C. was treated portion wise with 3-chloroperoxy-benzoic acid (15 g), and the resulting mixture was stirred at room temperature for 4 hours. The mixture was partitioned between dichloromethane and saturated solution of sodium hydrogen carbonate. The organic phase was washed with saturated aqueous sodium chloride solution, dried over sodium sulfate and concentrated under reduced pressure. The residue was purified by column chromatography on silica gel, eluting with a mixture of cyclohexane and ethyl acetate (1:0 to 8.5:2.5 by volume) to afford the title compound as a pale brown oil (7.0 g).

MS: ESI (+ve) (Method B): 438 (M+H)$^+$, Retention time 3.7 min.

Preparation 33c: [2-(pyrimidine-5-sulfonyl)phenyl]methanol

A mixture of 5-[2-(tert-butyl-dimethylsilanyloxymethyl) benzenesulfonyl]pyrimidine (2.1 g) and tetrahydrofuran (2.0 mL) was treated with 1.0 M solution of tetrabutylammonium fluoride in tetrahydrofuran (7.5 mL), and the resulting mixture was stirred at room temperature for 30 minutes. The reaction mixture was diluted with ethyl acetate, washed with saturated aqueous sodium chloride solution and dried over magnesium sulfate. The solvent was removed under reduced pressure to afford the title compound a pale brown solid (0.64 g).

MS: ESI (+ve) (Method B): 251 (M+H)$^+$, Retention time 2.4 min.

Preparation 33d: 2-(pyrimidine-5-sulfonyl)benzaldehyde

The title compound was prepared by the method of Preparation 30d using [2-(pyrimidine-5-sulfonyl)phenyl]methanol.

MS: ESI (+ve) (Method B): 247 (M+H)$^-$, Retention time 2.6 min.

Preparation 33e: {5-fluoro-2-methyl-3-[2-(pyrimidine-5-sulfonyl)benzyl]indol-1-yl}acetic acid methyl ester A mixture of (5-chloro-2-methylindol-1-yl)acetic acid methyl ester (0.50 g), 2-(pyrimidine-5-sulfonyl)benzaldehyde (0.35 g) and dichloroethane (50 mL) at −70° C. was treated sequentially with triethylsilane (2.5 g) and trifluoroacetic acid (0.81 g), and the resulting mixture was stirred at −70° C. for 1 hour. The mixture was slowly warmed to room temperature and stirred at this temperature for 18 hours. The mixture was diluted with saturated aqueous sodium hydrogen carbonate solution and the phases were separated. The organic phase was concentrated under reduced pressure and the residue was purified by column chromatography on silica gel, eluting with a mixture of cyclohexane and ethyl acetate (4:1 to 2:3 by volume) to afford the title compound as a brown oil (0.12 g).

MS: ESI (+ve) (Method B): 454 (M+H)$^+$, Retention time 3.6 min.

Preparation 33f: {5-fluoro-2-methyl-3-[2-(pyrimidine-5-sulfonyl)benzyl]indol-1-yl}acetic acid The title compound was prepared by the method of Preparation 29b using {5-fluoro-2-methyl-3-[2-(pyrimidine-5-sulfonyl)benzyl]indol-1-yl}acetic acid methyl ester.

$^1$H NMR (CD$_3$OD): δ 2.64 (s, 3H), 4.39 (s, 2H), 4.86 (s, 2H), 6.10 (dd, J=2.5, 9.9 Hz, 1H), 6.70 (dt, J=2.5, 9.1 Hz, 1H), 7.04 (dd, J=4.4, 8.9 Hz, 1H), 7.42 (dd, J=0.7, 7.4 Hz, 1H), 7.58-7.70 (m, 2H), 8.34 (dd, J=1.5, 7.8 Hz, 1H), 8.82 (s, 2H), 9.07 (s, 1H).

MS: ESI (+ve) (Method A): 440 (M+H)$^+$, Retention time 9.6 min.

Example 34

[3-(5-benzenesulfonylthiazol-4-ylmethyl)-5-fluoro-2-methylindol-1-yl]acetic acid

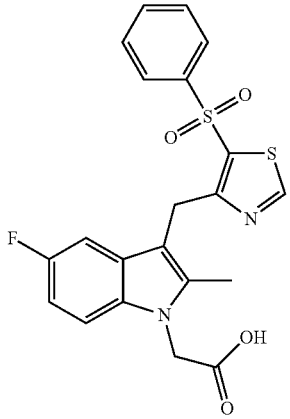 [SMILES: Cc1c(Cc2ncsc2S(=O)(=O)c2ccccc2)c2cc(F)ccc2n1CC(=O)O]

Preparation 34a: 4-bromomethyl-5-chlorothiazole

A mixture of 4-methyl-5-chlorothiazole (2.8 g), carbon tetrachloride (100 mL), N-bromosuccinimide (4.9 g) and dibenzoyl peroxide (0.25 g) was heated at reflux for 3 hours. The mixture was cooled to room temperature, filtered and the filtrate concentrated under reduced pressure to afford the title compound as a red oil (4.4 g).

Preparation 34b: 5-chlorothiazole-4-carbaldehyde

A mixture of 4-bromomethyl-5-chlorothiazole (4.4 g), 4A molecular sieves (44 g) and acetonitrile (100 mL) at 0° C., was treated portion wise with N-methylmorpholine oxide (4.9 g), and the resulting mixture was stirred at room temperature for 18 hours. The mixture was filtered through hyflo and the filtrate was concentrated under reduced pressure. The residue was purified by column chromatography on silica gel, eluting with a mixture of cyclohexane and ethyl acetate (1:0 to 3:2 by volume) to afford the title compound as a white solid (1.1 g).

$^1$H NMR (CDCl$_3$): δ 8.74 (s, 1H), 10.6 (s, 1H).

Preparation 34c: 5-benzenesulfonylthiazole-4-carbaldehyde

The title compound was prepared by the method of Preparation 5a using 5-chlorothiazole-4-carbaldehyde and phenylsulfinic acid sodium salt.

$^1$H NMR (CDCl$_3$): δ 7.57-7.63 (m, 2H), 7.66-7.71 (m, 1H), 8.07-8.11 (m, 2H), 8.98 (s, 1H), 10.42 (s, 1H).

MS: ESI (+ve) (Method B): 254 (M+H)$^+$, Retention time 9.6 min.

Preparation 34d: [3-(5-benzenesulfonylthiazol-4-ylmethyl)-5-fluoro-2-methylindol-1-yl]acetic acid methyl ester The title compound was prepared by the method of Preparation 1c using (5-fluoro-2-methylindol-1-yl)acetic acid methyl ester and 5-benzenesulfonylthiazole-4-carbaldehyde in dichloromethane.

Preparation 34e: [2-(5-benzenesulfonylthiazol-4-ylmethyl)-5-fluoro-2-methylindol-1-yl]acetic acid The title compound was prepared by the method of Preparation 29b using [3-(5-benzenesulfonylthiazol-4-ylmethyl)-5-fluoro-2-methylindol-1-yl]acetic acid methyl ester.

$^1$H NMR (DMSO-d$_6$): δ 2.16 (s, 3H), 4.28 (s, 2H), 4.29 (s, 2H), 6.67 (dt, J=2.5, 9.1 Hz, 1H), 6.75 (dd, J=2.5, 10.3 Hz, 1H), 7.07 (dd, J=4.5, 8.8 Hz, 1H), 7.56-7.63 (m, 2H), 7.65-7.71 (m, 2H), 7.88-7.93 (m, 2H), 9.23 (s, 1H).

MS: ESI (+ve) (Method A): 445 (M+H)$^+$, Retention time 10.4 min.

Example 35

{5-fluoro-2-methyl-3-[5-(pyridine-2-sulfonyl)thiazol-4-ylmethyl]indol-1-yl}acetic acid

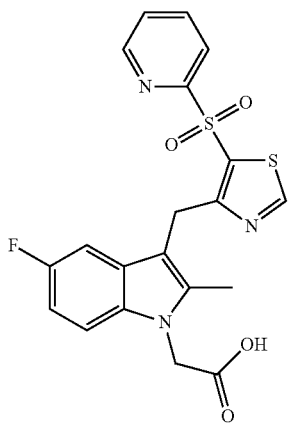 [SMILES: Cc1c(Cc2ncsc2S(=O)(=O)c2ccccn2)c2cc(F)ccc2n1CC(=O)O]

Preparation 35a: 5-(pyridine-2-sulfonyl)thiazole-4-carbaldehyde

The title compound was prepared by the method of Preparation 5a using 5-chloro-thiazole-4-carbaldehyde and pyridine-2-sulfinic acid sodium salt.

MS: ESI (+ve) (Method B): 257 (M+H)$^+$, Retention time 2.1 min.

Preparation 35b: {5-fluoro-2-methyl-3-[5-(pyridine-2-sulfonyl)thiazol-4-ylmethyl]indol-1-yl}acetic acid methyl ester The title compound was prepared by the method of Preparation 1c using (5-fluoro-2-methylindol-1-yl)acetic acid methyl ester and 5-(pyridine-2-sulfonyl)thiazole-4-carbaldehyde.

MS: ESI (+ve) (Method B): 460 (M+H)$^+$, Retention time 3.6 min.

Preparation 35c: {5-fluoro-2-methyl-3-[5-(Pyridine-2-sulfonyl)thiazol-4-ylmethyl]indol-1-yl}acetic acid The title compound was prepared by the method of Preparation 29b using {5-fluoro-2-methyl-3-[5-(pyridine-2-sulfonyl)thiazol-4-ylmethyl]indol-1-yl}acetic acid methyl ester.

$^1$H NMR (DMSO-d$_6$): δ 2.21 (s, 3H), 4.34 (s, 2H), 4.83 (s, 2H), 6.75 (m, 2H), 7.19 (dd, J=4.4, 8.8 Hz, 1H), 7.62 (ddd, J=1.4, 4.7, 7.3 Hz, 1H), 8.00-8.09 (m, 2H), 8.59-8.62 (m, 1H), 9.30 (s, 1H), 12.9 (br s, 1H).

MS: ESI (+ve) (Method A): 446 (M+H)$^+$, Retention time 9.3 min.

Example 36

[3-(2-benzenesulfonylbenzyl)-5-fluoro-2-methylindol-1-yl]acetic acid

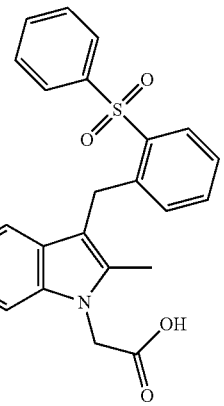

Preparation 36a: [3-(2-benzenesulfonylbenzyl)-5-fluoro-2-methylindol-1-yl]acetic acid methyl ester A mixture of triethylsilane (0.71 g), trifluoroacetic acid (0.53 g) and 1,2-dichloroethane (2.0 mL) at −10° C. was treated dropwise with a mixture of (5-fluoro-2-methylindol-1-yl)acetic acid methyl ester (0.091 g), 2-benzenesulfonylbenzaldehyde (0.12 g) and 1,2-dichloroethane (3.0 mL), and the resulting mixture was stirred at −10° C. for 15 minutes and then at room temperature for 2 hours. The mixture was diluted with dichloromethane, washed with saturated aqueous sodium hydrogen carbonate solution and dried over magnesium sulfate. The solvent was removed under reduced pressure and the residue purified by column chromatography on silica gel, eluting with a mixture of cyclohexane and dichloromethane (1:1 to 0:1 by volume) to afford the title compound as a colourless gum (0.17 g).

MS: ESI (+ve) (Method B): 452 (M+H)⁺, Retention time 4.1 min.

Preparation 36b: [3-(2-benzenesulfonylbenzyl)-5-fluoro-2-methylindol-1-yl]acetic acid A mixture of [3-(2-benzenesulfonylbenzyl)-5-fluoro-2-methylindol-1-yl]acetic acid methyl ester (0.17 g), tetrahydrofuran (3.0 mL) and methanol (1.5 mL) was treated with 1.0 M aqueous sodium hydroxide solution (1.5 mL), and the resulting mixture was stirred at room temperature for 2 hours. The mixture was acidified by the addition of 1.0 M aqueous hydrochloric acid solution (1.5 mL) and concentrated under reduced pressure. The residue was dissolved in ethyl acetate, dried over magnesium sulfate and concentrated under reduced pressure to afford the title compound as a cream solid (0.13 g).

¹H NMR (DMSO-d₆): δ 2.06 (s, 3H), 4.14 (s, 2H), 4.94 (s, 2H), 6.19 (dd, J=2.6, 7.3 Hz, 1H), 6.81 (dt, J=2.6, 9.1 Hz, 1H), 6.89 (m, 1H), 7.33 (dd, J=4.3, 9.1 Hz, 1H), 7.51 (m, 2H), 7.67 (m, 2H), 7.75 (m, 1H), 7.95 (m, 2H), 8.23 (m, 1H), 12.99 (br s, 1H).

MS: ESI (+ve) (Method A): 438 (M+H)⁺, Retention time 11.0 min.
MS: ESI (+ve) (Method B): 438 (M+H)⁺, Retention time 3.8 min.

Example 37

[3-(3-benzenesulfonyl-5-methylthiophen-2-ylmethyl)-5-fluoro-2-methylindol-1-yl]acetic acid

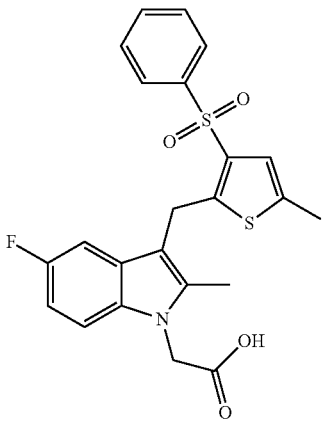 [SMILES: Cc1cc(S(=O)(=O)c2ccccc2)c(Cc2c(C)n(CC(=O)O)c3ccc(F)cc23)s1]

Preparation 37a:
3-benzenesulfonyl-5-methylthiophene-2-carbaldehyde

The title compound was prepared by the method of Preparation 7a using 3-bromo-5-methylthiophene-2-carbaldehyde and phenylsulfinic acid sodium salt.

¹H NMR (CDCl₃): δ 2.52 (d, J=1.0 Hz, 3H), 7.17 (d, J=1.0 Hz, 1H), 7.53-7.68 (m, 3 H), 7.94-7.99 (m, 2H), 10.55 (s, 1H).

Preparation 37b: [3-(3-benzenesulfonyl-5-methylthiophen-2-ylmethyl)-5-fluoro-2-methylindol-1-yl] acetic acid methyl ester The title compound was prepared by the method of Preparation 29a using 3-benzenesulfonyl-5-methylthiophene-2-carbaldehyde and (5-fluoro-2-methylindol-1-yl)acetic acid methyl ester.

¹H NMR (CDCl₃): δ 2.26 (s, 6H), 3.74 (s, 3H), 4.38 (s, 2H), 4.78 (s, 2H), 6.65 (dd, J=2.5, 9.4 Hz, 1H), 6.84 (td, J=2.5, 9.0 Hz, 1H), 7.01-7.08 (m, 2H), 7.52-7.66 (m, 3 H), 7.97-8.02 (m, 2H).

Preparation 37c: [3-(3-benzenesulfonyl-5-methylthiophen-2-ylmethyl)-5-fluoro-2-methylindol-1-yl] acetic acid The title compound was prepared by the method of Preparation 29b using [3-(3-benzenesulfonyl-5-methylthiophen-2-ylmethyl)-5-fluoro-2-methylindol-1-yl]acetic acid methyl ester.

¹H NMR (DMSO-d₆): δ 2.20 (s, 3H), 2.26 (s, 3H), 4.40 (s, 2H), 4.93 (s, 2H), 6.71 (dd, J=2.5, 9.8 Hz, 1H), 6.85 (td, J=2.5, 9.2 Hz, 1H), 7.08 (d, J=1.3 Hz, 1H), 7.35 (dd, J=4.4, 8.9 Hz, 1H), 7.65-7.71 (m, 2H), 7.72-7.77 (m, 1H), 8.01-8.05 (m, 2H).

MS: ESI (+ve) (Method A): 458 (M+H)⁺, Retention time 11.3 min.

Example 38

{5-fluoro-2-methyl-3-[5-methyl-3-(pyridine-2-sulfonyl)thiophen-2-ylmethyl]indol-1-yl}acetic acid

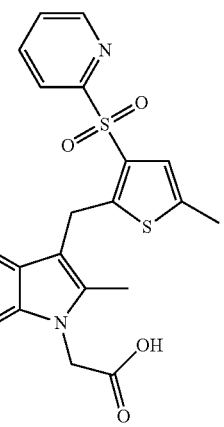

Preparation 38a: 5-methyl-3-(pyridine-2-sulfonyl)thiophene-2-carbaldehyde

The title compound was prepared by the method of Preparation 7a using 3-bromo-5-methylthiophene-2-carbaldehyde and pyridine-2-sulfinate sodium salt.

¹H NMR (DMSO-d₆): δ 2.54 (d, J=1.0 Hz, 3H), 7.49-7.53 (m, 1H), 7.97 (td, J=1.7, 7.8, Hz, 1H), 8.21 (dt, J=1.0, 7.9, Hz, 1H), 8.70 (ddd, J=0.9, 1.7, 4.7 Hz, 1H), 10.58 (s, 1 H).

Preparation 38b: 5-fluoro-2-methyl-3-[5-methyl-3-(pyridine-2-sulfonyl)thiophen-2-ylmethyl]indol-1-yl}acetic acid methyl ester A mixture of (5-fluor-2-methylindol-1-yl)acetic acid methyl ester (0.059 g), 5-methyl-3-(pyridine-2-sulfonyl)thiophene-2-carbaldehyde (0.071 g) and dichloroethane (1.5 mL) at 0° C. was treated dropwise with a solution of triethylsilane (0.46 g) and trifluoroacetic acid (0.27 g) in dichloroethane (1.0 mL), and the resulting mixture was stirred at room temperature for 1 hour and then at 60° C. for 1 hour. The mixture was cooled to room temperature and additional triethylsilane (2.7 g) and trifluoroacetic acid (1.6 g) were added, and the resulting mixture was stirred at room temperature for 1 hour. The mixture was partitioned between dichloromethane and saturated aqueous sodium hydrogen carbonate solution. The phases were separated and the organic phase was dried over magnesium sulfate and concentrated under reduced pressure. The residue was purified by column chromatography on silica gel, eluting with a mixture of cyclohexane and ethyl acetate (1:0 to 2:3 by volume) to afford the title compound (0.060 g).

$^1$H NMR (CDCl$_3$): δ 2.34 (s, 3H), 2.26 (d, J=1.1, 3H), 3.75 (s, 3H), 4.63 (s, 2H), 4.80 (s, 2H), 6.87 (dt, J=2.5, 9.0, 1H), 6.95 (dd, J=2.4, 9.5 Hz, 1H), 7.04-7.08 (m, 2H), 7.50-7.54 (m, 1H), 7.95 (dt, J=1.7, 7.7 Hz, 1H), 8.19 (dt, J=1.0, 7.9, Hz, 1H), 8.78-8.81 (m, 1H).

MS: ESI (+ve) (Method B): 473 (M+H)$^+$, Retention time 3.9 min.

Preparation 38c: {5-fluoro-2-methyl-3-[5-methyl-3-(pyridine-2-sulfonyl)thiophen-2-ylmethyl]indol-1-yl}acetic acid The title compound was prepared by the method of Preparation 29b using 5-fluoro-2-methyl-3-[5-methyl-3-(pyridine-2-sulfonyl)thiophen-2-ylmethyl]indol-1-yl}acetic acid methyl ester.

$^1$H NMR (DMSO-d$_6$): δ 2.25 (s, 3H), 2.26 (d, J=1.1 Hz, 3H), 4.50 (s, 2H), 4.95 (s, 2 H), 6.86 (dd, J=2.5, 9.1 Hz, 1H), 6.90 (dd, J=2.4, 10.1 Hz, 1H), 7.02 (d, J=1.3 Hz, 1H), 7.35 (dd, J=4.4, 8.8 Hz, 1 H), 7.76 (ddd, J=1.3, 4.7, 7.5 Hz, 1H), 8.17 (td, J=1.7, 7.6 Hz, 1H), 8.23 (dt, J=1.1, 7.9 Hz, 1H), 8.79 (ddd, J=0.9, 1.7, 4.7 Hz, 1H).

MS: ESI (+ve) (Method A): 459 (M+H)$^+$, Retention time 10.4 min.

Example 39

[5-fluoro-2-methyl-3-(2-phenylsulfamoylpyridin-3-ylmethyl)indol-1-yl]acetic acid

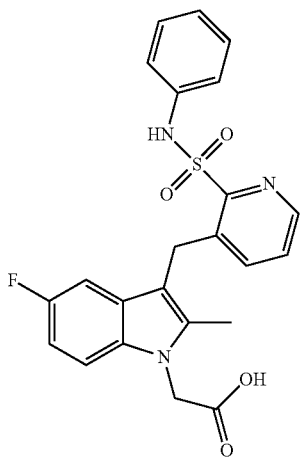 [SMILES: Cc1c(Cc2cccnc2S(=O)(=O)Nc2ccccc2)c2cc(F)ccc2n1CC(=O)O]

Preparation 39a: 2-{phenyl-[2-(trimethylsilanyl)ethoxymethyl]sulfamoyl}nicotinic acid methyl ester A mixture of 2-phenylsulfamoylnicotinic acid methyl ester (1.1 g), N,N-diisopropylethylamine (1.9 mL) and dichloromethane at 0° C. was treated with 2-(trimethylsilyl)ethoxymethyl chloride (0.67 mL), and the resulting mixture was stirred at room temperature overnight. The mixture was cooled to 0° C., treated with additional (trimethylsilyl)ethoxymethyl chloride (0.30 mL), and stirred at room temperature for 5 hours. The mixture was concentrated under reduced pressure and the residue was purified by column chromatography on silica gel, eluting with a mixture of dichloromethane and cyclohexane (0:1 to 1:0 by volume) to afford the title compound (1.6 g).

$^1$H NMR (CDCl$_3$): δ −0.07-0.02 (m, 9H), 0.87-0.95 (m, 2H), 3.75-3.82 (m, 2H), 3.85 (s, 3H), 5.33 (s, 2H), 7.15-7.29 (m, 5H), 7.53 (ddd, J=0.9, 4.7, 7.8 Hz, 1H), 7.92-7.97 (m, 1H), 8.72-8.76 (m, 1H).

Preparation 39b: 3-hydroxymethylpyridine-2-sulfonic acid phenyl[2-(trimethylsilanyl)ethoxymethyl]amide The title compound was prepared by the method of Preparation 30c using (2-{phenyl-[2-(trimethylsilanyl)ethoxymethyl]sulfamoyl}nicotinic acid methyl ester.

$^1$H NMR (CDCl$_3$): δ 0.00-0.04 (m, 9H), 0.91-0.98 (m, 2H), 2.74 (t, J=7.1 Hz, 1H), 3.79-3.85 (m, 2H), 4.79 (d, J=7.1 Hz, 2H), 5.33 (s, 2H), 7.27-7.34 (m, 5H), 7.50 (dd, J=4.7, 7.8 Hz, 1H), 7.94 (dd, J=1.6, 7.8 Hz, 1H), 8.6 (dd, J=1.7, 4.7 Hz, 1H).

Preparation 39c: 3-formylpyridine-2-sulfonic acid phenyl[2-(trimethylsilanyl) ethoxymethyl]amide The title compound was prepared by the method of Preparation 30d using 3-hydroxymethylpyridine-2-sulfonic acid phenyl[2-(trimethylsilanyl)ethoxymethyl]amide.

$^1$H NMR (CDCl$_3$): δ 0.00-0.03 (m, 9H), 0.89-0.97 (m, 2H), 3.76-3.84 (m, 2H), 5.34 (s, 2H), 7.28-7.36 (m, 5H), 7.64 (ddd, J=0.8, 4.7, 7.9 Hz, 1H), 8.35 (dd, J=1.8, 7.9 Hz, 1H), 8.86 (dd, J=1.8, 4.7 Hz, 1H), 10.56 (d, J=0.8 Hz, 1H).

Preparation 39d: [5-fluoro-2-methyl-3-(2-phenylsulfamoylpyridin-3-ylmethyl)indol-1-yl]acetic acid methyl ester A mixture of triethylsilane (3.1 mL), trifluoroacetic acid (0.88 mL) and dichloroethane (12 mL) at −15° C. was treated dropwise with a mixture of 3-formylpyridine-2-sulfonic acid phenyl[2-(trimethylsilanyl)ethoxymethyl]amide (0.55 g), (5-fluoro-2-methylindol-1-yl)acetic acid methyl ester (0.29 g) and dichloroethane (18 mL), and the resulting mixture was stirred at room temperature overnight. The mixture was concentrated under reduced pressure and the residue was dissolved in dichloromethane. The mixture was washed with saturated aqueous sodium hydrogen carbonate solution, dried over magnesium sulfate and concentrated under reduced pressure. The residue was purified by column chromatography on silica gel, eluting with a mixture of dichloromethane, cyclohexane, ethyl acetate and methanol (9:1:0:0 to 0:0:9:1 by volume) to afford the title compound (0.20 g).

MS: ESI (+ve) (Method B): 466 (M−H)$^−$, Retention time 3.9 min.

Preparation 39e: [5-fluoro-2-methyl-3-(2-phenylsulfamoylpyridin-3-ylmethyl)indol-1-yl]acetic acid A mixture of [5-fluoro-2-methyl-3-(2-phenylsulfamoylpyridin-3-ylmethyl)indol-1-yl]acetic acid methyl ester (0.20 g), 1.0 M aqueous sodium hydroxide solution (0.50 mL) and methanol (10 mL) was stirred at room temperature for 3 hours. The mixture was concentrated under reduced pressure and the residue was diluted with 1.0 M aqueous hydrochloric acid solution. The resulting precipitate was collected by filtration and purified by preparative reverse-phase HPLC, eluting with a mixture of acetonitrile and water (3:7 to 9:1 by volume) to afford the title compound (0.020 g).

$^1$H NMR (DMSO-$d_6$): δ 2.25 (s, 3H), 4.44 (s, 2H), 4.98 (s, 2H), 6.84-6.94 (m, 2H), 7.00-7.08 (m, 1H), 7.23-7.28 (m, 4H), 7.30-7.34 (m, 1H), 7.36-7.45 (m, 2H), 8.43 (dd, J=1.5, 4.5 Hz, 1H), 10.71 (s, 1H), 13.02 (br s, 1H).

MS: ESI (+ve) (Method A): 454 (M+H)$^+$, Retention time 10.2 min.

Example 40

{3-[2-(2,4-dichlorobenzenesulfonyl)benzyl]-5-fluoro-2-methylindol-1-yl}acetic acid

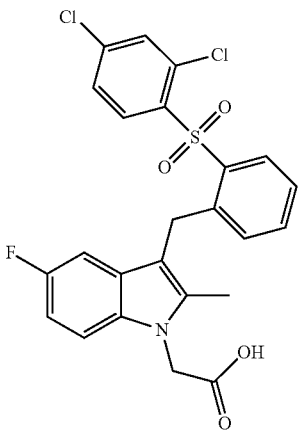 [SMILES: Cc1c(Cc2ccccc2S(=O)(=O)c2ccc(Cl)cc2Cl)c2cc(F)ccc2n1CC(=O)O]

Preparation 40a:
2-(2,4-dichlorobenzenesulfonyl)benzaldehyde

A mixture of 3-chloroperoxybenzoic acid (77% in water, 5.5 g) and dichloromethane (10 mL) was treated dropwise with a mixture of 2-(2,4-dichlorophenylsulfanyl)benzaldehyde (2.3 g) and dichloromethane (10 mL), and the resulting mixture was stirred at room temperature for 2 hours. The mixture was partitioned between dichloromethane and saturated aqueous sodium hydrogen carbonate solution. The phases were separated and the organic phase was washed with saturated aqueous sodium hydrogen carbonate solution and dried over potassium carbonate. The solvent was removed under reduced pressure and the residue purified by column chromatography on silica gel, eluting with a mixture of cyclohexane and dichloromethane (1:0 to 1:2 by volume) to afford the title compound as a white solid (0.55 g).

$^1$H NMR (CDCl$_3$): δ 7.46 (d, J=2.0 Hz, 1H), 7.53 (dd, J=2.0, 8.6 Hz 1H), 7.76-7.81 (m, 2H), 8.00-8.05 (m, 1H), 8.25-8.31 (m, 1H), 8.33 (d, J=8.6 Hz, 1H), 10.64 (s, 1H).

MS: ESI (+ve) (Method B): 315 (M+H)$^+$, Retention time 3.9 min.

Preparation 40b: {3-[2-(2,4-dichlorobenzenesulfonyl)benzyl]-5-fluoro-2-methylindol-1-yl}acetic acid methyl ester The title compound was prepared by the method of Preparation 27c using 2-(2,4-dichlorobenzenesulfonyl)benzaldehyde and (5-fluoro-2-methylindol-1-yl)acetic acid methyl ester.

$^1$H NMR (CDCl$_3$): δ 2.14 (s, 3H), 3.75 (s, 3H), 4.12 (s, 2H), 4.77 (s, 2H), 6.42 (dd, J=2.5, 9.5 Hz, 1H), 6.84 (td, J=2.5, 9.0 Hz, 1H), 6.96-6.99 (m, 1H), 7.04 (dd, J=4.2, 8.8 Hz, 1H), 7.38-7.44 (m, 3H), 7.48 (d, J=2.0 Hz, 1H), 8.32-8.38 (m, 2H).

MS: ESI (+ve) (Method B): 520 (M+H)$^+$, Retention time 4.4 min

Preparation 40c: {3-[2-(2,4-dichlorobenzenesulfonyl)benzyl]-5-fluoro-2-methylindol-1-yl}acetic acid The title compound was prepared by the method of Preparation 19b using {3-[2-(2,4-dichlorobenzenesulfonyl)benzyl]-5-fluoro-2-methylindol-1-yl}acetic acid methyl ester.

$^1$H NMR (DMSO-$d_6$): δ 2.11 (s, 3H), 4.07 (s, 2H), 4.94 (s, 2H), 6.27 (dd, J=2.5, 9.9 Hz, 1H), 6.82 (td, J=2.5, 9.2, Hz, 1H), 7.00 (dd, J=1.6, 7.5 Hz, 1H), 7.32 (dd, J=4.4, 8.9 Hz, 1H), 7.51-7.60 (m, 2H), 7.72 (dd, J=2.1, 8.6 Hz, 1H), 7.86 (d, J=2.1 Hz, 1H), 8.26 (dd, J=1.8, 7.7 Hz, 1H, 8.35 (d, J=8.6 Hz, 1H).

MS: ESI (+ve) (Method A): 506 (M+H)$^+$, Retention time 12.2 min.

Example 41

{5-fluoro-3-[2-(4-fluorobenzenesulfonyl)benzyl]-2-methylindol-1-yl}acetic acid

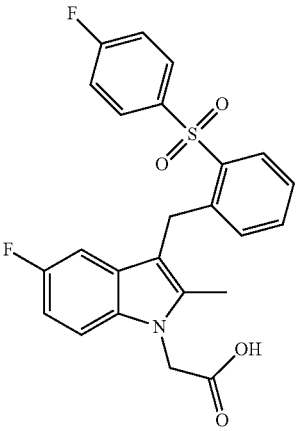 [SMILES: Cc1c(Cc2ccccc2S(=O)(=O)c2ccc(F)cc2)c2cc(F)ccc2n1CC(=O)O]

Preparation 41a:
2-(4-fluorobenzenesulfonyl)benzaldehyde

The title compound was prepared by the method of Preparation 33b using 2-[(4-fluorophenyl)thio]benzaldehyde.

$^1$H NMR (CDCl$_3$): δ 7.18-7.25 (m, 2H), 7.73-7.78 (m, 2H), 7.89-7.96 (m, 2H), 8.01-8.05 (m, 1H), 8.16-8.20 (m, 1H), 10.85 (d, J=0.64 Hz, 1H).

Preparation 41b: {5-fluoro-3-[2-(4-fluorobenzenesulfonyl)benzyl]-2-methylindol-1-yl}acetic acid methyl ester The title compound was prepared by the method of Preparation 27c using 2-(4-fluorobenzenesulfonyl)benzaldehyde and (5-fluoro-2-methylindol-1-yl)acetic acid methyl ester.

$^1$H NMR (CDCl$_3$): δ 2.15 (s, 3H), 3.76 (s, 3H), 4.22 (s, 2H), 4.78 (s, 2H), 6.31 (dd, J=2.5, 9.5, Hz, 1H), 6.83 (td, J=2.5, 9.0

Hz, 1H), 6.93-6.98 (m, 1H), 7.05 (dd, J=4.2, 8.8 Hz, 1H), 7.21 (t, J=8.5 Hz, 2H), 7.35-7.43 (m, 2H), 7.92-7.98 (m, 2H), 8.27-8.31 (m, 1H).

Preparation 41c: {5-fluoro-3-[2-(4-fluorobenzenesulfonyl)benzyl]-2-methylindol-1-yl}acetic acid The title compound was prepared by the method of Preparation 5c using {5-fluoro-3-[2-(4-fluorobenzenesulfonyl)benzyl]-2-methylindol-1-yl}acetic acid methyl ester.

$^1$H NMR (DMSO-$d_6$): δ 2.11 (s, 3H), 4.16 (s, 2H), 4.95 (s, 2H), 6.15 (dd, J=2.5, 9.8 Hz, 1H), 6.81 (td, J=2.5, 9.2 Hz, 1H), 6.92-6.97 (m, 1H), 7.30-7.37 (m, 1H), 7.44-7.55 (m, 4H), 7.99-8.05 (m, 2H), 8.19-8.25 (m, 1H).

MS: ESI (+ve) (Method A): 456 (M+H)$^+$, Retention time 11.1 min.

Example 42

[3-(4-benzenesulfonylthiazol-5-ylmethyl)-5-fluoro-2-methylindol-1-yl]acetic acid

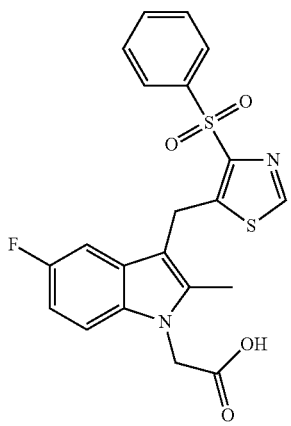 [SMILES: Cc1c(Cc2scnc2S(=O)(=O)c2ccccc2)c2cc(F)ccc2n1CC(=O)O]

Preparation 42a: 4-benzenesulfonylthiazole-5-carbaldehyde

A mixture of 4-chlorothiazole-5-carbaldehyde (0.15 g), benzenesulfinic acid sodium salt (0.25 g) and dimethyl sulfoxide (7.0 mL) was stirred at 100° C. for 30 minutes. The mixture was cooled to room temperature, poured onto ice/water (50 mL) and extracted with ethyl acetate. The combined organic extract was washed with saturated aqueous sodium chloride solution and dried over magnesium sulfate. The solvent was removed under reduced pressure to afford the title compound as a tan oil (0.23 g).

$^1$H NMR (CDCl$_3$): δ 7.57-7.63 (m, 2H), 7.67-7.73 (m, 1H), 8.11-8.14 (m, 2H), 8.95 (d, J=0.9 Hz, 1H), 10.83 (d, J=0.9 Hz, 1H).

Preparation 42b: [3-(4-benzenesulfonylthiazol-5-ylmethyl)-5-fluoro-2-methylindol-1-yl]acetic acid methyl ester A mixture of (5-fluoro-2-methylindol-1-yl)acetic acid methyl ester (0.2 g), 4-benzenesulfonylthiazole-5-carbaldehyde (0.23 g) and 1,2-dichloroethane (7.0 mL) at 0° C. was treated dropwise with a mixture of triethylsilane (2.2 mL), trifluoroacetic acid (0.6 mL) and 1,2-dichloroethane (2.0 mL), and the resulting mixture was stirred at room temperature overnight. The mixture was cooled to 0° C. and diluted with saturated aqueous sodium hydrogen carbonate solution. The phases were separated and the organic phase was dried over magnesium sulfate and concentrated under reduced pressure. The residue purified by column chromatography on silica gel, eluting with a mixture of ethyl acetate and dichloromethane (0:1 to 1:4 by volume) to afford the title compound as a white foam (0.20 g).

MS: ESI (+ve) (Method B): 459 (M+H)$^+$, Retention time 3.7 min.

Preparation 42c: [3-(4-benzenesulfonylthiazol-5-ylmethyl)-5-fluoro-2-methylindol-1-yl]acetic acid A mixture of lithium hydroxide (0.10 g), tetrahydrofuran (1.0 mL) and water (1.0 mL) was treated [3-(4-benzenesulfonylthiazol-5-ylmethyl)-5-fluoro-2-methylindol-1-yl]acetic acid methyl ester (0.20 g), and the resulting mixture was stirred at room temperature for 30 minutes. The mixture was diluted with water, concentrated to low bulk under reduced pressure and acidified by the addition of 1.0 M aqueous hydrochloric acid solution. The resulting precipitate was collected by filtration, washed with water and dried to afford the title compound as a white solid (0.19 g).

$^1$H NMR (DMSO-$d_6$): δ 2.30 (s, 3H), 4.70 (s, 2H), 4.96 (s, 2H), 6.90 (td, J=2.5, 9.2 Hz, 1H), 7.08 (dd, J=2.5, 9.8 Hz, 1H), 7.39 (dd, J=4.4, 8.9 Hz, 1H), 7.66-7.72 (m, 2H), 7.74-7.80 (m, 1H), 8.04-8.09 (m, 2H), 8.89 (s, 1H), 13.02 (br s, 1H).

MS: ESI (+ve) (Method A): 445 (M+H)$^+$, Retention time 10.1 min.

MS: ESI (+ve) (Method B): 445 (M+H)$^+$, Retention time 3.5 min.

Example 43

{5-fluoro-2-methyl-3-[4-(pyridine-2-sulfonyl)thiazol-5-ylmethyl]indol-1-yl}acetic acid

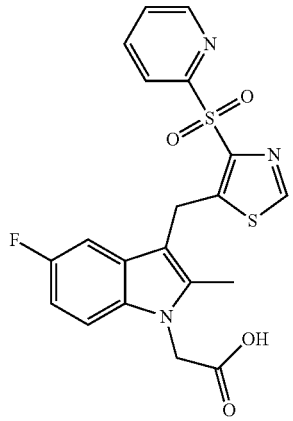 [SMILES: Cc1c(Cc2scnc2S(=O)(=O)c2ccccn2)c2cc(F)ccc2n1CC(=O)O]

Preparation 43a: 4-(pyridine-2-sulfonyl)thiazole-5-carbaldehyde

The title compound was prepared by the method of Preparation 42a using 4-chlorothiazole-5-carbaldehyde and pyridine-2-sulfinate sodium salt.

$^1$H NMR (CDCl$_3$): δ 7.54-7.59 (m, 1H), 7.99-8.06 (m, 1H), 8.34-8.38 (m, 1H), 8.67-8.71 (m, 1H), 8.96 (d, J=0.9 Hz, 1H), 10.85 (d, J=0.8 Hz, 1H).

Preparation 43b: {5-fluoro-2-methyl-3-[4-(pyridine-2-sulfonyl)thiazol-5-ylmethyl]indol-1-yl}acetic acid methyl ester The title compound was prepared by the method of Preparation 42b using 4-(pyridine-2-sulfonyl)thiazole-5-carbaldehyde and (5-fluoro-2-methylindol-1-yl)acetic acid methyl ester.
MS: ESI (+ve) (Method B): 460 (M+H)$^+$, Retention time 3.5 min.

Preparation 43c: {5-fluoro-2-methyl-3-[4-(pyridine-2-sulfonyl)thiazol-5-ylmethyl]indol-1-yl}acetic acid The title compound was prepared by the method of Preparation 42c using {5-fluoro-2-methyl-3-[4-(pyridine-2-sulfonyl)thiazol-5-ylmethyl]indol-1-yl}acetic acid methyl ester.
$^1$H NMR (DMSO-d$_5$): δ 2.36 (s, 3H), 4.77 (s, 2H), 4.97 (s, 2H), 6.91 (td, J=2.5, 9.2 Hz, 1H), 7.30 (dd, J=2.5, 9.9 Hz, 1H), 7.39 (dd, J=4.4, 8.9 Hz, 1H) 7.76-7.81 (m, 1H), 8.19-8.24 (m, 1H), 8.28 (dt, J=1.1, 7.9 Hz, 1H), 8.75-8.78 (m, 1H), 8.87 (s, 1H), 12.98 (br s, 1H).
MS: ESI (+ve) (Method A): 446 (M+H)$^+$, Retention time 9.1 min.
MS: ESI (+ve) (Method B): 446 (M+H)$^+$, Retention time 3.3 min.

Example 44

{3-[5-chloro-3-(pyridine-2-sulfonyl)thiophen-2-ylmethyl]-5-fluoro-2-methylindol-1-yl}acetic acid

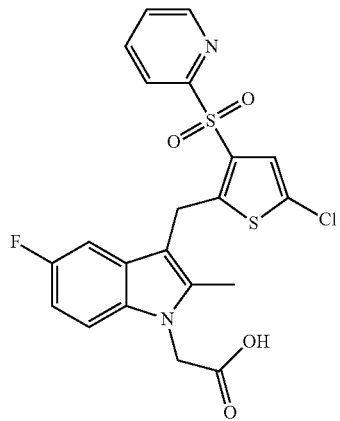 [SMILES: Cc1c(Cc2sc(Cl)cc2S(=O)(=O)c2ccccn2)c2cc(F)ccc2n1CC(=O)O]

Preparation 44a: 5-chloro-3-(pyridine-2-sulfonyl)thiophene-2-carbaldehyde

The title compound was prepared by the method of Preparation 42a using 3,5-dichlorothiophene-2-carbaldehyde and pyridine-2-sulfinate sodium salt.
$^1$H NMR (CDCl$_3$): δ 7.53-7.58 (m, 1H), 7.76 (s, 1H), 7.99 (td, J=1.7, 7.8 Hz, 1H), 8.17-8.22 (m, 1H), 8.73-8.76 (m, 1H), 10.08 (s, 1H).

Preparation 44b: {3-[5-chloro-3-(pyridine-2-sulfonyl)thiophen-2-ylmethyl]-5-fluoro-2-methylindol-1-yl}acetic acid methyl ester The title compound was prepared by the method of Preparation 42b using 5-chloro-3-(pyridine-2-sulfonyl)thiophene-2-carbaldehyde and (5-fluoro-2-methylindol-1-yl)acetic acid methyl ester.
MS: ESI (+ve) (Method B): 493 (M+H)$^+$, Retention time 4.0 min.

Preparation 44c: {3-[5-chloro-3-(pyridine-2-sulfonyl)thiophen-2-ylmethyl]-5-fluoro-2-methylindol-1-yl}acetic acid The title compound was prepared by the method of Preparation 42c using {3-[5-chloro-3-(pyridine-2-sulfonyl)thiophen-2-ylmethyl]-5-fluoro-2-methylindol-1-yl}acetic acid methyl ester.
$^1$H NMR (DMSO-d$_6$): δ 2.29 (s, 3H), 4.23 (s, 2H), 4.84 (s, 2H), 6.89 (td, J=2.5, 9.2 Hz, 1H), 7.16 (dd, J=2.5, 9.9 Hz, 1H), 7.36 (dd, J=4.4, 8.9 Hz, 1H), 7.65-7.73 (m, 1H), 7.85 (s, 1H), 8.10-8.14 (m, 2H), 8.70 (dt, J=1.3, 4.7 Hz, 1H).
MS: ESI (+ve) (Method A): 479 (M+H)$^+$, Retention time 11.1 min.
MS: ESI (+ve) (Method B): 479 (M+H)$^+$, Retention time 3.7 min.

Example 45

[3-(3-benzenesulfonyl-5-chlorothiophen-2-ylmethyl)-5-fluoro-2-methylindol-1-yl]-acetic acid

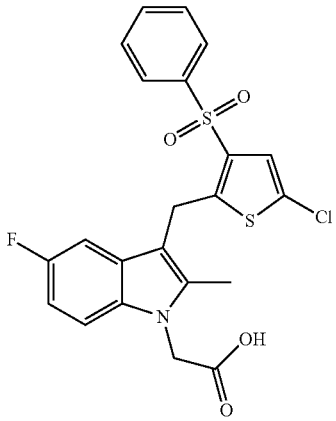 [SMILES: Cc1c(Cc2sc(Cl)cc2S(=O)(=O)c2ccccc2)c2cc(F)ccc2n1CC(=O)O]

Preparation 45a: 3-benzenesulfonyl-5-chlorothiophene-2-carbaldehyde

The title compound was prepared by the method of Preparation 42a using 3,5-dichlorothiophene-2-carbaldehyde and benzenesulfinic acid sodium salt.
$^1$H NMR (CDCl$_3$): δ 7.55-7.61 (m, 3H), 7.65-7.71 (m, 1H), 7.99-8.03 (m, 2H), 10.05 (s, 1H).

Preparation 45b: [3-(3-benzenesulfonyl-5-chlorothiophen-2-ylmethyl)-5-fluoro-2-methylindol-1-yl]acetic acid methyl ester The title compound was prepared by the method of Preparation 42b using 3-benzenesulfonyl-5-chlorothiophene-2-carbaldehyde and (5-fluoro-2-methylindol-1-yl)acetic acid methyl ester.

MS: ESI (+ve) (Method B): 492 (M+H)⁺, Retention time 4.2 min.

Preparation 45c: [3-(3-benzenesulfonyl-5-chlorothiophen-2-ylmethyl)-5-fluoro-2-methylindol-1-yl]acetic acid The title compound was prepared by the method of Preparation 42c using [3-(3-benzenesulfonyl-5-chlorothiophen-2-ylmethyl)-5-fluoro-2-methylindol-1-yl]acetic acid methyl ester.

$^1$H NMR (DMSO-d$_6$): δ 2.28 (s, 3H), 4.21 (s, 2H), 4.92 (s, 2H), 6.90 (td, J=2.6, 9.2 Hz, 1H), 7.16 (dd, J=2.6, 9.8 Hz, 1H), 7.39 (dd, J=4.4, 8.9 Hz, 1H), 7.58-7.64 (m, 2H), 7.67-7.73 (m, 1H), 7.89-7.94 (m, 3H).

MS: ESI (+ve) (Method A): 478 (M+H)⁺, Retention time 12.0 min.

MS: ESI (+ve) (Method B): 478 (M+H)⁺, Retention time 3.9 min.

Example 46

[3-(4-benzenesulfonyl-3-chloroisothiazol-5-ylmethyl)-5-fluoro-2-methyl-indol-1-yl]acetic acid

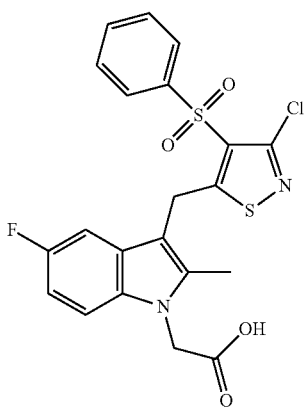 [SMILES: Cc1c(Cc2snc(Cl)c2S(=O)(=O)c2ccccc2)c2cc(F)ccc2n1CC(=O)O]

Preparation 46a: (3,4-dichloroisothiazol-5-yl)methanol

A mixture of 3,4-dichloroisothiazole-5-carboxylic acid (2.0 g) and toluene (20 mL) was treated with thionyl chloride (5.0 mL) and N,N-dimethylformamide (0.5 mL), and the resulting mixture was heated at 100° C. for 16 hours. The mixture was concentrated under reduced pressure and the residue was dissolved in tetrahydrofuran (5.0 mL). The mixture was cooled to −78° C. and treated dropwise over a period of 1 hour with a 2.0 M solution of sodium borohydride in N,N-dimethylformamide (8.5 mL). The mixture was stirred at −78° C. for 5 minutes, diluted with 1.0 M aqueous hydrochloric acid solution and extracted with ethyl acetate. The combined organic extract was washed with saturated aqueous sodium chloride solution, dried over sodium sulfate and concentrated under reduced pressure. The residue was purified by column chromatography on silica gel, eluting with a mixture of cyclohexane and dichloromethane (1:0 to 0:1 by volume) to afford the title compound as a pale yellow solid (1.1 g).

$^1$H NMR (CDCl$_3$): δ 4.96 (s, 2H).

Preparation 46b: 3,4-dichloroisothiazole-5-carbaldehyde

A mixture of (3,4-dichloroisothiazol-5-yl)methanol (1.1 g), chloroform (150 mL) and manganese dioxide (4.7 g) was stirred at 40° C. for 20 hours. The mixture was filtered through Celite and the filtrate was concentrated under reduced pressure to afford the title compound as a yellow solid (0.62 g).

$^1$H NMR (CDCl$_3$): δ 10.07 (s, 1H).

Preparation 46c: 4-benzenesulfonyl-3-chloroisothiazole-5-carbaldehyde

A mixture of 3,4-dichloroisothiazole-5-carbaldehyde (0.087 g), benzenesulfinic acid sodium salt (0.078 g) and dimethyl sulfoxide (3.0 mL) was stirred at room temperature for 3.5 hours. The mixture was diluted with water and extracted with ethyl acetate. The combined organic extract was washed with saturated aqueous sodium hydrogen carbonate solution and saturated aqueous sodium chloride solution and dried over magnesium sulfate. The solvent was removed under reduced pressure and the residue was purified by column chromatography on silica gel, eluting with a mixture of cyclohexane and ethyl acetate (1:0 to 0:1 by volume) to afford the title compound as a colourless oil (0.093 g).

$^1$H NMR (CDCl$_3$): δ 7.61-7.65 (m, 2H), 7.69-7.75 (m, 1H), 8.03-8.07 (m, 2H), 10.76 (s, 1H).

Preparation 46d: [3-(4-benzenesulfonyl-3-chloroisothiazol-5-ylmethyl)-5-fluoro-2-methylindol-1-yl]acetic acid methyl ester The title compound was prepared by the method of Preparation 1c using (5-fluoro-2-methylindol-1-yl)acetic acid methyl ester and 4-benzenesulfonyl-3-chloroisothiazole-5-carbaldehyde.

MS: ESI (+ve) (Method B): 493 (M+H)⁺, Retention time 4.6 min.

Preparation 47e: [3-(4-benzenesulfonyl-3-chloroisothiazol-5-ylmethyl)-5-fluoro-2-methylindol-1-yl]acetic acid A mixture of [3-(4-benzenesulfonyl-3-chloroisothiazol-5-ylmethyl)-5-fluoro-2-methylindol-1-yl]acetic acid methyl ester (0.065 g), tetrahydrofuran (20 mL) and 1.0 M aqueous lithium hydroxide solution (4.0 mL) was stirred at room temperature for 5 minutes. The mixture was concentrated under reduced pressure, acidified by the addition of 1.0 M aqueous hydrochloric acid solution and extracted with ethyl acetate. The combined organic extract was washed with saturated aqueous sodium chloride solution, dried over magnesium sulfate and concentrated under reduced pressure. The residue was purified by preparative reverse-phase HPLC, eluting with a mixture of acetonitrile and water (1:19 to 19:1 by volume) to afford the title compound as a white solid (0.050 g).

$^1$H NMR (CDCl$_3$): δ 2.29 (s, 3H), 4.76 (s, 2H), 4.97 (s, 2H), 6.91-6.96 (dt, J=2.5, 9.2 Hz, 1H), 7.22-7.26 (dd, J=2.5, 9.8 Hz, 1H), 7.42-7.45 (m, 1H), 7.71-7.76 (m, 2H), 7.81-7.85 (m, 1H), 8.18-8.20 (m, 2H), 13.5 (br s, 1H).

MS: ESI (+ve) (Method A): 479 (M+H)⁺, Retention time 11.5 min.

MS: ESI (+ve) (Method B): 479 (M+H)+, Retention time 3.9 min.

Example 47

[3-(4-benzenesulfonylisothiazol-5-ylmethyl)-5-fluoro-2-methyl indol-1-yl]acetic acid

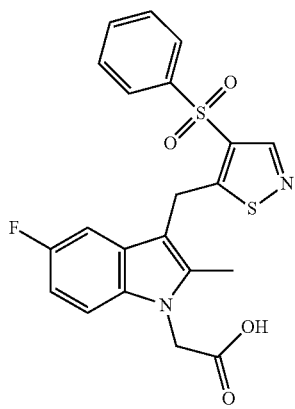 [SMILES: Cc1c(Cc2sncc2S(=O)(=O)c2ccccc2)c2cc(F)ccc2n1CC(=O)O]

Preparation 47a: [3-(4-benzenesulfonylisothiazol-5-ylmethyl)-5-fluoro-2-methylindol-1-yl]acetic acid The title compound was prepared by the method of Preparation 18a using [3-(4-benzenesulfonyl-3-chloroisothiazol-5-ylmethyl)-5-fluoro-2-methylindol-1-yl]acetic acid.

MS: ESI (+ve) (Method B): 445 (M+H)+, Retention time 3.7 min.

Example 48

[3-(5-benzenesulfonyl-1-methyl-1H-imidazol-4-ylmethyl)-5-fluoro-2-methyl-indol-1-yl]acetic acid

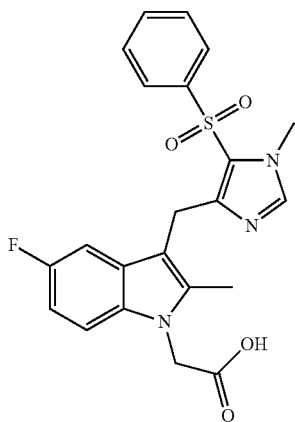 [SMILES: Cc1c(Cc2ncn(C)c2S(=O)(=O)c2ccccc2)c2cc(F)ccc2n1CC(=O)O]

Preparation 48a: 5-bromo-1-methyl-1H-imidazole-4-carbaldehyde

A mixture of 1-methyl-1H-imidazole-4-carbaldehyde (0.50 g), N-bromosuccinimide (0.89 g) and chloroform (7.0 mL) was heated at reflux for 2 hours. The mixture was cooled to 0° C., diluted with saturated aqueous sodium carbonate solution (10 mL) and extracted with dichloromethane. The combined organic extract was dried over magnesium sulfate and concentrated under reduced pressure. The residue was purified by column chromatography on silica gel, eluting with a mixture of ethyl acetate and dichloromethane (0:1 to 7:10 by volume) to afford the title compound as a white solid (0.37 g).

$^1$H NMR (CDCl$_3$): δ 3.70 (s, 3H), 7.66 (s, 1H), 9.89 (s, 1H).

Preparation 48b: 5-benzenesulfonyl-1-methyl-1H-imidazole-4-carbaldehyde

A mixture of benzenesulfinic acid sodium salt (0.065 g), 5-bromo-1-methyl-1H-imidazole-4-carbaldehyde (0.037 g) and dimethyl sulfoxide (2.0 mL) was heated by microwave irradiation at 180° C. for 10 minutes. The mixture was treated with additional benzenesulfinic acid sodium salt (0.065 g), and heated by microwave irradiation at 180° C. for 40 minutes. The mixture was diluted with ethyl acetate, washed with water and dried over magnesium sulfate. The solvent was removed under reduced pressure and the residue was triturated with cyclohexane to afford a yellow solid. The solid was collected by filtration, washed with cyclohexane and dried to afford the title compound (0.030 g).

MS: ESI (+ve) (Method B): 251 (M+H)+, Retention time 2.7 min.

Preparation 48c: [3-(5-benzenesulfonyl-1-methyl-1H-imidazol-4-ylmethyl)-5-fluoro-2-methylindol-1-yl]acetic acid methyl ester A mixture of triethylsilane (0.17 g), trifluoroacetic acid (0.10 g) and 1,2-dichloroethane (5.0 mL) at −5° C. was treated dropwise with a mixture of (5-fluoro-2-methylindol-1-yl)acetic acid methyl ester (0.022 g), 5-benzenesulfonyl-1-methyl-1H-imidazole-4-carbaldehyde (0.030 g) and 1,2-dichloroethane (3.0 mL), and the resulting mixture was stirred at room temperature overnight and then at 45° C. for 2 hours. The mixture was diluted with dichloromethane, washed with saturated aqueous sodium hydrogen carbonate solution and dried using a phase separation cartridge. The solvent was removed under reduced pressure and the residue was purified by column chromatography on silica gel, eluting with a mixture of ethyl acetate and dichloromethane (0:1 to 2:5 by volume) to afford the title compound as a yellow oil (0.027 g).

MS: ESI (+ve) (Method B): 456 (M+H)+, Retention time 3.5 min.

Preparation 48d: [3-(5-benzenesulfonyl-1-methyl-1H-imidazol-4-ylmethyl)-5-fluoro-2-methyl-indol-1-yl]acetic acid A mixture of [3-(5-benzenesulfonyl-1-methyl-1H-imidazol-4-ylmethyl)-5-fluoro-2-methylindol-1-yl]acetic acid methyl ester (0.027 g), methanol (3.0 mL) and 1.0 M aqueous sodium hydroxide solution (0.12 mL) was stirred at room temperature for 1 hour. The mixture was treated with tetrahydrofuran (1.0 mL) and 1.0 M aqueous sodium hydroxide solution (0.24 mL), and stirred at room temperature for 4 hours and then at 40° C. for 30 minutes. The mixture was concentrated under reduced pressure and acidified by the addition of 1.0 M aqueous hydrochloric acid solution. The resulting precipitate was collected by filtration, washed with water and dried to afford the title compound as a white solid (0.024 g).

$^1$H NMR (DMSO-d$_6$): δ 2.36 (s, 3H), 3.62 (s, 3H), 4.26 (s, 2H), 4.94 (s, 2H), 6.78-6.85 (m, 1H), 7.26 (dd, J=2.6, 10.9 Hz, 1H), 7.31 (dd, J=4.5, 8.9 Hz, 1H), 7.50-7.56 (m, 2H), 7.63-7.68 (m, 1H), 7.71-7.75 (m, 1H), 7.85 (d, J=1.1 Hz, 1H), 7.81 (s, 1H), 12.99 (br s, 1H).

MS: ESI (+ve) (Method A): 440 (M+H)$^+$, Retention time 9.3 min.

MS: ESI (+ve) (Method B): 442 (M+H)$^+$, Retention time 3.5 min.

Biological Methods

Compounds of the invention were tested using the following biological test method to determine their ability to displace PGD$_2$ from the CRTH2 receptor.

CRTH2 Radioligand Binding Assay

The receptor binding assay is performed in a final volume of 200 µL binding buffer [10 mM BES (pH 7.4), 1 mM EDTA, 10 mM manganese chloride, 0.01% BSA] and 1 nM [$^3$H]-PGD$_2$ (Amersham Biosciences UK Ltd). Ligands are added in assay buffer containing a constant amount of DMSO (1% by volume). Total binding is determined using 1% by volume of DMSO in assay buffer and non-specific binding is determined using 10 µM of unlabeled PGD$_2$ (Sigma). Human embryonic kidney (HEK) cell membranes (3.5 µg) expressing the CRTH2 receptor are incubated with 1.5 mg wheatgerm agglutinin SPA beads and 1 nM [$^3$H]-PGD$_2$ (Amersham Biosciences UK Ltd) and the mixture incubated for 3 hours at room temperature. Bound [$^3$H]-PGD$_2$ is detected using a Microbeta TRILUX liquid scintillation counter (Perkin Elmer). Compound IC$_{50}$ value is determined using a 6-point dose response curve in duplicate with a semi-log compound dilution series. IC$_{50}$ calculations are performed using Excel and XLfit (Microsoft), and this value is used to determine a K$_i$ value for the test compound using the Cheng-Prusoff equation.

GTPγS Functional Assay

The GTPγS Assay is performed in a final volume of 200 mL assay buffer (20 mM HEPES pH 7.4, 10 mM MgCl$_2$, 100 mM NaCl, 10 µg/mL saponin). DMSO concentrations are kept constant at 1% by volume. Human embryonic kidney (HEK) cell membranes (3.5 µg) expressing the CRTH2 receptor are incubated with the compounds for 15 min at 30° C. prior to addition of PGD$_2$ (30 nM final concentration) and GTP (10 µM final concentration). The assay solutions are then incubated for 30 minutes at 30° C., followed by addition of [$^{35}$S]-GTPγS (0.1 nM final concentration). The assay plate is than shaken and incubated for 5 minutes at 30° C. Finally, SPA beads (Amersham Biosciences, UK) are added to a final concentration of 1.5 mg/well and the plate shaken and incubated for 30 minute at 30° C. The sealed plate is centrifuged at 1000 g for 10 mins at 30° C. and the bound [$^{35}$S]-GTPγS is detected on Microbeta scintillation counter (Perkin Elmer). Compound IC$_{50}$ value is determined using a 6-point dose response curve in duplicate with a semi-log compound dilution series. IC$_{50}$ calculations are performed using Excel and XLfit (Microsoft), and this value is used to determine a Ki value for the test compound using the Cheng-Prusoff equation.

Biological Results

All compounds of the Examples above were tested in the CRTH2 radioligand binding assay described above; the compounds had a K$_i$ value of less than 2 µM in the binding assay. For example, Examples 1, 16, 21 and 26 had K$_i$ values of 1.5, 2.4, 0.6 and 4.5 nM respectively. Examples 1, 16 and 26, were tested in the GTPγS functional assay, and had K$_i$ values of less than 10 nM.

The invention claimed is:

1. A compound that is {5-fluoro-2-methyl-3[3-(pyridine-2-sulfonyl)thiophen-2-ylmethyl]indol-1-yl}acetic acid or a pharmaceutically acceptable salt thereof.

2. A pharmaceutical composition comprising a compound as claimed in claim 1 and a pharmaceutically acceptable carrier.

3. A method for treating a disease selected from asthma, chronic obstructive pulmonary disease, rhinitis, allergic airway syndrome, and allergic rhinobronchitis, comprising administering to a patient having such disease an effective amount of a compound as claimed in claim 1.

4. A method for treating a disease selected from psoriasis, atopic and non-atopic dermatitis, Crohn's disease, ulcerative colitis, and irritable bowel disease, comprising administering to a patient having such disease an effective amount of a compound as claimed in claim 1.

* * * * *

UNITED STATES PATENT AND TRADEMARK OFFICE
CERTIFICATE OF CORRECTION

PATENT NO.       : 8,394,836 B2  
APPLICATION NO.  : 12/746104  
DATED            : March 12, 2013  
INVENTOR(S)      : Hynd et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 362 days.

Signed and Sealed this
First Day of September, 2015

Michelle K. Lee
*Director of the United States Patent and Trademark Office*